US009688684B2

(12) United States Patent
Finsinger et al.

(10) Patent No.: US 9,688,684 B2
(45) Date of Patent: Jun. 27, 2017

(54) SUBSTITUTED TETRAZOLO[1,5-A]PYRAZINES AS ROR-GAMMA INHIBITORS

(71) Applicant: Merck Patent GmbH, Darmstadt (DE)

(72) Inventors: Dirk Finsinger, Darmstadt (DE); Margarita Wucherer-Plietker, Messel (DE); Beatrix Blume, Dossenheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/105,436

(22) PCT Filed: Nov. 26, 2014

(86) PCT No.: PCT/EP2014/003154
§ 371 (c)(1),
(2) Date: Jun. 16, 2016

(87) PCT Pub. No.: WO2015/090507
PCT Pub. Date: Jun. 25, 2015

(65) Prior Publication Data
US 2016/0311830 A1  Oct. 27, 2016

(30) Foreign Application Priority Data
Dec. 19, 2013  (EP) .................... 13005929

(51) Int. Cl.
*A61K 31/4985*  (2006.01)
*C07D 487/04*  (2006.01)
(52) U.S. Cl.
CPC ........ *C07D 487/04* (2013.01); *A61K 31/4985* (2013.01)
(58) Field of Classification Search
CPC .......................... A61K 31/4985; C07D 487/04
USPC .......................................... 514/249; 544/350
See application file for complete search history.

(56) References Cited

U.S. PATENT DOCUMENTS

2011/0313167 A1  12/2011  Doemling
2013/0211079 A1   8/2013  Doemling

OTHER PUBLICATIONS

Umkehrer, et al. Tetrahedron Letters, 45(34), 2004, 6421-6424.*
Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Hackam, et al. JAMA, 296(14), 2006, 1731-1732.*
International Preliminary Report on Patentability and Written Opinion of the International Searching Authority issued Jun. 30, 2016 in PCT/EP2014/003154 filed Nov. 26, 2014.
Jetten, A.M., "Retinoid-Related Orphan Receptors (RORs): Critical Roles in Development, Immunity, Circadian Rhythm, and Cellular Metabolism," *NRS*, 2009, vol. 7, pp. 1-32.
Jetten, A.M., et al., "Retinoic Acid-Related Orphan Receptors α and γ: Key Regulators of Lipid/Glucose Metabolism, Inflammation, and Insulin Sensitivity," *Frontiers in Endocrinology*, 2013, vol. 4, pp. 1-8.
International Search Report issued Jan. 9, 2015 in PCT/EP2014/003154 filed on Nov. 26, 2014.
Laura A. Solt, et al., "Action of RORs and their ligands in (patho)physiology", Trends in Endocrinology and Metabolism, XP055159433, vol. 23, No. 12, 2012, pp. 619-627.
Michael Umkehrer, et al., "Synthesis of tetrazolopiperazine building blocks by a novel multi-component reaction", Tetrahedron Letters, XP027304397, vol. 45, No. 34, 2004, pp. 6421-6424.

* cited by examiner

*Primary Examiner* — Douglas M Willis
(74) *Attorney, Agent, or Firm* — Oblon, McClelland, Maier & Neustadt, L.L.P.

(57) ABSTRACT

The present invention relates to tetrahydro-tetrazolo[1,5-a] pyrazine compounds of formula (I), wherein $R^1$ denotes —$R^3$, —$CH_2$—$R^3$ or —CO—$R^3$; $R^2$ denotes $Ar^2$, $Hetar^2$ or $C_{3-7}$-cycloalkyl; and $R^3$ denotes $Ar^3$, $Hetar^3$ or $C_{3-7}$-cycloalkyl. These compounds are useful for inhibiting the retinoid-related orphan receptor γ (ROR γ, ROR-gamma) and for the prevention and/or treatment of medical conditions affected by ROR γ activity such as rheumatoid arthritis, multiple sclerosis, psoriasis, ulcerative colitis, asthma, autoimmune hepatitis or type 1 and type 2 diabetes.

(I)

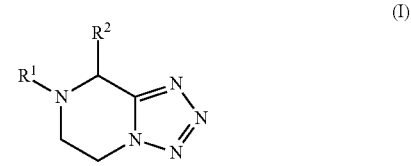

18 Claims, No Drawings

SUBSTITUTED TETRAZOLO[1,5-A]PYRAZINES AS ROR-GAMMA INHIBITORS

This application is a National Stage entry under 35 USC 371 of PCT/EP2014/003154, filed on Nov. 26, 2014, and claims priority to European Patent Application No. 13005929.8, filed on Dec. 19, 2013.

FIELD OF THE INVENTION

The present invention relates to tetrahydro-tetrazolo[1,5-a]pyrazines. These compounds are useful for inhibiting the retinoid-related orphan receptor γ (RORγ, ROR-gamma) and for the prevention and/or treatment of medical conditions affected by RORγ activity.

BACKGROUND OF THE INVENTION

Retinoid-related orphan receptors (RORs) constitute a subfamily of nuclear receptors (NR's) that function as ligand-dependent transcription factors. The ROR family comprises three members, namely RORα (ROR-alpha; NR1F1), RORβ (ROR-beta; NR1F2) and RORγ (ROR-gamma; NR1F3). They are termed "orphan" receptors because their endogenous ligands have yet to be agreed upon definitely. RORs exhibit a domain structure typical of nuclear receptors and contain an N-terminal domain, a highly conserved DNA-binding domain (DBD) consisting of two zinc finger motifs, a ligand-binding domain (LBD), and a hinge domain spacing the DBD and LBD (A. M. Jetten et al., Frontiers in Endocrinology Diabetes (2012) 4: 1; L. A. Salt and T. B. Burris, Trends in Endocrinology and Metabolism (2012) 23: 619). RORs recognize and bind as monomers to specific sequences of DNA, termed ROR response elements (ROREs), typically consisting of an AGGTCA site with a 5' AT-rich extension in the regulatory region of the target gene. When bound to this element within the promoters of that target genes, RORs recruit coactivators, leading to continual activation of transcription of that target genes.

The three RORs display significant sequence similarity and conservation between species. Each ROR gene generates multiple isoforms based on alternative promoter usage and exon splicing, with all of the isoforms varying only in the N-terminal region of the receptor. The RORs display distinct patterns of tissue expression and are involved in the regulation of various physiological processes (L. A. Salt and T. B. Burris, Trends in Endocrinology and Metabolism (2012) 23: 619). For instance in the ROR γ subfamily that consists of ROR γ1 and ROR γ2 (sometimes also referred to as ROR γt) ROR γ1 is expressed in many tissues, including liver, adipose, skeletal muscle, and kidney, while the expression of ROR γ2 is exclusively in a few distinct cell types of the immune system (A. M. Jetten, Nuclear Receptor Signaling (2009) 7: 1). Thus, ROR γ1 and in particular ROR γ2 are important regulators of several diverse immune functions. ROR γ2 plays an important role in the differentiation of naïve T cells into interleukin 17 (IL-17) producing T helper 17 (Th17) cells. Th17 cells are defined by a specific cytokine profile and secrete IL-17, IL-9, IL-21, IL-22, IL-26, and CCL20 (L. A. Salt and T. B. Burris, Trends in Endocrinology and Metabolism (2012) 23: 619). These mediators are responsible for several different effector functions in host defense as well as in autoimmune diseases. While Th17 cells play a significant role in host defense against extracellular pathogens as well as against obligate intracellular pathogens, these cells are also believed to be the major pro-inflammatory cells involved in autoimmunity (A. M. Jetten et al., Frontiers in Endocrinology Diabetes (2012) 4: 1; L. A. Salt and T. B. Burris, Trends in Endocrinology and Metabolism (2012) 23: 619; A. M. Jetten, Nuclear Receptor Signaling (2009) 7: 1). Since overexpression of ROR γ2 in naïve CD4+ T cells was demonstrated to drive the induction and development of those Th17 cells, inhibition of ROR γ with specific synthetic ligands has become a goal for medicinal chemistry in order to provide treatments for reducing autoimmune pathology.

It is also to be noted that ROR γ has been shown to play a role in the development of diabetes, adipositas and insulin resistance (A. M. Jetten et al., Frontiers in Endocrinology Diabetes (2012) 4: 1; L. A. Salt and T. B. Burris, Trends in Endocrinology and Metabolism (2012) 23: 619; A. M. Jetten, Nuclear Receptor Signaling (2009) 7: 1).

L. A. Salt and T. B. Burris, Trends in Endocrinology and Metabolism (2012) 23: 619; A. M. Jetten, Nuclear Receptor Signaling (2009) 7: 1, describe some synthetic ligands modulating the ROR γ activity. None of these synthetic ligands are tetrahydro-tetrazolo[1,5-a]pyrazines.

M. Umkehrer et al., Tetrahedron Lett. 45 (2004) 6421, disclose the synthesis of certain tetrahydro-tetrazolo[1,5-a]pyrazines by a multi-component reaction. In particular they disclose 7-benzyl-8-(4-methoxyphenyl)-5,6,7,8-tetrahydro-tetrazolo[1,5-a]pyrazine. They do not disclose any medicinal or pharmaceutical use or any activity on ROR γ of those compounds.

DESCRIPTION OF THE INVENTION

It is an object of the present invention to provide ROR γ inhibitors for the prevention and/or treatment of medical conditions that are affected by ROR γ activity. It is a particular object of the present invention to provide such inhibitors for the prevention and/or treatment of autoimmune diseases such as rheumatoid arthritis, collagen-induced arthritis (CIA), ankylosing spondylitis, systemic lupus erythematodus (SLE), psoriasis, atopic eczema, inflammatory bowel disease (IBD), Crohn's disease, ulcerative colitis, asthma, amyotrophic lateral sclerosis (ALS), autoimmune hepatitis, adipositas, type 1 and type 2 diabetes, insulin resistance and in particular multiple sclerosis (MS).

This object has surprisingly been solved by the compounds according to formula (I):

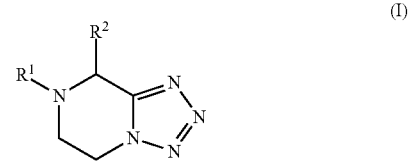

wherein
R$^1$ denotes —R$^3$, —CH$_2$—R$^3$ or —(C=O)—R$^3$;
R$^2$ denotes Ar$^2$, Hetar$^2$ or C$_{3-7}$-cycloalkyl;
R$^3$ denotes Ar$^3$, Hetar$^3$ or C$_{3-7}$-cycloalkyl;
Ar$^2$ and Ar$^3$ denote independently from each other a mono- or bicyclic aromatic hydrocarbon system having 6 to 10 carbon atoms which system is unsubstituted or substituted with one or more identical or different substituents selected from the group consisting of C$_{1-6}$-alkyl, C$_{1-6}$-alkoxy, C$_{3-7}$-cycloalkyl, —NH$_2$, N—(C$_{1-6}$-alkyl)amino, N,N-(di-C$_{1-6}$-alkyl)amino, halogen, —O—C$_{1-3}$-alkylene-O—;

Hetar² denotes a aromatic mono- or bicyclic, 4, 5, 6, 7, 8, 9 or 10 membered heterocycle having 1, 2 or 3 N and/or O and/or S atoms, which heterocycle is unsubstituted or substituted with one or more identical or different substituents selected from the group consisting of $C_{1-6}$-alkyl, $C_{3-7}$-cycloalkyl, $(C_{1-6}$-alkyl$)_m$-aryl wherein m is 0 or 1 and aryl is a mono- or bicyclic aromatic hydrocarbon system having 6 to 10 carbon atoms which aromatic hydrocarbon system is unsubstituted or substituted with one or more identical or different substituents selected from the group consisting of $C_{1-6}$-alkyl, $C_{1-6}$-alkoxy, $C_{3-7}$-cycloalkyl, —$NH_2$, N—($C_{1-6}$-alkyl)amino, N,N-(di-$C_{1-6}$-alkyl)amino, halogen;

Hetar³ denotes a aromatic mono- or bicyclic, 4, 5, 6, 7, 8, 9 or 10 membered heterocycle having 1, 2 or 3 N and/or O and/or S atoms, which system is unsubstituted or substituted with one or more identical or different substituents selected from the group consisting of $C_{1-6}$-alkyl, $C_{3-7}$-cycloalkyl, $(C_{1-6}$-alkyl$)_n$-aryl wherein n is 0 or 1 and aryl is a mono- or bicyclic aromatic hydrocarbon system having 6 to 10 carbon atoms which aromatic hydrocarbon system is unsubstituted or substituted with one or more identical or different substituents selected from the group consisting of $C_{1-6}$-alkyl, $C_{1-6}$-alkoxy, $C_{3-7}$-cycloalkyl, —$NH_2$, N—($C_{1-6}$-alkyl)amino, N,N-(di-$C_{1-6}$-alkyl)amino, halogen;

or derivatives, prodrugs, solvates, tautomers or stereoisomers thereof as well as the physiologically acceptable salts of each of the foregoing, including mixtures thereof in all ratios.

It is to be noted that while 7-benzyl-8-(4-methoxyphenyl)-5,6,7,8-tetrahydro-tetrazolo[1,5-a]pyrazine is already described in M. Umkehrer et al., Tetrahedron Lett. 45 (2004) 6421, and hence not claimed as compound per se, nevertheless that compound is also useful for inhibiting ROR γ and is therefore—inasmuch as its use in the prevention and/or treatment of medical conditions that are affected by inhibiting the retinoid-related orphan receptor gamma is concerned—part of the present invention.

In general, all residues which occur more than once may be identical or different, i.e. are independent of one another. Above and below, the residues and parameters have the meanings indicated for formula (I), unless expressly indicated otherwise. Accordingly, the invention relates, in particular, to the compounds of formula (I) in which at least one of the said residues has one of the preferred meanings indicated below.

One specific embodiment of the present invention comprises compounds of formula (I) wherein $R^1$ denotes —$CH_2$—$R^3$;
$R^2$ denotes $Ar^2$ or Hetar²;
$R^3$ denotes $Ar^3$ or Hetar³;
or derivatives, prodrugs, solvates, tautomers or stereoisomers thereof as well as the physiologically acceptable salts of each of the foregoing, including mixtures thereof in all ratios. This embodiment thus comprises compounds of formula (I) in which: $R^1$ is —$CH_2$—$Ar^3$ and $R^2$ is $Ar^2$ at the same time; or $R^1$ is —$CH_2$—$Ar^3$ and $R^2$ is Hetar² at the same time; or $R^1$ is —$CH_2$—Hetar³ and $R^2$ is $Ar^2$ at the same time; or $R^1$ is —$CH_2$—Hetar³ and $R^2$ is Hetar² at the same time.

One further specific embodiment of the present invention comprises compounds of formula (I) wherein $R^1$ denotes —$R^3$, —$CH_2$—$R^3$ or —(C=O)—$R^3$, preferably —$CH_2$—$R^3$;
$R^2$ denotes $Ar^2$, Hetar² or $C_{3-7}$-cycloalkyl, preferably $Ar^2$ or Hetar²;
$R^3$ denotes $Ar^3$, Hetar³ or $C_{3-7}$-cycloalkyl, preferably $Ar^3$ or Hetar³;
$Ar^2$ and $Ar^3$ denote independently from each other phenyl which is unsubstituted or substituted with one or two identical or different substituents selected from the group consisting of $C_{1-4}$-alkyl, $C_{1-4}$-alkoxy, —N,N-(di-$C_{1-6}$-alkyl)amino, F, Cl, Br, —O—$CH_2$—O— and —O—$CH_2$—$CH_2$—O—;

Hetar² denotes an aromatic monocyclic, 5 or 6 membered heterocycle having 1 or 2 N and/or S atoms, which system is unsubstituted or substituted with one or more identical or different substituents selected from the group consisting of $C_{1-4}$-alkyl, cyclopropyl, phenyl and —$CH_2$-phenyl wherein phenyl is unsubstituted or substituted with one or two identical or different substituents selected from the group consisting of $C_{1-6}$-alkyl, $C_{1-6}$-alkoxy and halogen;

Hetar³ denotes an aromatic monocyclic 5 or 6 membered or a bicyclic 8 or 9 membered heterocycle having 1 or 2 N and/or O and/or S atoms, which system is unsubstituted or substituted with one or more identical or different substituents selected from the group consisting of $C_{1-4}$-alkyl, cyclopropyl, phenyl and —$CH_2$-phenyl wherein phenyl is unsubstituted or substituted with one or two identical or different substituents selected from the group consisting of $C_{1-6}$-alkyl, $C_{1-6}$-alkoxy and halogen;

or derivatives, prodrugs, solvates, tautomers or stereoisomers thereof as well as the physiologically acceptable salts of each of the foregoing, including mixtures thereof in all ratios.

$Ar^2$ means preferably: phenyl which is unsubstituted or substituted with one or two identical or different substituents selected from the group consisting of methyl, ethyl, n-propyl, iso-propyl, n-butyl, tert-butyl, methoxy, ethoxy, n-propoxy, iso-propoxy, n-butoxy, tert-butoxy, —N,N-(di-methyl)amino, F, Cl, Br, —O—$CH_2$—O— or —O—$CH_2$—$CH_2$—O—; more preferably, $Ar^2$ is selected from the group consisting of phenyl, 3-methyl-phenyl, 4-ethyl-phenyl, 4-(iso-propyl)-phenyl, 4-methoxy-phenyl, 2,5-dimethoxy-phenyl, 4-ethoxy-phenyl, 4-(iso-propoxy)-phenyl, 4-(n-butoxy)-phenyl, 4-(N,N-dimethyl)amino-phenyl, 2-fluoro-phenyl, 3-fluoro-phenyl, 4-fluoro-phenyl, 2,3-difluoro-phenyl, 2,4-difluoro-phenyl, 2,5-difluoro-phenyl, 3,5-difluoro-phenyl, 4-chloro-phenyl, 3-bromo-phenyl, 2,3-dihydro-benzo[1,4]dioxin-6-yl, benzo[1,3]dioxol-5-yl.

Preferably, Hetar² stands for a heterocycle that is selected from the group consisting of pyridin-2-yl, pyridin-4-yl, thien-2-yl, pyrazol-4-yl, wherein that heterocycle is unsubstituted or substituted with one or two identical or different substituents selected from the group consisting of phenyl, —$CH_2$— phenyl, methyl, ethyl, iso-propyl, tert-butyl, cyclopropyl. It is even more preferred that Hetar² is selected from the group consisting of pyridin-2-yl, pyridin-4-yl, thien-2-yl, 3-cyclopropyl-1-methyl-1H-pyrazol-4-yl, 3-cyclopropyl-1-ethyl-1H-pyrazol-4-yl, 1-phenyl-3-(iso-propyl)-1H-pyrazol-4-yl, 1-methyl-3-(iso-propyl)-1H-pyrazol-4-yl, 1-benzyl-3-(iso-propyl)-1H-pyrazol-4-yl, 1-benzyl-3-(tert-butyl)-1H-pyrazol-4-yl.

$Ar^3$ preferably denotes phenyl which is unsubstituted or substituted with one or two identical or different substituents selected from the group consisting of methyl, methoxy, ethoxy, iso-propoxy, —N,N-(di-methyl)amino, F, Cl, Br or —O—$CH_2$—O—. More preferably, $Ar^3$ is selected from the group consisting of phenyl, 3-methyl-phenyl, 3-methoxy-phenyl, 4-methoxy-phenyl, 2,4-dimethoxy-phenyl, 2,5-dimethoxy-phenyl, 4-ethoxy-phenyl, 4-(iso-propoxy)-phenyl, 4-(N,N-dimethyl)amino-phenyl, 2-fluoro-phenyl, 3-fluoro-phenyl, 4-fluoro-phenyl, 2,3-difluoro-phenyl, 2,4-difluorophenyl, 2,5-difluoro-phenyl, 3-chloro-phenyl, 4-chloro-phenyl, 3-bromo-phenyl, 4-bromo-phenyl, benzo[1,3]dioxol-5-yl.

It is preferred that Hetar³ denotes a heterocycle that is selected from the group consisting of pyridin-2-yl, pyridin-3-yl, pyridin-4-yl, fur-2-yl, thien-2-yl, pyrazol-3-yl, pyrazol-4-yl, pyrazol-5-yl, pyrazolo[1,5-a]pyridine-3-yl, wherein that heterocycle is unsubstituted or substituted with one or two identical or different substituents selected from the group consisting of phenyl, —CH₂— phenyl, methyl, ethyl, iso-propyl. It is even more preferred that Hetar³ is selected from the group consisting of pyridin-3-yl, pyridin-4-yl, 5-methyl-fur-2-yl, thien-2-yl, 1-methyl-1H-pyrazol-3-yl, 1,3-dimethyl-1H-pyrazol-4-yl, 1,5-dimethyl-1H-pyrazol-4-yl, 1-ethyl-1H-pyrazol-4-yl, 1-benzyl-1H-pyrazol-4-yl, 1-phenyl-3-(iso-propyl)-1H-pyrazol-4-yl, 2H-pyrazol-3-yl, pyrazolo[1,5-a]pyridine-3-yl.

One particular embodiment of the present invention comprises compounds according to formula (I) wherein
R¹ denotes —CH₂—R³;
R² denotes Ar²;
R³ denotes Ar³;
Ar² is selected from the group consisting of phenyl, 3-methyl-phenyl, 4-ethyl-phenyl, 4-(iso-propyl)-phenyl, 4-methoxy-phenyl, 2,5-dimethoxy-phenyl, 4-ethoxy-phenyl, 4-(iso-propoxy)-phenyl, 4-(n-butoxy)-phenyl, 4-(N,N-dimethyl)amino-phenyl, 2-fluoro-phenyl, 3-fluoro-phenyl, 4-fluoro-phenyl, 2,3-difluoro-phenyl, 2,4-difluoro-phenyl, 2,5-difluoro-phenyl, 3,5-difluoro-phenyl, 4-chloro-phenyl, 3-bromo-phenyl, 2,3-dihydro-benzo[1,4]dioxin-6-yl; preferably selected from the group consisting of phenyl, 3-methyl-phenyl, 4-ethyl-phenyl, 4-(iso-propyl)-phenyl, 4-(iso-propoxy)-phenyl, 4-(n-butoxy)-phenyl, 4-(N,N-dimethyl)amino-phenyl, 3-fluoro-phenyl, 4-fluoro-phenyl, 2,5-difluoro-phenyl, 3,5-difluoro-phenyl, 4-chloro-phenyl, 3-bromo-phenyl, 2,3-dihydro-benzo[1,4]dioxin-6-yl; and
Ar³ is selected from the group consisting of phenyl, 3-methyl-phenyl, 4-ethoxy-phenyl, 4-(N,N-dimethyl)amino-phenyl, 2-fluoro-phenyl, 3-fluoro-phenyl, 4-fluoro-phenyl, 2,3-difluoro-phenyl, 3-chloro-phenyl, 4-chloro-phenyl, 3-bromo-phenyl, 4-bromo-phenyl, benzo[1,3]dioxol-5-yl; preferably selected from the group consisting of phenyl, 3-methyl-phenyl, 4-ethoxy-phenyl, 3-fluoro-phenyl, 4-fluoro-phenyl, 2,3-difluoro-phenyl, 3-chloro-phenyl, 3-bromo-phenyl, benzo[1,3]dioxol-5-yl.

Another particular embodiment of the present invention comprises compounds according to formula (I) wherein
R¹ denotes —CH₂—R³;
R² denotes Ar²;
R³ denotes Hetar³;
Ar² is selected from the group consisting of phenyl, 3-methyl-phenyl, 4-ethyl-phenyl, 4-(iso-propyl)-phenyl, 4-methoxy-phenyl, 2,5-dimethoxy-phenyl, 4-ethoxy-phenyl, 4-(iso-propoxy)-phenyl, 4-(n-butoxy)-phenyl, 4-(N,N-dimethyl)amino-phenyl, 2-fluoro-phenyl, 3-fluoro-phenyl, 4-fluoro-phenyl, 2,3-difluoro-phenyl, 2,4-difluoro-phenyl, 2,5-difluoro-phenyl, 3,5-difluoro-phenyl, 4-chloro-phenyl, 3-bromo-phenyl, 2,3-dihydro-benzo[1,4]dioxin-6-yl; preferably selected from the group consisting of phenyl, 3-methyl-phenyl, 4-ethyl-phenyl, 4-(iso-propyl)-phenyl, 4-(iso-propoxy)-phenyl, 4-(n-butoxy)-phenyl, 4-(N,N-dimethyl)amino-phenyl, 3-fluoro-phenyl, 4-fluoro-phenyl, 2,5-difluoro-phenyl, 3,5-difluoro-phenyl, 4-chloro-phenyl, 3-bromo-phenyl, 2,3-dihydro-benzo[1,4]dioxin-6-yl; and Hetar³ is selected from the group consisting of pyridin-4-yl, thien-2-yl, 1-benzyl-1H-pyrazol-4-yl, 1-phenyl-3-(iso-propyl)-1H-pyrazol-4-yl, 2H-pyrazol-3-yl, 1H-pyrazol-5-yl, pyrazolo[1,5-a]pyridine-3-yl; preferably is thien-2-yl (thiophen-2-yl).

Still another particular embodiment of the present invention comprises compounds according to formula (I) wherein
R¹ denotes —CH₂—R³;
R² denotes Hetar²;
R³ denotes Ar³;
Hetar² is selected from the group consisting of thien-2-yl, 3-cyclopropyl-1-ethyl-1H-pyrazol-4-yl, 1-phenyl-3-(iso-propyl)-1H-pyrazol-4-yl, 1-benzyl-3-(iso-propyl)-1H-pyrazol-4-yl, 1-benzyl-3-(tert-butyl)-1H-pyrazol-4-yl; preferably is 1-phenyl-3-(iso-propyl)-1H-pyrazol-4-yl;
Ar³ is selected from the group consisting of phenyl, 3-methyl-phenyl, 4-ethoxy-phenyl, 4-(N,N-dimethyl)amino-phenyl, 2-fluoro-phenyl, 3-fluoro-phenyl, 4-fluoro-phenyl, 2,3-difluoro-phenyl, 3-chloro-phenyl, 4-chloro-phenyl, 3-bromo-phenyl, 4-bromo-phenyl, benzo[1,3]dioxol-5-yl; preferably is selected from the group consisting of phenyl, 3-methyl-phenyl, 4-ethoxy-phenyl, 3-fluoro-phenyl, 4-fluoro-phenyl, 2,3-difluoro-phenyl, 3-chloro-phenyl, 3-bromo-phenyl, benzo[1,3]dioxol-5-yl.

Yet another particular embodiment of the present invention comprises compounds according to formula (I) wherein
R¹ denotes —CH₂—R³;
R² denotes Hetar²;
R³ denotes Hetar³;
Hetar² is selected from the group consisting of thien-2-yl, 3-cyclopropyl-1-ethyl-1H-pyrazol-4-yl, 1-phenyl-3-(iso-propyl)-1H-pyrazol-4-yl, 1-benzyl-3-(iso-propyl)-1H-pyrazol-4-yl, 1-benzyl-3-(tert-butyl)-1H-pyrazol-4-yl; preferably is 1-phenyl-3-(iso-propyl)-1H-pyrazol-4-yl;
Hetar³ is selected from the group consisting of pyridin-4-yl, thien-2-yl, 1-benzyl-1H-pyrazol-4-yl, 1-phenyl-3-(iso-propyl)-1H-pyrazol-4-yl, 2H-pyrazol-3-yl, 1H-pyrazol-5-yl, pyrazolo[1,5-a]pyridine-3-yl; preferably is thien-2-yl (thiophen-2-yl).

It is to be noted that the compounds of the present invention bear a stereogenic center at the carbon atom in 8-position of the tetrahydro-tetrazolo[1,5-a]pyrazine ring of formula (I); it has been denoted with an asterix (*) in formula (I)* below:

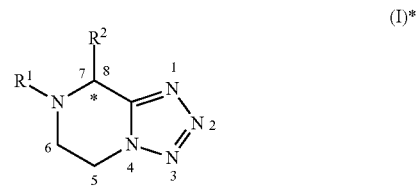

The compounds according to formula (I) thus exhibit two different configurations at this stereogenic center, i.e. the (R)-configuration and the (S)-configuration. Hence, the compounds of the present invention may be present as a racemic (1:1) mixture of the two enantiomers of formula (R)-(Ia) and (S)-(Ia).

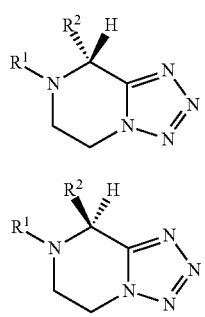

(R)-(Ia)

(S)-(Ia)

Compounds of formula (I) may also be present in a mixture in which one of the enantiomers (R)-(Ia) or (S)-(Ia) is present in an excess over the other one, e.g. 60:40, 70:30, 80:20, 90:10, 95:5 or the like, or even in enantiomerically pure form. It is to be noted that the compounds of the present invention are pharmacologically active on the ROR γ and therefore useful in the present invention already in racemic form, i.e. as racemates, one of the two enantiomers of formulas (R)-(Ia) and (S)-(Ia) may be more active than its optical antipode. In a particular embodiment of the present invention the stereoisomer of formula (R)-(Ia) of the compound of formula (Ia) and the stereoisomer of formula (S)-(Ia) of the compound of formula (Ia) are present in a ratio of (R)-(Ia) to (S)-(Ia) of at least 90 parts of (R)-(Ia) to not more than 10 parts of (S)-(Ia), preferably of at least 95 (R)-(Ia) to not more than 5 (S)-(Ia), more preferably of at least 99 (R)-(Ia) to not more than 1 (S)-(Ia), even more preferably of at least 99.5 (R)-(Ia) to not more than 0.5 (S)-(Ia). In another particular embodiment of the present invention the stereoisomer of formula (S)-(Ia) of the compound of formula (Ia) and the stereoisomer of formula (R)-(Ia) of the compound of formula (Ia) are present in a ratio of (S)-(Ia) to (R)-(Ia) of at least 90 (S)-(Ia) to not more than 10 (R)-(Ia), preferably of at least 95 (S)-(Ia) to not more than 5 (R)-(Ia), more preferably of at least 99 (S)-(Ia) to not more than 1 (R)-(Ia), even more preferably of at least 99.5 (S)-(Ia) to not more than 0.5 (R)-(Ia).

Enriched or pure stereoisomers of formulas (R)-(Ia) and (S)-(Ia) can be obtained by usual methods known in the art and described hereinafter. A particular method for obtaining them is preparative column chromatography, such as HPLC or SFC, using chiral column material.

Preferably, the compounds of the present invention are selected from the group consisting of 7-(2,5-Dimethoxy-benzyl)-8-(4-isopropoxy-phenyl)-5,6,7,8-tetrahydro-tetrazolo[1,5-a]pyrazine
7-(2-Fluoro-benzyl)-8-(4-isopropoxy-phenyl)-5,6,7,8-tetrahydro-tetrazolo[1,5-a]pyrazine
7-Cyclohexylmethyl-8-(4-isopropoxy-phenyl)-5,6,7,8-tetrahydro-tetrazolo[1,5-a]pyrazine
7-(2-Fluoro-benzyl)-8-(4-methoxy-phenyl)-5,6,7,8-tetrahydro-tetrazolo[1,5-a]pyrazine
7-(3-Isopropyl-1-phenyl-1H-pyrazol-4-ylmethyl)-8-(4-methoxy-phenyl)-5,6,7,8-tetrahydro-tetrazolo[1,5-a]pyrazine
7-(3-Bromo-benzyl)-8-(3-bromo-phenyl)-5,6,7,8-tetrahydro-tetrazolo[1,5-a]pyrazine
7-(3-Bromo-benzyl)-8-(2,3-difluoro-phenyl)-5,6,7,8-tetrahydro-tetrazolo[1,5-a]pyrazine
8-(3-Bromo-phenyl)-7-thiophen-2-ylmethyl-5,6,7,8-tetrahydro-tetrazolo[1,5-a]pyrazine
8-(3-Bromo-phenyl)-7-(3-isopropyl-1-phenyl-1H-pyrazol-4-ylmethyl)-5,6,7,8-tetrahydro-tetrazolo[1,5-a]pyrazine
8-(3-Bromo-phenyl)-7-cyclohexylmethyl-5,6,7,8-tetrahydro-tetrazolo[1,5-a]pyrazine
8-(3-Bromo-phenyl)-7-(2,3-difluoro-benzyl)-5,6,7,8-tetrahydro-tetrazolo[1,5-a]pyrazine
8-(4-Fluoro-phenyl)-7-(3-isopropyl-1-phenyl-1H-pyrazol-4-ylmethyl)-5,6,7,8-tetrahydro-tetrazolo[1,5-a]pyrazine
8-(2,5-Dimethoxy-phenyl)-7-(4-isopropoxy-benzyl)-5,6,7,8-tetrahydro-tetrazolo[1,5-a]pyrazine
8-(2,5-Dimethoxy-phenyl)-7-(3-isopropyl-1-phenyl-1H-pyrazol-4-ylmethyl)-5,6,7,8-tetrahydro-tetrazolo[1,5-a]pyrazine
{4-[7-(2-Fluoro-benzyl)-5,6,7,8-tetrahydro-tetrazolo[1,5-a]pyrazin-8-yl]-phenyl}-dimethyl-amine
[4-(7-Benzo[1,3]dioxol-5-ylmethyl-5,6,7,8-tetrahydro-tetrazolo[1,5-a]pyrazin-8-yl)-phenyl]-dimethyl-amine
{4-[7-(2,5-Difluoro-benzyl)-5,6,7,8-tetrahydro-tetrazolo[1,5-a]pyrazin-8-yl]-phenyl}-dimethyl-amine
{4-[7-(3-Fluoro-benzyl)-5,6,7,8-tetrahydro-tetrazolo[1,5-a]pyrazin-8-yl]-phenyl}-dimethyl-amine
{4-[7-(3-Isopropyl-1-phenyl-1H-pyrazol-4-ylmethyl)-5,6,7,8-tetrahydro-tetrazolo[1,5-a]pyrazin-8-yl]-phenyl}dimethyl-amine
[4-(7-Cyclohexylmethyl-5,6,7,8-tetrahydro-tetrazolo[1,5-a]pyrazin-8-yl)-phenyl]-dimethyl-amine
{4-[7-(2,3-Difluoro-benzyl)-5,6,7,8-tetrahydro-tetrazolo[1,5-a]pyrazin-8-yl]-phenyl}-dimethyl-amine
8-(2-Fluoro-phenyl)-7-(4-isopropoxy-benzyl)-5,6,7,8-tetrahydro-tetrazolo[1,5-a]pyrazine
8-(2-Fluoro-phenyl)-7-(4-methoxy-benzyl)-5,6,7,8-tetrahydro-tetrazolo[1,5-a]pyrazine
{4-[8-(2-Fluoro-phenyl)-5,6-dihydro-8H-tetrazolo[1,5-a]pyrazin-7-ylmethyl]-phenyl}-dimethyl-amine
7-(2,5-Difluoro-benzyl)-8-(2-fluoro-phenyl)-5,6,7,8-tetrahydro-tetrazolo[1,5-a]pyrazine
8-(2-Fluoro-phenyl)-7-(3-isopropyl-1-phenyl-1H-pyrazol-4-ylmethyl)-5,6,7,8-tetrahydro-tetrazolo[1,5-a]pyrazine
7-(2,3-Difluoro-benzyl)-8-(2-fluoro-phenyl)-5,6,7,8-tetrahydro-tetrazolo[1,5-a]pyrazine
7-(3-Isopropyl-1-phenyl-1H-pyrazol-4-ylmethyl)-8-m-tolyl-5,6,7,8-tetrahydro-tetrazolo[1,5-a]pyrazine
[4-(8-Benzo[1,3]dioxol-5-yl-5,6-dihydro-8H-tetrazolo[1,5-a]pyrazin-7-ylmethyl)-phenyl]-dimethyl-amine
8-Benzo[1,3]dioxol-5-yl-7-(3-isopropyl-1-phenyl-1H-pyrazol-4-ylmethyl)-5,6,7,8-tetrahydro-tetrazolo[1,5-a]pyrazine
{4-[8-(2,5-Difluoro-phenyl)-5,6-dihydro-8H-tetrazolo[1,5-a]pyrazin-7-ylmethyl]-phenyl}-dimethyl-amine
8-(2,5-Difluoro-phenyl)-7-(2-fluoro-benzyl)-5,6,7,8-tetrahydro-tetrazolo[1,5-a]pyrazine
7-(2,5-Difluoro-benzyl)-8-(2,5-difluoro-phenyl)-5,6,7,8-tetrahydro-tetrazolo[1,5-a]pyrazine
8-(2,5-Difluoro-phenyl)-7-(3-fluoro-benzyl)-5,6,7,8-tetrahydro-tetrazolo[1,5-a]pyrazine
8-(2,5-Difluoro-phenyl)-7-(3-isopropyl-1-phenyl-1H-pyrazol-4-ylmethyl)-5,6,7,8-tetrahydro-tetrazolo[1,5-a]pyrazine
7-(2,3-Difluoro-benzyl)-8-(2,5-difluoro-phenyl)-5,6,7,8-tetrahydro-tetrazolo[1,5-a]pyrazine
{4-[8-(3-Fluoro-phenyl)-5,6-dihydro-8H-tetrazolo[1,5-a]pyrazin-7-ylmethyl]-phenyl}-dimethyl-amine
7-(2,5-Difluoro-benzyl)-8-(3-fluoro-phenyl)-5,6,7,8-tetrahydro-tetrazolo[1,5-a]pyrazine
7-(3-Fluoro-benzyl)-8-(3-fluoro-phenyl)-5,6,7,8-tetrahydro-tetrazolo[1,5-a]pyrazine 7-(4-Chloro-benzyl)-8-(3-fluoro-phenyl)-5,6,7,8-tetrahydro-tetrazolo[1,5-a]pyrazine
8-(3-Fluoro-phenyl)-7-(3-isopropyl-1-phenyl-1H-pyrazol-4-ylmethyl)-5,6,7,8-tetrahydro-tetrazolo[1,5-a]pyrazine
7-(2,3-Difluoro-benzyl)-8-(3-fluoro-phenyl)-5,6,7,8-tetrahydro-tetrazolo[1,5-a]pyrazine
8-(4-Chloro-phenyl)-7-(3-fluoro-benzyl)-5,6,7,8-tetrahydro-tetrazolo[1,5-a]pyrazine
8-(4-Ethoxy-phenyl)-7-(3-isopropyl-1-phenyl-1H-pyrazol-4-ylmethyl)-5,6,7,8-tetrahydro-tetrazolo[1,5-a]pyrazine
7-Cyclohexylmethyl-8-(4-ethoxy-phenyl)-5,6,7,8-tetrahydro-tetrazolo[1,5-a]pyrazine
7-(2,3-Difluoro-benzyl)-8-(4-ethoxy-phenyl)-5,6,7,8-tetrahydro-tetrazolo[1,5-a]pyrazine
7-(4-Bromo-benzyl)-8-thiophen-2-yl-5,6,7,8-tetrahydro-tetrazolo[1,5-a]pyrazine
8-Thiophen-2-yl-7-thiophen-2-ylmethyl-5,6,7,8-tetrahydro-tetrazolo[1,5-a]pyrazine
7-(3-Isopropyl-1-phenyl-1H-pyrazol-4-ylmethyl)-8-thiophen-2-yl-5,6,7,8-tetrahydro-tetrazolo[1,5-a]pyrazine
7-Cyclohexylmethyl-8-thiophen-2-yl-5,6,7,8-tetrahydro-tetrazolo[1,5-a]pyrazine
7-(2,3-Difluoro-benzyl)-8-thiophen-2-yl-5,6,7,8-tetrahydro-tetrazolo[1,5-a]pyrazine
8-(3-Isopropyl-1-phenyl-1H-pyrazol-4-yl)-7-(4-methoxy-benzyl)-5,6,7,8-tetrahydro-tetrazolo[1,5-a]pyrazine
7-(4-Bromo-benzyl)-8-(3-isopropyl-1-phenyl-1H-pyrazol-4-yl)-5,6,7,8-tetrahydro-tetrazolo[1,5-a]pyrazine
7-(4-Fluoro-benzyl)-8-(3-isopropyl-1-phenyl-1H-pyrazol-4-yl)-5,6,7,8-tetrahydro-tetrazolo[1,5-a]pyrazine
7-(2,5-Dimethoxy-benzyl)-8-(3-isopropyl-1-phenyl-1H-pyrazol-4-yl)-5,6,7,8-tetrahydro-tetrazolo[1,5-a]pyrazine
{4-[8-(3-Isopropyl-1-phenyl-1H-pyrazol-4-yl)-5,6-dihydro-8H-tetrazolo[1,5-a]pyrazin-7-ylmethyl]-phenyl}-dimethyl-amine
7-(2-Fluoro-benzyl)-8-(3-isopropyl-1-phenyl-1H-pyrazol-4-yl)-5,6,7,8-tetrahydro-tetrazolo[1,5-a]pyrazine
8-(3-Isopropyl-1-phenyl-1H-pyrazol-4-yl)-7-(3-methyl-benzyl)-5,6,7,8-tetrahydro-tetrazolo[1,5-a]pyrazine
7-Benzo[1,3]dioxol-5-ylmethyl-8-(3-isopropyl-1-phenyl-1H-pyrazol-4-yl)-5,6,7,8-tetrahydro-tetrazolo[1,5-a]pyrazine
7-(2,5-Difluoro-benzyl)-8-(3-isopropyl-1-phenyl-1H-pyrazol-4-yl)-5,6,7,8-tetra hydro-tetrazolo[1,5-a]pyrazine
7-(4-Ethoxy-benzyl)-8-(3-isopropyl-1-phenyl-1H-pyrazol-4-yl)-5,6,7,8-tetrahydro-tetrazolo[1,5-a]pyrazine
8-(3-Isopropyl-1-phenyl-1H-pyrazol-4-yl)-7-thiophen-2-ylmethyl-5,6,7,8-tetrahydro-tetrazolo[1,5-a]pyrazine
8-(3-Isopropyl-1-phenyl-1H-pyrazol-4-yl)-7-(3-isopropyl-1-phenyl-1H-pyrazol-4-ylmethyl)-5,6,7,8-tetrahydro-tetrazolo[1,5-a]pyrazine
7-(2,3-Difluoro-benzyl)-8-(3-isopropyl-1-phenyl-1H-pyrazol-4-yl)-5,6,7,8-tetrahydro-tetrazolo[1,5-a]pyrazine
8-Cyclohexyl-7-(4-isopropoxy-benzyl)-5,6,7,8-tetrahydro-tetrazolo[1,5-a]pyrazine
7-(3-Bromo-benzyl)-8-cyclohexyl-5,6,7,8-tetrahydro-tetrazolo[1,5-a]pyrazine
[4-(8-Cyclohexyl-5,6-dihydro-8H-tetrazolo[1,5-a]pyrazin-7-ylmethyl)-phenyl]-dimethyl-amine
8-Cyclohexyl-7-(4-ethoxy-benzyl)-5,6,7,8-tetrahydro-tetrazolo[1,5-a]pyrazine
8-Cyclohexyl-7-thiophen-2-ylmethyl-5,6,7,8-tetrahydro-tetrazolo[1,5-a]pyrazine
8-Cyclohexyl-7-cyclohexylmethyl-5,6,7,8-tetrahydro-tetrazolo[1,5-a]pyrazine
7-(3-Bromo-benzyl)-8-(2,3-difluoro-phenyl)-5,6,7,8-tetrahydro-tetrazolo[1,5-a]pyrazine
8-(2,3-Difluoro-phenyl)-7-(2,5-dimethoxy-benzyl)-5,6,7,8-tetrahydro-tetrazolo[1,5-a]pyrazine
{4-[8-(2,3-Difluoro-phenyl)-5,6-dihydro-8H-tetrazolo[1,5-a]pyrazin-7-ylmethyl]-phenyl}-dimethyl-amine
8-(2,3-Difluoro-phenyl)-7-(2-fluoro-benzyl)-5,6,7,8-tetrahydro-tetrazolo[1,5-a]pyrazine
7-(2,5-Difluoro-benzyl)-8-(2,3-difluoro-phenyl)-5,6,7,8-tetrahydro-tetrazolo[1,5-a]pyrazine
8-(2,3-Difluoro-phenyl)-7-(3-fluoro-benzyl)-5,6,7,8-tetrahydro-tetrazolo[1,5-a]pyrazine
8-(2,3-Difluoro-phenyl)-7-(4-ethoxy-benzyl)-5,6,7,8-tetrahydro-tetrazolo[1,5-a]pyrazine
8-(2,3-Difluoro-phenyl)-7-thiophen-2-ylmethyl-5,6,7,8-tetrahydro-tetrazolo[1,5-a]pyrazine
8-(2,3-Difluoro-phenyl)-7-(3-isopropyl-1-phenyl-1H-pyrazol-4-ylmethyl)-5,6,7,8-tetrahydro-tetrazolo[1,5-a]pyrazine
7-(2,3-Difluoro-benzyl)-8-(2,3-difluoro-phenyl)-5,6,7,8-tetrahydro-tetrazolo[1,5-a]pyrazine
7-(2,4-Dimethoxy-benzyl)-8-(3-fluoro-phenyl)-5,6,7,8-tetrahydro-tetrazolo[1,5-a]pyrazine
8-(3-Fluoro-phenyl)-5,6,7,8-tetrahydro-tetrazolo[1,5-a]pyrazine
(3-Bromo-phenyl)-[8-(3-fluoro-phenyl)-5,6-dihydro-8H-tetrazolo[1,5-a]pyrazin-7-yl]-methanone
8-(4-Fluoro-phenyl)-7-pyridin-3-ylmethyl-5,6,7,8-tetrahydro-tetrazolo[1,5-a]pyrazine
8-(4-Fluoro-phenyl)-7-pyridin-4-ylmethyl-5,6,7,8-tetrahydro-tetrazolo[1,5-a]pyrazine
8-(4-Fluoro-phenyl)-7-(1-methyl-1H-pyrazol-3-ylmethyl)-5,6,7,8-tetrahydro-tetrazolo[1,5-a]pyrazine
7-(3-Methyl-benzyl)-8-pyridin-2-yl-5,6,7,8-tetrahydro-tetrazolo[1,5-a]pyrazine
7-(3-Methyl-benzyl)-8-pyridin-4-yl-5,6,7,8-tetrahydro-tetrazolo[1,5-a]pyrazine
7-Benzyl-8-(4-isopropoxy-phenyl)-5,6,7,8-tetrahydro-tetrazolo[1,5-a]pyrazine
7-Benzyl-8-(3-fluoro-phenyl)-5,6,7,8-tetrahydro-tetrazolo[1,5-a]pyrazine
7-Benzyl-8-(4-ethyl-phenyl)-5,6,7,8-tetrahydro-tetrazolo[1,5-a]pyrazine
7-(4-Fluoro-benzyl)-8-(3-fluoro-phenyl)-5,6,7,8-tetrahydro-tetrazolo[1,5-a]pyrazine
7-(3-Bromo-benzyl)-8-m-tolyl-5,6,7,8-tetrahydro-tetrazolo[1,5-a]pyrazine
8-(4-Fluoro-phenyl)-7-(3-methyl-benzyl)-5,6,7,8-tetrahydro-tetrazolo[1,5-a]pyrazine
7-Benzyl-8-(3-bromo-phenyl)-5,6,7,8-tetrahydro-tetrazolo[1,5-a]pyrazine
8-(2,3-Dihydro-benzo[1,4]dioxin-6-yl)-7-(3-methyl-benzyl)-5,6,7,8-tetrahydro-tetrazolo[1,5-a]pyrazine
7-(3-Bromo-benzyl)-8-(4-fluoro-phenyl)-5,6,7,8-tetrahydro-tetrazolo[1,5-a]pyrazine
8-(4-Chloro-phenyl)-7-(3-methyl-benzyl)-5,6,7,8-tetrahydro-tetrazolo[1,5-a]pyrazine
7-(2,3-Difluoro-benzyl)-8-(2,5-dimethoxy-phenyl)-5,6,7,8-tetrahydro-tetrazolo[1,5-a]pyrazine
7-Benzyl-8-(4-butoxy-phenyl)-5,6,7,8-tetrahydro-tetrazolo[1,5-a]pyrazine
8-(4-Isopropoxy-phenyl)-7-(3-methyl-benzyl)-5,6,7,8-tetrahydro-tetrazolo[1,5-a]pyrazine
7-Benzyl-8-m-tolyl-5,6,7,8-tetrahydro-tetrazolo[1,5-a]pyrazine
7-Benzyl-8-(3,5-difluoro-phenyl)-5,6,7,8-tetrahydro-tetrazolo[1,5-a]pyrazine
7-Benzyl-8-(4-fluoro-phenyl)-5,6,7,8-tetra hydro-tetrazolo[1,5-a]pyrazine 8-(4-Butoxy-phenyl)-7-(3-methyl-benzyl)-5,6,7,8-tetrahydro-tetrazolo[1,5-a]pyrazine 7-(3-Bromo-benzyl)-8-(4-isopropyl-phenyl)-5,6,7,8-tetrahydro-tetrazolo[1,5-a]pyrazine 7-(3-Methyl-benzyl)-8-phenyl-5,6,7,8-tetrahydro-tetrazolo[1,5-a]pyrazine 8-(4-Chloro-phenyl)-7-thiophen-2-ylmethyl-5,6,7,8-tetrahydro-tetrazolo[1,5-a]pyrazine 7-(3-Bromo-benzyl)-8-(3,5-difluoro-phenyl)-5,6,7,8-tetrahydro-tetrazolo[1,5-a]pyrazine 7-(3-Bromo-benzyl)-8-(2,5-difluoro-phenyl)-5,6,7,8-tetrahydro-tetrazolo[1,5-a]pyrazine {4-[7-(3-Bromo-benzyl)-5,6,7,8-tetrahydro-tetrazolo[1,5-a]pyrazin-8-yl]-phenyl}-dimethyl-amine 7-(3-Bromo-benzyl)-8-(4-isopropoxy-phenyl)-5,6,7,8-tetrahydro-tetrazolo[1,5-a]pyrazine 7-Benzyl-8-(4-chloro-phenyl)-5,6,7,8-tetrahydro-tetrazolo[1,5-a]pyrazine 7-Benzyl-8-(2,5-difluoro-phenyl)-5,6,7,8-tetrahydro-tetrazolo[1,5-a]pyrazine 7-Benzyl-8-(2,3-difluoro-phenyl)-5,6,7,8-tetrahydro-tetrazolo[1,5-a]pyrazine 7-Cyclohexyl-8-(3-isopropyl-1-phenyl-1H-pyrazol-4-yl)-5,6,7,8-tetrahydro-tetrazolo[1,5-a]pyrazine 7-(3-Bromo-benzyl)-8-(4-ethoxy-phenyl)-5,6,7,8-tetrahydro-tetrazolo[1,5-a]pyrazine 8-(3-Fluoro-phenyl)-7-(3-methyl-benzyl)-5,6,7,8-tetrahydro-tetrazolo[1,5-a]pyrazine 8-(3-Fluoro-phenyl)-7-thiophen-2-ylmethyl-5,6,7,8-tetrahydro-tetrazolo[1,5-a]pyrazine 8-(4-Ethoxy-phenyl)-7-(3-methyl-benzyl)-5,6,7,8-tetrahydro-tetrazolo[1,5-a]pyrazine 7-(3-Bromo-benzyl)-8-(2-fluoro-phenyl)-5,6,7,8-tetrahydro-tetrazolo[1,5-a]pyrazine 7-(3-Bromo-benzyl)-8-(4-methoxy-phenyl)-5,6,7,8-tetrahydro-tetrazolo[1,5-a]pyrazine 8-(4-Isopropoxy-phenyl)-7-thiophen-2-ylmethyl-5,6,7,8-tetrahydro-tetrazolo[1,5-a]pyrazine 7-Benzyl-8-(4-methoxy-phenyl)-5,6,7,8-tetrahydro-tetrazolo[1,5-a]pyrazine 7-(3-Bromo-benzyl)-8-phenyl-5,6,7,8-tetrahydro-tetrazolo[1,5-a]pyrazine 8-(3,5-Difluoro-phenyl)-7-thiophen-2-ylmethyl-5,6,7,8-tetrahydro-tetrazolo[1,5-a]pyrazine 8-(4-Fluoro-phenyl)-7-thiophen-2-ylmethyl-5,6,7,8-tetrahydro-tetrazolo[1,5-a]pyrazine {4-[7-(4-Fluoro-benzyl)-5,6,7,8-tetrahydro-tetrazolo[1,5-a]pyrazin-8-yl]-phenyl}-dimethyl-amine 7-Benzyl-8-phenyl-5,6,7,8-tetrahydro-tetrazolo[1,5-a]pyrazine 8-(2,5-Dimethoxy-phenyl)-7-(4-fluoro-benzyl)-5,6,7,8-tetrahydro-tetrazolo[1,5-a]pyrazine Dimethyl-{4-[7-(3-methyl-benzyl)-5,6,7,8-tetrahydro-tetrazolo[1,5-a]pyrazin-8-yl]-phenyl}-amine 8-(4-Butoxy-phenyl)-7-(2-fluoro-benzyl)-5,6,7,8-tetrahydro-tetrazolo[1,5-a]pyrazine 7-Benzo[1,3]dioxol-5-ylmethyl-8-(4-isopropoxy-phenyl)-5,6,7,8-tetrahydro-tetrazolo[1,5-a]pyrazine 7-(4-Fluoro-benzyl)-8-(4-isopropoxy-phenyl)-5,6,7,8-tetrahydro-tetrazolo[1,5-a]pyrazine 8-(2,3-Dihydro-benzo[1,4]dioxin-6-yl)-7-(4-fluoro-benzyl)-5,6,7,8-tetrahydro-tetrazolo[1,5-a]pyrazine 8-(4-Ethoxy-phenyl)-7-(4-fluoro-benzyl)-5,6,7,8-tetrahydro-tetrazolo[1,5-a]pyrazine 7-Benzyl-8-(2,5-dimethoxy-phenyl)-5,6,7,8-tetrahydro-tetrazolo[1,5-a]pyrazine 8-(2,4-Difluoro-phenyl)-7-(3-methyl-benzyl)-5,6,7,8-tetrahydro-tetrazolo[1,5-a]pyrazine 8-(2-Fluoro-phenyl)-7-thiophen-2-ylmethyl-5,6,7,8-tetrahydro-tetrazolo[1,5-a]pyrazine 8-(4-Chloro-phenyl)-7-(2-fluoro-benzyl)-5,6,7,8-tetrahydro-tetrazolo[1,5-a]pyrazine 8-Phenyl-7-thiophen-2-ylmethyl-5,6,7,8-tetrahydro-tetrazolo[1,5-a]pyrazine 8-(2,5-Difluoro-phenyl)-7-thiophen-2-ylmethyl-5,6,7,8-tetrahydro-tetrazolo[1,5-a]pyrazine 8-(2,5-Dimethoxy-phenyl)-7-(2-fluoro-benzyl)-5,6,7,8-tetrahydro-tetrazolo[1,5-a]pyrazine 8-(4-Isopropoxy-phenyl)-7-(5-methyl-furan-2-ylmethyl)-5,6,7,8-tetrahydro-tetrazolo[1,5-a]pyrazine 7-(3-Chloro-benzyl)-8-(3-isopropyl-1-phenyl-1H-pyrazol-4-yl)-5,6,7,8-tetrahydro-tetrazolo[1,5-a]pyrazine 8-(3-Cyclopropyl-1-ethyl-1H-pyrazol-4-yl)-7-thiophen-2-ylmethyl-5,6,7,8-tetrahydro-tetrazolo[1,5-a]pyrazine 8-(3-Isopropyl-1-methyl-1H-pyrazol-4-yl)-7-thiophen-2-ylmethyl-5,6,7,8-tetrahydro-tetrazolo[1,5-a]pyrazine 7-(4-Fluoro-benzyl)-8-(4-methoxy-phenyl)-5,6,7,8-tetrahydro-tetrazolo[1,5-a]pyrazine 7-(3-Methoxy-benzyl)-8-(4-methoxy-phenyl)-5,6,7,8-tetrahydro-tetrazolo[1,5-a]pyrazine 7-(4-Chloro-benzyl)-8-(3-isopropyl-1-phenyl-1H-pyrazol-4-yl)-5,6,7,8-tetrahydro-tetrazolo[1,5-a]pyrazine {4-[7-(4-Isopropoxy-benzyl)-5,6,7,8-tetrahydro-tetrazolo[1,5-a]pyrazin-8-yl]-phenyl}-dimethyl-amine 7-Benzyl-8-(3-isopropyl-1-phenyl-1H-pyrazol-4-yl)-5,6,7,8-tetrahydro-tetrazolo[1,5-a]pyrazine 7-Benzyl-8-(4-ethyl-phenyl)-8-methyl-5,6,7,8-tetrahydro-tetrazolo[1,5-a]pyrazine 8-(3-Isopropyl-1-phenyl-1H-pyrazol-4-yl)-7-(2H-pyrazol-3-ylmethyl)-5,6,7,8-tetrahydro-tetrazolo[1,5-a]pyrazine 8-(3-Isopropyl-1-phenyl-1H-pyrazol-4-yl)-7-pyrazolo[1,5-a]pyridin-3-ylmethyl-5,6,7,8-tetrahydro-tetrazolo[1,5-a]pyrazine 7-(1-Ethyl-1H-pyrazol-4-ylmethyl)-8-(3-isopropyl-1-phenyl-1H-pyrazol-4-yl)-5,6,7,8-tetrahydro-tetrazolo[1,5-a]pyrazine 7-(1,5-Dimethyl-1H-pyrazol-4-ylmethyl)-8-(3-isopropyl-1-phenyl-1H-pyrazol-4-yl)-5,6,7,8-tetrahydro-tetrazolo[1,5-a]pyrazine 8-(3-Isopropyl-1-phenyl-1H-pyrazol-4-yl)-7-(1,3,5-trimethyl-1H-pyrazol-4-ylmethyl)-5,6,7,8-tetrahydro-tetrazolo[1,5-a]pyrazine 7-(2-Chloro-benzyl)-8-(3-isopropyl-1-phenyl-1H-pyrazol-4-yl)-5,6,7,8-tetrahydro-tetrazolo[1,5-a]pyrazine 8-(3-Cyclopropyl-1-methyl-1H-pyrazol-4-yl)-7-thiophen-2-ylmethyl-5,6,7,8-tetrahydro-tetrazolo[1,5-a]pyrazine 8-(1-Benzyl-3-tert-butyl-1H-pyrazol-4-yl)-7-thiophen-2-ylmethyl-5,6,7,8-tetrahydro-tetrazolo[1,5-a]pyrazine 7-(1-Benzyl-1H-pyrazol-4-ylmethyl)-8-(3-isopropyl-1-phenyl-1H-pyrazol-4-yl)-5,6,7,8-tetrahydro-tetrazolo[1,5-a]pyrazine 8-(1-Benzyl-3-isopropyl-1H-pyrazol-4-yl)-7-thiophen-2-ylmethyl-5,6,7,8-tetrahydro-tetrazolo[1,5-a]pyrazine 7-(3-Bromo-benzyl)-8-(3-fluoro-phenyl)-5,6,7,8-tetrahydro-tetrazolo[1,5-a]pyrazine

[4-(7-Benzyl-5,6,7,8-tetrahydro-tetrazolo[1,5-a]pyrazin-8-yl)-phenyl]-dimethyl-amine (R)-7-Benzyl-8-(4-ethyl-phenyl)-8-methyl-5,6,7,8-tetrahydro-tetrazolo[1,5-a]pyrazine (S)-7-Benzyl-8-(4-ethyl-phenyl)-8-methyl-5,6,7,8-tetrahydro-tetrazolo[1,5-a]pyrazine (R)-8-(3-Isopropyl-1-phenyl-1H-pyrazol-4-yl)-7-thiophen-2-ylmethyl-5,6,7,8-tetrahydro-tetrazolo[1,5-a]pyrazine (S)-8-(3-Isopropyl-1-phenyl-1H-pyrazol-4-yl)-7-thiophen-2-ylmethyl-5,6,7,8-tetrahydro-tetrazolo[1,5-a]pyrazine (R)-7-(3-Bromo-benzyl)-8-(4-fluoro-phenyl)-5,6,7,8-tetrahydro-tetrazolo[1,5-a]pyrazine (S)-7-(3-Bromo-benzyl)-8-(4-fluoro-phenyl)-5,6,7,8-tetrahydro-tetrazolo[1,5-a]pyrazine (R)-7-(3-Bromo-benzyl)-8-m-tolyl-5,6,7,8-tetrahydro-tetrazolo[1,5-a]pyrazine (S)-7-(3-Bromo-benzyl)-8-m-tolyl-5,6,7,8-tetrahydro-tetrazolo[1,5-a]pyrazine (S)-7-Benzyl-8-(4-ethyl-phenyl)-5,6,7,8-tetrahydro-tetrazolo[1,5-a]pyrazine (R)-7-Benzyl-8-(4-ethyl-phenyl)-5,6,7,8-tetrahydro-tetrazolo[1,5-a]pyrazine (R)-7-Benzyl-8-(4-butoxy-phenyl)-5,6,7,8-tetrahydro-tetrazolo[1,5-a]pyrazine (S)-7-Benzyl-8-(4-butoxy-phenyl)-5,6,7,8-tetrahydro-tetrazolo[1,5-a]pyrazine (R)-8-(4-Fluoro-phenyl)-7-(3-methyl-benzyl)-5,6,7,8-tetrahydro-tetrazolo[1,5-a]pyrazine (S)-8-(4-Fluoro-phenyl)-7-(3-methyl-benzyl)-5,6,7,8-tetrahydro-tetrazolo[1,5-a]pyrazine (S)-7-(4-Fluoro-benzyl)-8-(3-fluoro-phenyl)-5,6,7,8-tetrahydro-tetrazolo[1,5-a]pyrazine (R)-7-(4-Fluoro-benzyl)-8-(3-fluoro-phenyl)-5,6,7,8-tetrahydro-tetrazolo[1,5-a]pyrazine, or derivatives, prodrugs, solvates, tautomers or stereoisomers thereof as well as the physiologically acceptable salts of each of the foregoing, including mixtures thereof in all ratios.

In the context of the present invention "halogen" refers to fluorine (—F), chlorine (—Cl), bromine (—Br) and iodine (—I) atoms. Preferably, "halogen" means —F, —Cl or —Br.

In the context of the present invention the phrase "aromatic hydrocarbon system having 6 to 10 carbon atoms" refers to aromatic hydrocarbon residues having 6, 7, 8, 9 or 10 carbon atoms forming the core structure of the system; the term "aryl" is used as a synonym of the term "aromatic hydrocarbon system". Preferably, the "aromatic hydrocarbon system" and likewise "aryl" is monocyclic and comprises 6 carbon atoms, i.e. is a phenyl moiety, or is bicyclic and comprises 10 carbon atoms, e.g. is a naphthyl or azulenyl moiety. In the context of the present invention, the aromatic hydrocarbon system—and likewise aryl—is most preferably a phenyl moiety. The aromatic hydrocarbon system having 6 to 10 carbon atoms—and likewise aryl—may be unsubstituted or substituted with one or more identical or different substituents which means that in case of substitution with one substituent 1H atom that is attached to one of the carbon atoms of the aromatic hydrocarbon system is replaced by a substituent or radical different than hydrogen whereas in case of substitution with more than one substituent 2, 3, 4 or more, preferably 2 or 3, most preferably 2, of the H atoms attached to the carbon atoms of the aromatic hydrocarbon system are replaced by either the identical or different substituents or radicals. For the purpose of the present invention the substituents are independently selected from the group consisting of $C_{1-6}$-alkyl, $C_{1-6}$-alkoxy, $C_{3-7}$-cycloalkyl, —$NH_2$, N—($C_{1-6}$-alkyl)amino, N,N-(di-$C_{1-6}$-alkyl)amino, halogen, —O—$C_{1-3}$-alkylene-O— all of which are as defined herein. It is to be understood that in case of substitution with "—O—$C_{1-3}$-alkylene-O—" 2H atoms are replaced by that substituent and that one of oxygen atoms of the substituent is attached to a first carbon atom of the aromatic hydrocarbon system whereas the other oxygen is attached to a second carbon atom thereof; preferably, those two carbon atoms are adjacent to each other. Preferably, the "aromatic hydrocarbon system having 6 to 10 carbon atoms"- and likewise "aryl"—is phenyl that is unsubstituted or substituted with 1 or 2 identical or different of the above-mentioned substituents.

In the context of the present invention the term "heterocycle" or "heterocyclyl" refers in its most general meaning to a mono- or polycyclic ring system having j ring atoms with j being an integer in the range of 3 to 20 and comprising (j-k) carbon atom(s) and k heteroatom(s) with k being an integer in the range of 1 to 7; and k<j. The hetero atoms are selected from N and/or S and/or O. That ring system may be unsubstituted or substituted with one or more identical or different substituents. It may be saturated, unsaturated (meaning that one or more of the bonds between ring atoms are double or triple bounds, preferably double bonds) or aromatic (also referred to as heteroaromatic). Preferably, j is 3, 4, 5, 6, 7, 8, 9, 10, 11, 12, 13 or 14, and k is 1, 2, 3, 4, 5 or 6. More preferably, j is 5, 6, 7, 8, 9 or 10, and k is 1, 2, 3, 4 or 5. Furthermore, preferably the heterocycle is a mono-, bi- or tricyclic ring system, more preferably a mono- or bicyclic ring system. In general, such heterocycle may be attached to any compound, substituent, residue, moiety or radical described herein via any of its ring atoms. Examples of a suitable non-aromatic "heterocycle" are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl, indolinyl, indolinylmethyl, imidazolidinyl, 2-aza-bicyclo[2.2.2]octanyl. Examples of a suitable aromatic "heterocycle", also referred to as "heteroaryl", are furanyl, furazanyl, furyl, imidazolyl, indazolyl, indolinyl, indolizinyl, indolyl, isobenzylfuranyl, isoindolyl, isoquinolinyl, isoquinolyl, isothiazolyl, isoxazolyl, naphthyridinyl, oxadiazolyl, oxazolyl, phenazinyl, phenothiazinyl, phenoxazinyl, phthalazinyl, pteridinyl, purinyl, pyrazinyl, pyrazolyl, pyridazinyl, pyridinyl, pyridyl, pyrimidinyl, pyrimidyl, pyrrolyl, quinazolinyl, quinolinyl, quinolyl, quinoxalinyl, tetrazolyl, thiadiazolyl, thiazolyl, thienyl, thiophenyl, triazinyl, triazolyl, acridinyl, benzdioxinyl, benzimidazolyl, benzisoxazolyl, benzodioxolyl, benzofuranyl, benzothiadiazolyl, benzothiazolyl, benzothienyl, benzoxazolyl, carbazolyl, cinnolinyl, dibenzofuranyl, tetrazolopyrazinyl.

For the purpose of the present invention "alkyl" denotes an aliphatic, saturated hydrocarbon radical having 1, 2, 3, 4, 5, 6, 7, 8, 9, 10, 11, 12, 13, 14, 15, 16, 17 or 18 carbon atoms. The alkyl radical may be straight-chain or branched. Optionally, 1, 2 or 3 of the hydrogen atoms of the alkyl radical can independently from each other be replaced by halogen, —OH, $C_{1-6}$-alkoxy, cyano, nitro, amino, N—($C_{1-6}$-alkyl)-amino and/or N,N-di-($C_{1-6}$-alkyl)-amino. 1 or 2 of the —$CH_2$— groups of an alkyl radical (but not a terminal —$CH_3$ group) may also be replaced independently from each other by —O—, —$SO_2$—, —NH—, or —N($CH_3$)—, it being understood that two —$CH_2$— groups directly linked to each other are not replaced by any of these divalent radicals at the same time (thus, e.g., no —O—O— or —NH—NH— moieties are comprised). Examples of "alkyl" are, inter alia, methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl; trifluoromethyl, —$CH_2CF_3$, —$CHFCHF_2$, —$(CH_2)_3$—OH, —$(CH_2)_2CH(OCH_3)CH_3$, —$(CH_2)_2$—CN, —$(CH_2)_3$—$NH_2$, —$(CH_2)_6$—$NHCH_3$, —$CH_2CH(CH_3)CH_2N$ (CH$_2$CH$_3$)$_2$; —(CH$_2$)$_2$—O—(CH$_2$)$_2$CH$_3$, —(CH$_2$)$_3$—SO$_2$—CH$_3$, —(CH$_2$)$_4$—NH—CH$_3$, —(CH$_2$)$_2$—NH(CH$_3$)—CH$_2$CH$_3$.

In the context of the present invention "C$_{1-6}$-alkyl" means an alkyl moiety having 1, 2, 3, 4, 5 or 6 carbon atoms and being straight-chain or branched. Optionally, 1, 2 or 3 of the hydrogen atoms of the C$_{1-6}$-alkyl radical can independently from each other be replaced by halogen, —OH, C$_{1-6}$-alkoxy, cyano, nitro, amino, N—(C$_{1-6}$-alkyl)amino and/or N,N-di-(C$_{1-6}$-alkyl)amino. 1 of the —CH$_2$— groups of a C$_{1-6}$-alkyl radical (but not a terminal —CH$_3$ group) may also be replaced by —O—, —SO$_2$—, —NH—, or —N(CH$_3$)—. Examples of "C$_{1-6}$-alkyl" comprise, but are not limited to methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl. The term "C$_{1-4}$-alkyl" comprises alkyl radicals having 1, 2, 3 or 4 carbon atoms and being straight-chain or branched; it comprises, but is not limited to methyl, ethyl, n-propyl, isopropyl, n-butyl, isobutyl, sec-butyl, tert-butyl. Preferably, "alkyl" means "C$_{1-6}$-alkyl", most preferably "C$_{1-4}$-alkyl".

In the context of the present invention the term "C$_{1-6}$-alkoxy" means a —O—C$_{1-6}$-alkyl radical that is attached to any compound, substituent, residue, moiety or radical described herein via its oxygen atom wherein "C$_{1-6}$-alkyl" is as defined herein, it being understood that 1 of the —CH$_2$— groups of the C$_{1-6}$-alkyl radical (but not a terminal —CH$_3$ group and not a —CH$_2$— group adjacent to the alkoxy-O— except for —SO$_2$—) may optionally be replaced by —SO$_2$—, —NH—, or —N(CH$_3$)—. Examples of "C$_{1-6}$-alkoxy" comprise, but are not limited to, methoxy, ethoxy, n-propoxy, isopropoxy, n-butoxy, tert-butoxy, n-pentoxy, n-hexoxy. Preferred examples are methoxy, ethoxy, isopropoxy, n-butoxy.

In the context of the present invention the term "C$_{3-7}$-cycloalkyl" refers to saturated mono- or bicyclic hydrocarbon groups (alicyclic radicals) having 3, 4, 5, 6 or 7 carbon atoms. Preferably, the cycloalkyl radical is monocyclic. The bonding to any compound, substituent, residue, moiety or radical described herein can be effected via any possible ring member of the cycloalkyl radical. The cycloalkyl moiety may be unsubstituted or substituted with 1 or 2 C$_{1-6}$-alkyl and/or C$_{1-6}$-alkoxy radicals. Preferably, the cycloalkyl moiety is unsubstituted. Examples of suitable C$_{3-7}$-cycloalkyl radicals comprise, but are not limited to, cyclopropyl, cyclobutyl, cyclopentyl, cyclohexyl, cycloheptyl, bicyclo[2.2.1]hexanyl, bicycle[2.2.2]heptanyl. Preferred examples of C$_{3-7}$-cycloalkyl are cyclopropyl and cyclohexyl, in particular cyclopropyl.

In the context of the present invention the term "N—(C$_{1-6}$-alkyl)amino" refers to an amino group in which one of the H atoms attached to the nitrogen atom is replaced by a C$_{1-6}$-alkyl radical that is defined as herein. Likewise, the term N,N-(di-C$_{1-6}$-alkyl)amino refers to an amino group in which both H atoms attached to the N atom have been replaced by C$_{1-6}$-alkyl radicals that radicals being as defined herein and being different or, as preferred, the same. Preferably, the C$_{1-6}$-alkyl radical(s) is (are) unsubstituted. It is understood that the N—(C$_{1-6}$-alkyl)amino group and the N,N-(di-C$_{1-6}$-alkyl)amino group, respectively, is attached to any compound, substituent, residue, moiety or radical described herein via its nitrogen atom.

For the purpose of the present invention in the terms "(C$_{1-6}$-alkyl)$_m$-aryl" and "(C$_{1-6}$-alkyl)$_n$-aryl" "(C$_{1-6}$-alkyl)" and "aryl" have the same meaning as defined hereinabove and hereinafter. Preferably, aryl in "(C$_{1-6}$-alkyl)$_m$-aryl" and "(C$_{1-6}$-alkyl)$_n$-aryl", respectively, is a mono- or bicyclic aromatic hydrocarbon system having 6 to 10 carbon atoms which aromatic hydrocarbon system is unsubstituted or substituted with one or more identical or different substituents selected from the group consisting of C$_{1-6}$-alkyl, C$_{1-6}$-alkoxy, C$_{3-7}$-cycloalkyl, —NH$_2$, N—(C$_{1-6}$-alkyl)amino, N,N-(di-C$_{1-6}$-alkyl)amino, halogen; most preferably, a phenyl moiety being unsubstituted or substituted with one or two identical or different substituents selected from the group consisting of C$_{1-6}$-alkyl, C$_{1-6}$-alkoxy and halogen. m and n are independently from each other 0 or 1, preferably 0.

In the context of the present invention the term "alkylene" in the term "—O—C$_{1-3}$-alkylene-O—" refers to a divalent saturated aliphatic residue comprising 1, 2 or 3 carbon atoms. It may be, for instance, —O—CH$_2$—O—, —O—CH$_2$CH$_2$—O—, —O—CH$_2$CH$_2$CH$_2$—O— or —O—C(CH$_3$)$_2$—O—. Preferably, it is —O—CH$_2$—O— or —O—CH$_2$CH$_2$—O—.

In the context of the present invention the term "unsubstituted" means that the corresponding radical, group or moiety has no substituents other than H; the term "substituted" means that the corresponding radical, group or moiety has one or more substituents. Where a radical has a plurality of substituents, i.e. at least two, and a selection of various substituents is specified, the substituents are selected independently of one another and do not need to be identical.

It is well known that atoms may have atomic masses or mass numbers which differ from the atomic masses or mass numbers of the atoms which usually occur naturally. Examples of isotopes which are readily commercially available and which can be incorporated into a compound of the present invention by well-known methods include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Incorporation of heavier isotopes, especially deuterium ($^2$H), into a compound of the invention has therapeutic advantages owing to the higher metabolic stability of this isotope-labelled compound. Higher metabolic stability translates directly into an increased in vivo half-life or lower dosages. Therefore, these isotopes are included in the definition of atoms H, C, N etc., as used in the chemical compounds of this invention.

The compounds of the present invention can be in the form of a prodrug compound. "Prodrugs" and "prodrug compound" mean a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, in which the amino group in a compound of the present invention is acylated, alkylated or phosphorylated, e.g., eicosanoylamino, alanylamino, pivaloyloxymethylamino or in which the hydroxyl group is acylated, alkylated, phosphorylated or converted into the borate, e.g. acetyloxy, palmitoyloxy, pivaloyloxy, succinyloxy, fumaryloxy, alanyloxy or in which the carboxyl group is esterified or amidated, or in which a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

The term "solvates" means addition forms of the compounds of the present invention with solvents, preferably pharmaceutically acceptable solvents, that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherate, e.g., diethyl etherate.

The compounds of formula (I) may have one or more centres of chirality. They may accordingly occur in various enantiomeric forms and be in racemic or optically active form. The invention, therefore, also relates to the optically active forms, enantiomers, racemates, diastereomers, collectively: "stereoisomers" for the purpose of the present invention, of these compounds. Since the pharmaceutical activity of the racemates or stereoisomers of the compounds according to the invention may differ, it may be desirable to use a specific stereoisomer, e.g. one specific enantiomer or diastereomer. In these cases, a compound according to the present invention obtained as a racemate—or even intermediates thereof—may be separated into the stereoisomeric (enantiomeric, diasterreoisomeric) compounds by chemical or physical measures known to the person skilled in the art. Another approach that may be applied to obtain one or more specific stereoisomers of a compound of the present invention in an enriched or pure form makes use of stereoselective synthetic procedures, e.g. applying starting material in a stereoisomerically enriched or pure form (for instance using the pure or enriched (R)- or (S)-enantiomer of a particular starting material bearing a chiral center) or utilizing chiral reagents or catalysts, in particular enzymes.

Thus, for example, the compounds of the invention which have one or more centers of chirality and which occur as racemates or as mixtures of enatiomers or diastereoisomers can be fractionated or resolved by methods known per se into their optically pure or enriched isomers, i.e. enantiomers or diastereomers. The separation of the compounds of the invention can take place by chromatographic methods, e.g. column separation on chiral or nonchiral phases, or by recrystallization from an optionally optically active solvent or by use of an optically active acid or base or by derivatization with an optically active reagent such as, for example, an optically active alcohol, and subsequent elimination of the radical.

In the context of the present invention the term "tautomer" refers to compounds of the present invention that may exist in tautomeric forms and show tautomerism; for instance, carbonyl compounds may be present in their keto and/or their enol form and show keto-enol tautomerism. Those tautomers may occur in their individual forms, e.g., the keto or the enol form, or as mixtures thereof and are claimed separately and together as mixtures in any ratio. The same applies for cis/trans isomers, E/Z isomers, conformers and the like.

The compounds of the present invention can be in the form of a pharmaceutically acceptable salt, a pharmaceutically acceptable solvate, or a pharmaceutically acceptable solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, e.g. groups which can be protonated, can be present in salt form, and can be used according to the invention in the form of their addition salts with inorganic or organic acids. Examples of suitable acids include hydrogen chloride, hydrogen bromide, hydrogen iodide, phosphoric acid, sulfuric acid, nitric acid, methanesulfonic acid, p-toluenesulfonic acid, naphthalenedisulfonic acids, sulfoacetic acid, trifluoroacetic acid, oxalic acid, acetic acid, tartaric acid, lactic acid, salicylic acid, benzoic acid, carbonic acid, formic acid, propionic acid, pivalic acid, diethylacetic acid, malonic acid, succinic acid, pimelic acid, fumaric acid, malonic acid, maleic acid, malic acid, embonic acid, mandelic acid, sulfaminic acid, phenylpropionic acid, gluconic acid, ascorbic acid, isonicotinic acid, citric acid, adipic acid, taurocholic acid, glutaric acid, stearic acid, glutamic acid or aspartic acid, and other acids known to the person skilled in the art. The salts which are formed are, inter alia, hydrochlorides, chlorides, hydrobromides, bromides, iodides, sulfates, phosphates, methanesulfonates (mesylates), tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Therefore, the following items are also in accordance with the invention:

(a) all stereoisomers or tautomers of the compounds, including mixtures thereof in all ratios,
(b) prodrugs of the compounds, or stereoisomers or tautomers of these prodrugs,
(c) pharmaceutically acceptable salts of the compounds and of the items mentioned under (a) and (b),
(d) pharmaceutically acceptable solvates of the compounds and of the items mentioned under (a), (b) and (c).

It should be understood that all references to compounds above and below are meant to include these items, in particular pharmaceutically acceptable solvates of the compounds, or pharmaceutically acceptable solvates of their pharmaceutically acceptable salts.

Furthermore, the present invention relates to pharmaceutical compositions comprising at least one compound of formula (I) wherein $R^1$ and $R^2$ are defined as hereinabove, or its derivatives, prodrugs, solvates, tautomers or stereoisomers thereof as well as the physiologically acceptable salts of each of the foregoing, including mixtures thereof in all ratios, as active ingredient, together with a pharmaceutically acceptable carrier.

For the purpose of the present invention the term "pharmaceutical composition" refers to a composition or product comprising one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

A pharmaceutical composition of the present invention may additionally comprise one or more other compounds as active ingredients (drugs), such as one or more additional compounds of the present invention. In a particular embodiment the pharmaceutical composition further comprises a second active ingredient or its derivatives, prodrugs, solvates, tautomers or stereoisomers thereof as well as the physiologically acceptable salts of each of the foregoing, including mixtures thereof in all ratios, wherein that second active ingredient is other than a compound of formula (I) wherein $R^1$ and $R^2$ are defined as hereinabove; preferably, that second active ingredient is a compound that is useful in the in the treatment, prevention, suppression and/or amelioration of medicinal conditions or pathologies for which the compounds of the present invention are useful as well and which are listed elsewhere hereinbefore or hereinafter. Such combination of two or more active ingredients or drugs may be safer or more effective than either drug or active ingredient alone, or the combination is safer or more effective than would it be expected based on the additive properties of the individual drugs. Such other drug(s) may be administered, by a route and in an amount commonly used contemporaneously or sequentially with a compound of the invention. When a compound of the invention is used contemporaneously with one or more other drugs or active ingredients, a combination product containing such other drug(s) and the compound of the invention—also referred to as "fixed dose combination"—is preferred. However, combination therapy also includes therapies in which the compound of the present invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

Examples of other active substances (ingredients, drugs) that may be administered in combination with a compound of the invention, and either administered separately or in the same pharmaceutical composition, include, but are not limited to the compounds classes and specific compounds listed in the following: Glucocorticoides, methyl prednisolone, beta interferones, glatirameracetate, immunoglobulines, natalizumab, fingolimod, mitoxantrone, azathioprine, cyclophosphamide, dimethylfumarate.

In another aspect of the invention, a pharmaceutical composition comprising a therapeutically effective amount of at least one compound of the invention is provided.

In a preferred embodiment, the pharmaceutical composition contains at least one additional compound selected from the group consisting of physiologically acceptable excipients, auxiliaries, adjuvants, diluents, carriers and/or additional pharmaceutically active substance other than the compounds of the invention.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

In another aspect of the invention, a set or kit is provided comprising a therapeutically effective amount of at least one compound of the invention and/or at least one pharmaceutical composition as described herein and a therapeutically effective amount of at least one further pharmacologically active substance other than the compounds of the invention. It is preferred that this set or kit comprises separate packs of a) an effective amount of a compound of formula (I) wherein $R^1$ and $R^2$ are defined as hereinabove, or its derivatives, prodrugs, solvates, tautomers or stereoisomers thereof as well as the physiologically acceptable salts of each of the foregoing, including mixtures thereof in all ratios, and b) an effective amount of a further active ingredient that further active ingredient not being a compound of formula (I) wherein $R^1$ and $R^2$ are defined as hereinabove.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

Tablets: mixing of active ingredient/s and auxiliaries, compression of said mixture into tablets (direct compression), optionally granulation of part of mixture before compression.

Capsules: mixing of active ingredient/s and auxiliaries to obtain a flowable powder, optionally granulating powder, filling powders/granulate into opened capsules, capping of capsules.

Semi-solids (ointments, gels, creams): dissolving/dispersing active ingredient/s in an aqueous or fatty carrier; subsequent mixing of aqueous/fatty phase with complementary fatty/aqueous phase, homogenization (creams only).

Suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

Aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound of the invention and optionally one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds of the invention or of their pharmaceutically acceptable salts. Suitable pharmaceutically acceptable salts of the compounds of this invention are those described hereinbefore and include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds of the invention is known to the skilled artisan or can be easily determined by standard methods known in the art.

The compounds of the present invention and the optional additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The specific dose for the individual patient, in particular for the individual human patient, depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

The compounds of the present invention exhibit pharmacological activity at the retinoid-related orphan receptor γ. They inhibit retinoid-related orphan receptor γ1 as well as retinoid-related orphan receptor γ2 and are therefore useful for the treatment, prevention, suppression and/or amelioration of medicinal conditions or pathologies that are affected by ROR γ activity. As ROR γ1 and in particular ROR γ2 are important regulators of several diverse immune functions, the compounds of the present invention are particularly useful for the treatment, prevention, suppression and/or amelioration of autoimmune diseases, such as rheumatoid arthritis, collagen-induced arthritis (CIA), ankylosing spondylitis, systemic lupus erythematodus (SLE), psoriasis, atopic eczema, inflammatory bowel disease (IBD), Crohn's disease, multiples sclerosis (MS), ulcerative colitis, asthma, amyotrophic lateral sclerosis (ALS), autoimmune hepatitis. They are particular useful for prevention and especially the treatment of MS. They are also useful for preventing and/or treating adipositas, type 1 and type 2 diabetes and insulin resistance.

The compounds of the present invention can be prepared according to the procedures of the following Schemes and Examples, using appropriate materials, and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The starting materials for the preparation of compounds of the present invention can prepared by methods as described in the examples or by methods known per se, as described in the literature of synthetic organic chemistry and known to the skilled artisan, or can be obtained commercially.

The present invention also refers to a process for manufacturing a compound according to formula (I), or derivatives, prodrugs, solvates, tautomers or stereoisomers thereof as well as the physiologically acceptable salts of each of the foregoing, the process being characterized in that
(a) a primary amine $R^1$—$NH_2$ and an aldehyde $R^2$—CHO are mixed; and
(b) toluene-4-sulfonic acid 2-isocyano-ethyl ester and a azide anion ($N_3^-$) source are added to the mixture resulted in step (a);
wherein $R^1$ and $R^2$ are defined as hereinabove and hereinafter; however, with the proviso that the manufacturing of 7-benzyl-8-(4-methoxyphenyl)-5,6,7,8-tetrahydro-tetrazolo[1,5-a]pyrazine according to this process is not claimed as being part of the invention.

The process according to the present invention can be performed by applying reaction conditions and work-up procedures and using solvents and reagents similar to those described in M. Umkehrer et al., Tetrahedron Lett. 45 (2004) 6421. The process is a one-pot synthesis and believed to proceed via a so-called 4 component Ugi reaction. Scheme 1 depicts the presumed reaction mechanism of the process according to the invention:

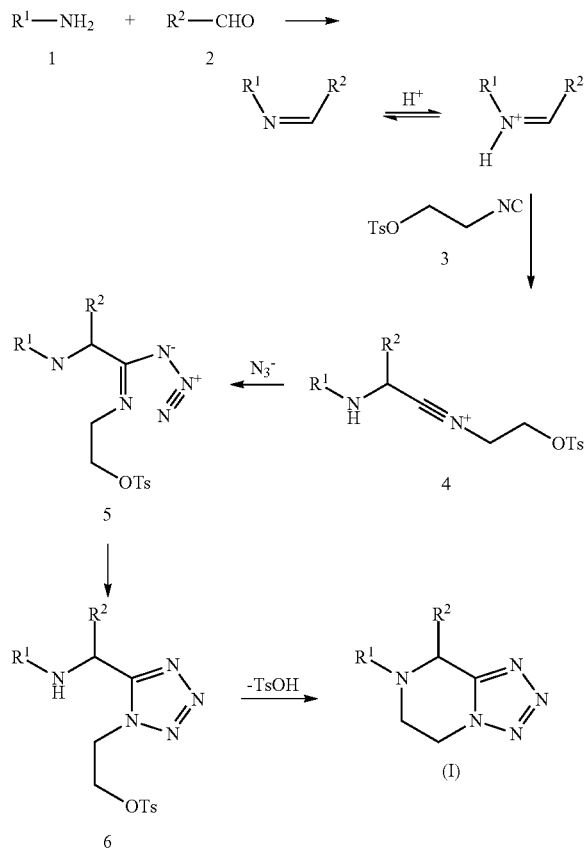

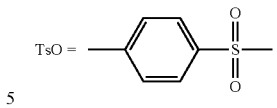

Preferably, the azide anion source is trimethylsilylazide. Furthermore, the four component reaction is preferably performed in an inert solvent, such as alcohol, e.g. methanol, ethanol or 2-propanol or mixtures thereof, at reaction temperatures ranging from 0° C. to 40° C., more preferably 10° C. to 30° C., especially at room temperature, in a reaction period of 2 hours to 48 hours, more preferably 6 hours to 24 hours, especially 12 to 18 hours.

Formation of toluene-4-sulfonic acid 2-isocyano-ethyl ester (3) is schematically depicted in Scheme 2:

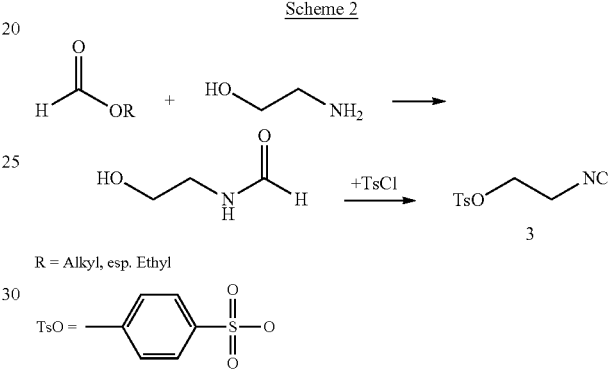

Alkylformate, preferably ethyl formate is reacted with 2-aminoethanol to yield N-(2-hydroxyethyl)-formamide, which is—either after isolation or directly—subsequently reacted with p-toluenesulphonyl chloride in order to obtain toluene-4-sulfonic acid 2-isocyano-ethyl ester (3). The formamide formation is preferably performed using the alkyl formate as both reactant and solvent at temperatures between 0° C. and room temperature; the subsequent reaction with tosyl chloride is usually performed in pyridine at a temperature in the range of −30° C. to 0° C., preferably at about −10° C. for about 2 to 10 hours, preferably about 6 hours, and yields toluene-4-sulfonic acid 2-isocyano-ethyl ester (3) as a solid crystal.

Compounds of formula (I) in which $R^1$ denotes —(C═O)—$R^3$ can also be obtained via the synthetic route depicted in Scheme 3 below:

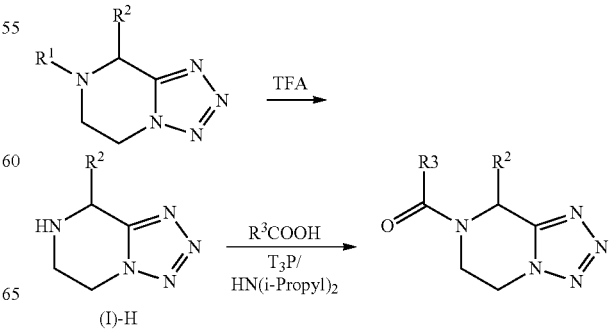

$R^1 =$ 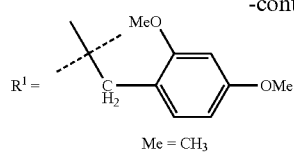

The tetraazolopyrazine bearing the 2,4-methoxybenzyl substituent obtained via the synthetic route depicted in Scheme 1 hereinabove is converted into the tetraazolopyrazine of formula (I)-H using trifluoroacetic acid (TFA); (I)-H then in turn is reacted with the carboxylic acid $R^3$—COOH wherein $R^3$ is as defined for formula (I) herein in a $T_3P$ mediated coupling reaction.

The compounds of the present invention obtained by the synthetic methods described hereinabove and hereinafter are generally isolated as such, e.g. as the free base or acid, as the case may be, or in the form of their pharmaceutically acceptable salts, such as those described hereinabove. The compounds of the present invention and prepared according to the synthetic method described and exemplified hereinabove and hereinafter can be isolated from the reaction mixture by usual work-up procedures, such as concentrating the crude reaction mixture, taking it up in an organic solvent, washing and/or neutralizing with an appropriate reagent like aqueous sodium hydrogencarbonate, sodium carbonate, sodium hydroxide, potassium hydroxide, ammonium chloride, hydrogen chloride, sodium chloride, drying of the organic phases over a suitable drying agent such as sodium sulfate, and removing of the organic solvent(s) by evaporation. The product so obtained may further be purified by standard methods like liquid column chromatography, vacuum distillation and/or recrystallization from an appropriate solvent or solvent mixture; it may also be converted into one of its pharmaceutically acceptable salts as described herein.

EXPERIMENTAL SECTION

Abbreviations

Some abbreviations that may appear in this application are as follows in Table 1:

TABLE 1

| Abbreviation | Meaning |
| --- | --- |
| $^1$HNMR | Proton Nuclear Magnetic Resonance |
| ACN | Acetonitrile |
| aq. | aqueous |
| CDCl$_3$ | Deuterochloroform |
| d | Doublet |
| dd | Double doublet |
| DMSO-d6 | Hexadeutero-dimethylsulfoxide |
| dt | Double triplet |
| FBS | Fetal bovine serum |
| h | hour(s) |
| HPLC | High Performance Liquid Chromatography |
| J | Coupling constant |
| LCMS | Liquid Chromatography coupled to Mass Spectrometry |
| m | Multiplet |
| min | Minute |
| mL | Milliliter |
| n.d. | not determined |
| rH | Relative humidity |
| RT | Room Temperature |
| RT. | Retention time |
| s | Singulet |

TABLE 1-continued

| Abbreviation | Meaning |
| --- | --- |
| SFC | Supercritical Fluid Chromatography |
| t | Triplet |
| T$_3$P | 2,4,6-Tripropyl-1,3,5,2,4,6-trioxatriphosphorinane-2,4,6-trioxide (1-Propanephosphonic anhydride) |
| TFA | Trifluoroacetic acid |
| TLC | Thin Layer Chromatography |

The compounds of the present invention can be prepared according to the procedures of the following Schemes and Examples, using appropriate materials and are further exemplified by the following specific examples.

The invention will be illustrated, but not limited, by reference to the specific embodiments described in the following examples. Unless otherwise indicated in the schemes, the variables have the same meaning as described above.

Unless otherwise specified, all starting materials are obtained from commercial suppliers and used without further purifications. Unless otherwise specified, all temperatures are expressed in ° C. and all reactions are conducted at RT. Compounds were purified by either silica chromatography or preparative HPLC.

LCMS-Analysis:
Method A
Method: A: 0.1% TFA in H$_2$O, B: 0.1% TFA in ACN: Flow: 2.0 mL/min.
Column: XBridge C8 (50×4.6 mm, 3.5 μm+ve mode)
Method B
Method: A: 10 mM NH$_4$HCO$_3$ in H$_2$O, B: ACN: Flow: 1 mL/min.
Column: XBridge C8 (50×4.6 mm, 3.5 μm+ve mode)
$^1$HNMR:
Bruker 400 MHz
HPLC:
Method A
Method: A: 0.1% TFA in H$_2$O, B: 0.1% TFA in ACN: Flow: 2.0 mL/min.
Column: XBridge C8 (50×4.6 mm, 3.5 μm).
Method B
Method: A 10 mM NH$_4$HCO$_3$ in H$_2$O, B: ACN: Flow 1 mL/min.
Column: XBridge C8 (50×4.6 mm, 3.5 μm+ve mode)

Preparation of Tetrahydro-Tetrazolo-Pyridines of Formula (I)

Step 1: N-(2-Hydroxy-ethyl)-formamide

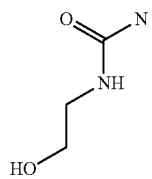

Procedure: Ethyl formate (150 mL) is added to 2-aminoethanol (50 g, 820 mmol) at 10° C. and stirred for 12 h at RT. The reaction mixture is concentrated and dried under high vacuum to get the product.
Yield: 65 g, 100%.
Color: Brown oil.

¹H NMR (400 MHz, DMSO-d6): δ 7.99 (s, 1H), 4.72 (br s, 1H), 3.40-3.32 (m, 2H), 3.15-3.08 (m, 2H).

Step 2: Toluene-4-sulfonic acid 2-isocyano-ethyl ester

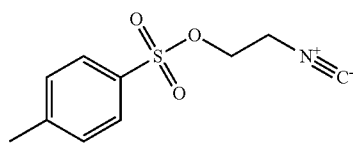

Procedure: To a stirring solution of p-toluenesulphonyl chloride (63 g, 1415 mmol) in anhydrous pyridine (100 mL), N-(2-hydroxy-ethyl)-formamide (15 g, 707 mmol) in anhydrous pyridine (50 ml) is added and stirred at −10° C. for 6 h. After completion of the reaction (monitored by TLC), the reaction mixture is poured into crushed ice, extracted with diethyl ether:hexane (5:1) (5×150 mL), washed with water (5×150 mL), brine (1×150 mL), dried over anhydrous Na₂SO₄, concentrated under vacuum. The residue is dissolved in diethylether: hexane (5:1, 60 mL) and cooled to −15° C., the solid crystallized is filtered, washed with cold hexane to get the product.

Yield: 10 g, 27%.
Color: Brown crystalline solid.

Compound 1: 7-(2,5-Dimethoxy-benzyl)-8-(4-isopropoxy-phenyl)-5,6,7,8-tetrahydro-tetrazolo[1,5-a]pyrazine

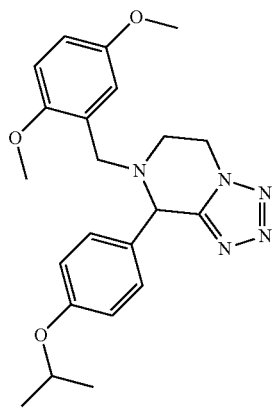 [SMILES: COc1ccc(OC)c(CN2CCn3nnnc3C2c2ccc(OC(C)C)cc2)c1]

Procedure: To a solution of 4-isopropoxybenzaldehyde (200 mg, 1.22 mmol) in dry methanol (4 mL), 2,5-dimethoxybenzylamine (203.7 mg, 361 mmol) is added and allowed to stir for 4 h at RT. Trimethylsilylazide (0.1 ml, 0.8 mmol) and toluene-4-sulfonic acid 2-isocyano-ethyl ester (181 mg, 0.8 mmol) are added and the reaction mixture is allowed to stir for 16 h. The completion of the reaction is monitored by the TLC and LCMS, the reaction mixture is concentrated and the residue is taken in dichloromethane (5 mL), washed with saturated aq. NaHCO₃ (5 mL), dried over anhydrous Na₂SO₄ and concentrated. The crude product is purified by the Isolera flash column chromatography to afford the product.

Yield: 196 mg, 39%.
Color: Yellow gum.

LCMS: (Method A) 410.2 (M+1), RT. 4.5 min, 99.2% (Max), 99.0% (220 nm).
¹H NMR (400 MHz, CDCl₃): δ 7.33-7.31 (m, 2H), 7.18 (d, J=8.2 Hz, 1H), 6.89 (dd, J=2.0, 6.8 Hz, 2H), 6.49-6.44 (m, 2H), 4.91 (s, 1H), 4.58-4.49 (m, 2H), 4.42-4.39 (m, 1H), 3.81 (s, 3H), 3.77 (s, 3H), 3.76-3.74 (m, 1H), 3.57-3.54 (m, 1H), 3.43-3.37 (m, 1H), 2.89-2.82 (m, 1H), 1.34 (d, J=6.0 Hz, 6H).
HPLC: (Method A) RT. 4.5 min, 99.2% (Max), 98.8% (254 nm).

Compound 2: 7-(2-Fluoro-benzyl)-8-(4-isopropoxy-phenyl)-5,6,7,8-tetrahydro-tetrazolo[1,5-a]pyrazine

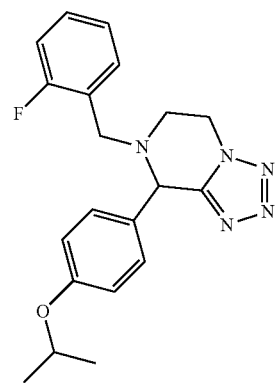 [SMILES: CC(C)Oc1ccc(C2c3nnnn3CCN2Cc2ccccc2F)cc1]

It is synthesized using the procedure as described for Compound 1 above utilizing 4-isopropoxybenzaldehyde and 2-fluorobenzylamine.

Yield: 63 mg, 14%.
Color: Off white solid.
LCMS: (Method A) 368.3 (M+1), RT. 5.2 min, 99.2% (Max), 99.0% (220 nm).
¹H NMR (400 MHz, DMSO-d6): δ 7.44-7.40 (m, 1H), 7.35-7.27 (m, 3H), 7.20-7.13 (m, 2H), 6.91 (d, J=8.6 Hz, 2H), 5.06 (s, 1H), 4.61-4.53 (m, 2H), 4.48-4.42 (m, 1H), 3.69-3.66 (m, 1H), 3.61-3.58 (m, 1H), 3.19-3.14 (m, 1H), 2.95-2.89 (m, 1H), 1.25 (d, J=6.0 Hz, 6H).
HPLC: (Method A) RT. 4.5 min, 99.8% (Max), 99.8% (220 nm).

Compound 3: 7-Cyclohexylmethyl-8-(4-isopropoxy-phenyl)-5,6,7,8-tetra hydro-tetrazolo[1,5-a]pyrazine

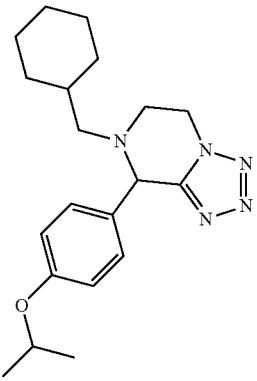 [SMILES: CC(C)Oc1ccc(C2c3nnnn3CCN2CC2CCCCC2)cc1]

It is synthesized using the procedure as described for Compound 1 utilizing 4-isopropoxybenzaldehyde and cyclohexylmethylamine.

Yield: 116 mg, 27%.

Color: Off white solid.

LCMS: (Method A) 355.2 (M+1), RT. 5.7 min, 98.4% (Max), 97.7% (220 nm).

$^1$H NMR (400 MHz, DMSO-d6): δ 7.16 (d, J=8.7 Hz, 2H), 6.87 (d, J=8.7 Hz, 2H), 4.84 (s, 1H), 4.62-4.53 (m, 2H), 4.49-4.42 (m, 1H), 3.31-3.29 (m, 1H), 2.85-2.78 (m, 1H), 2.21-2.19 (m, 2H), 1.80-1.77 (m, 1H), 1.59-1.53 (m, 5H), 1.25 (d, J=6.0 Hz, 6H), 1.19-1.01 (m, 3H), 0.73-0.70 (m, 1H), 0.54-0.51 (m, 1H).

HPLC: (Method A) RT. 5.6 min, 99.5% (Max), 99.2% (220 nm).

Compound 4: 7-(2-Fluoro-benzyl)-8-(4-methoxy-phenyl)-5,6,7,8-tetrahydro-tetrazolo[1,5-a]pyrazine

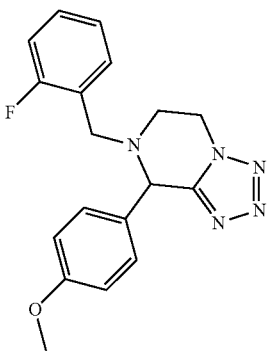 [SMILES: COc1ccc(C2c3nnnn3CCN2Cc2ccccc2F)cc1]

It is synthesized using the procedure as described for Compound 1 utilizing 4-methoxybenzaldehyde and 2-fluorobenzylamine.

Yield: 100 mg, 20%.

Color: white solid.

LCMS: (Method A) 340.3 (M+1), RT. 5.2 min, 99.7% (Max), 99.7% (220 nm).

$^1$H NMR (400 MHz, DMSO-d6): δ 7.44-7.40 (m, 1H), 7.35-7.30 (m, 3H), 7.20-7.13 (m, 2H), 6.96-6.92 (m, 2H), 5.07 (s, 1H), 4.58-4.53 (m, 1H), 4.49-4.42 (m, 1H), 3.69-3.65 (m, 1H), 3.61-3.58 (m, 1H), 3.19-3.14 (m, 1H), 2.95-2.88 (m, 1H).

HPLC: (Method A) RT. 4.6 min, 99.8% (Max), 99.8% (220 nm).

Compound 5: 7-(3-Isopropyl-1-phenyl-1H-pyrazol-4-ylmethyl)-8-(4-methoxy-phenyl)-5,6,7,8-tetrahydro-tetrazolo[1,5-a]pyrazine

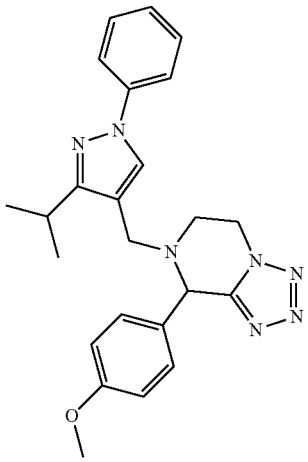 [SMILES: COc1ccc(C2c3nnnn3CCN2Cc2cn(-c3ccccc3)nc2C(C)C)cc1]

It is synthesized using the procedure as described for Compound 1 utilizing 4-methoxybenzaldehyde and (3-isopropyl-1-phenyl-1H-pyrazol-4-yl)-methylamine.

Yield: 34 mg, 5%.

Color: Off white solid.

LCMS: (Method A) 430.2 (M+1), RT. 5.3 min, 99.6% (Max), 99.6% (254 nm).

$^1$H NMR (400 MHz, DMSO-d6): δ 8.36 (s, 1H), 7.77 (dd, J=1.1, 8.6 Hz, 2H), 7.46-7.42 (m, 2H), 7.30 (dd, J=1.9, 6.8 Hz, 2H), 7.25-7.21 (m, 1H), 6.97-6.94 (m, 2H), 5.05 (s, 1H), 4.59-4.54 (m, 1H), 4.47-4.41 (m, 1H), 3.76 (s, 3H), 3.60-3.56 (m, 1H), 3.38-3.35 (m, 1H), 3.32-3.25 (m, 1H), 2.91-2.79 (m, 2H), 1.17 (d, J=6.88 Hz, 3H), 1.1 (d, J=6.9 Hz, 3H).

HPLC: (Method A) RT. 5.3 min, 97.9% (Max), 99.3% (254 nm).

Compound 6: 7-(3-Bromo-benzyl)-8-(3-bromo-phenyl)-5,6,7,8-tetrahydro-tetrazolo[1,5-a]pyrazine

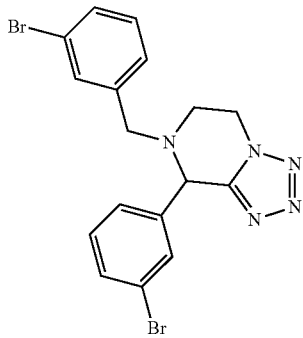 [SMILES: Brc1cccc(CN2CCn3nnnc3C2c2cccc(Br)c2)c1]

It is synthesized using the procedure as described for Compound 1 utilizing 3-bromobenzaldehyde and 3-bromobenzylamine.

Yield: 104 mg, 21%.

Color: white solid.

LCMS: (Method A) 450.0 (M+1), RT. 5.5 min, 97.0% (Max), 97.1% (220 nm).

¹H NMR (400 MHz, DMSO-d6): δ 7.67 (s, 1H), 7.58-7.56 (m, 1H), 7.49-7.45 (m, 3H), 7.39-7.35 (m, 1H), 7.33-7.27 (m, 2H), 5.18 (s, 1H), 4.59-4.46 (m, 2H), 3.71-3.67 (m, 1H), 3.55-3.52 (m, 1H), 3.18-3.12 (m, 1H), 2.96-2.89 (m, 1H)

HPLC: (Method A) RT. 5.7 min, 94.9% (Max), 94.8% (220 nm).

Compound 7: 8-(3-Bromo-phenyl)-7-thiophen-2-ylmethyl-5,6,7,8-tetrahydro-tetrazolo[1,5-a]pyrazine

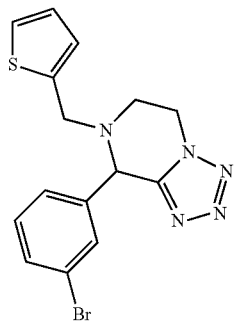 [SMILES: Brc1cccc(C2c3nnnn3CCN2Cc2cccs2)c1]

It is synthesized using the procedure as described for Compound 1 utilizing 3-bromobenzaldehyde and thiophen-2-ylmethylamine.

Yield: 91 mg, 22%.
Color: Pale yellow solid.
LCMS: (Method A) 376.0 (M+1), RT. 5.1 min, 96.7% (Max), 96.9% (220 nm).

¹H NMR (400 MHz, DMSO-d6): δ 7.66 (s, 1H), 7.58 (d, J=8.0 Hz, 1H), 7.48-7.45 (m, 2H), 7.41-7.37 (m, 1H), 7.01-6.98 (m, 2H), 5.20 (s, 1H), 4.60-4.56 (m, 1H), 4.50-4.43 (m, 1H), 3.84 (s, 2H), 3.29-3.21 (m, 1H), 3.03-2.97 (m, 1H).

HPLC: (Method A) RT 4.9 min, 97.4% (Max), 96.4% (254 nm).

Compound 8: 8-(3-Bromo-phenyl)-7-(3-isopropyl-1-phenyl-1H-pyrazol-4-ylmethyl)-5,6,7,8-tetrahydro-tetrazolo[1,5-a]pyrazine

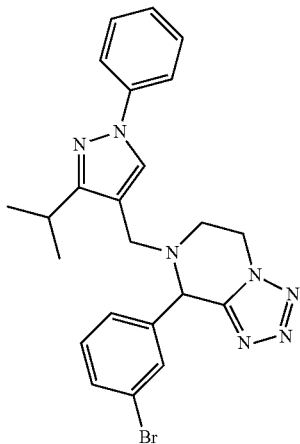 [SMILES: CC(C)c1nn(-c2ccccc2)cc1CN1CCn2nnnc2C1c1cccc(Br)c1]

It is synthesized using the procedure as described for Compound 1 utilizing 3-bromobenzaldehyde and (3-isopropyl-1-phenyl-1H-pyrazol-4-yl)-methylamine.

Yield: 135 mg, 26%.
Color: Off white solid.
LCMS: (Method A) 478.0 (M+1), RT. 5.8 min, 95.2% (Max), 96.1% (254 nm).

¹H NMR (400 MHz, DMSO-d6): δ 8.39 (s, 1H), 7.76 (d, J=8.4 Hz, 2H), 7.64 (s, 1H), 7.59 (d, J=7.9 Hz, 1H), 7.49-7.43 (m, 3H), 7.41-7.37 (m, 1H), 7.23 (t, J=7.0 Hz, 1H), 5.14 (s, 1H), 4.60-4.57 (m, 1H), 4.49-4.42 (m, 1H), 3.58-3.55 (m, 1H), 3.41-3.37 (m, 1H), 3.29-3.27 (m, 1H), 2.92-2.79 (m, 2H), 1.21 (d, J=6.8 Hz, 3H), 1.1 (d, J=6.9 Hz, 3H).

HPLC: (Method A) RT. 5.8 min, 95.6% (Max), 96.3% (254 nm).

Compound 9: 8-(3-Bromo-phenyl)-7-cyclohexylmethyl-5,6,7,8-tetrahydro-tetrazolo[1,5-a]pyrazine

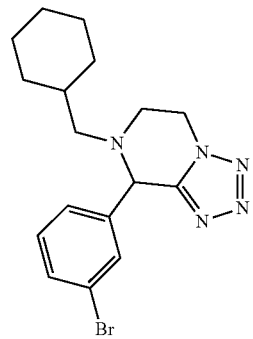 [SMILES: Brc1cccc(C2c3nnnn3CCN2CC2CCCCC2)c1]

It is synthesized using the procedure as described for Compound 1 utilizing 3-bromobenzaldehyde and cyclohexylmethylamine.

Yield: 33 mg, 8%.
Color: white solid.
LCMS: (Method A) 376.2 (M+1), RT. 5.9 min, 99.7% (Max), 99.6% (220 nm).

¹H NMR (400 MHz, DMSO-d6): δ 7.55-7.53 (m, 2H), 7.38-7.32 (m, 2H), 4.97 (s, 1H), 4.57-4.50 (m, 1H), 4.49-4.47 (m, 1H), 3.39-3.36 (m, 1H), 2.88-2.81 (m, 1H), 2.28-2.15 (m, 2H), 1.84-1.80 (m, 1H), 1.65-1.51 (m, 5H), 1.20-1.05 (m, 3H), 0.74-0.71 (m, 1H), 0.55-0.52 (m, 1H).

HPLC: (Method A) RT 6.0 min, 99.3% (Max), 99.3% (220 nm).

Compound 10: 8-(3-Bromo-phenyl)-7-(2,3-difluoro-benzyl)-5,6,7,8-tetrahydro-tetrazolo[1,5-a]pyrazine

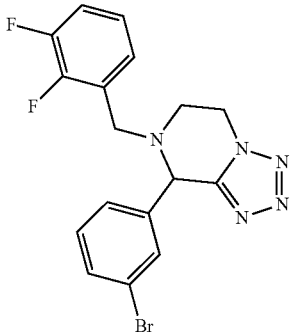 [SMILES: Fc1cccc(CN2CCn3nnnc3C2c2cccc(Br)c2)c1F]

It is synthesized using the procedure as described for Compound 1 utilizing 3-bromobenzaldehyde and 2,3-difluorobenzylamine.

Yield: 64 mg, 14%.
Color: white solid.
LCMS: (Method A) 406.0 (M+1), RT. 5.1 min, 97.6% (Max), 95.9% (220 nm).
$^1$H NMR (400 MHz, DMSO-d6): δ 7.65 (s, 1H), 7.56 (d, J=7.9 Hz, 1H), 7.46 (d, J=7.7 Hz, 1H), 7.38-7.31 (m, 2H), 7.26-7.16 (m, 2H), 5.21 (s, 1H), 4.61-4.56 (m, 1H), 4.52-4.45 (m, 1H), 3.76-3.66 (m, 2H), 3.21-3.18 (m, 1H), 2.99-2.97 (m, 1H).
HPLC: (Method A) RT. 5.3 min, 95.5% (Max), 95.4% (220 nm).

Compound 11: 8-(4-Fluoro-phenyl)-7-(3-isopropyl-1-phenyl-1H-pyrazol-4-ylmethyl)-5,6,7,8-tetrahydro-tetrazolo[1,5-a]pyrazine

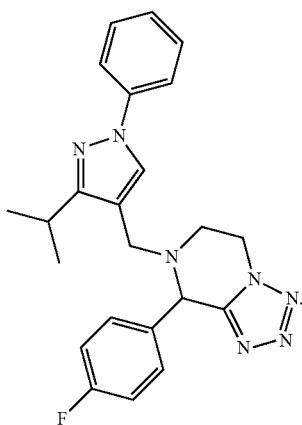 [SMILES: CC(C)c1nn(-c2ccccc2)cc1CN1CCn2nnnc2C1c1ccc(F)cc1]

It is synthesized using the procedure as described for Compound 1 utilizing 4-fluorobenzaldehyde and (3-Isopropyl-1-phenyl-1H-pyrazol-4-yl)-methylamine.

Yield: 52 mg, 7%.
Color: Off white solid.
LCMS: (Method A) 418.2 (M+1), RT. 5.5 min, 99.7% (Max), 99.5% (254 nm).
$^1$H NMR (400 MHz, DMSO-d6): δ 8.38 (s, 1H), 7.77 (dd, J=1.2, 8.7 Hz, 2H), 7.48-7.42 (m, 4H), 7.27-7.21 (m, 3H), 5.14 (s, 1H), 4.60-4.57 (m, 1H), 4.48-4.41 (m, 1H), 3.58-3.55 (m, 1H), 3.41-3.37 (m, 1H), 3.31-3.29 (m, 1H), 2.93-2.87 (m, 1H), 2.84-2.79 (m, 1H), 1.17 (d, J=6.8 Hz, 3H), 1.08 (d, J=6.9 Hz, 3H).
HPLC: (Method A) RT. 5.5 min, 99.5% (Max), 99.2% (254 nm).

Compound 12: 8-(2,5-Dimethoxy-phenyl)-7-(4-isopropoxy-benzyl)-5,6,7,8-tetrahydro-tetrazolo[1,5-a]pyrazine

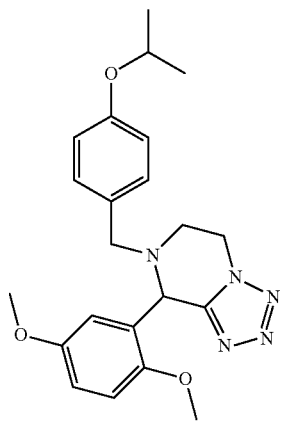 [SMILES: COc1ccc(OC)c(C2c3nnnn3CCN2Cc2ccc(OC(C)C)cc2)c1]

It is synthesized using the procedure as described for Compound 1 utilizing 2,5-dimethoxybenzaldehyde and 4-isopropoxybenzylamine.

Yield: 95 mg, 19%.
Color: White solid.
LCMS: (Method A) 410.3 (M+1), RT. 4.8 min, 98.3% (Max), 97.9% (220 nm).
$^1$H NMR (400 MHz, DMSO-d6): δ 7.13 (d, J=8.5 Hz, 2H), 7.05 (d, J=9.0 Hz, 1H), 6.93-6.90 (m, 1H), 6.85-6.83 (m, 3H), 5.28 (s, 1H), 4.59-4.50 (m, 2H), 4.43-4.36 (m, 1H), 3.74 (s, 3H), 3.66 (s, 3H), 3.64-3.61 (m, 1H), 3.38-3.36 (m, 1H), 3.19-3.15 (m, 1H), 2.85-2.81 (m, 1H), 1.23 (d, J=6.0 Hz, 6H).
HPLC: (Method A) RT. 5.0 min, 99.0% (Max), 98.9% (220 nm).

Compound 13: 8-(2,5-Dimethoxy-phenyl)-7-(3-isopropyl-1-phenyl-1H-pyrazol-4-ylmethyl)-5,6,7,8-tetrahydro-tetrazolo[1,5-a]pyrazine

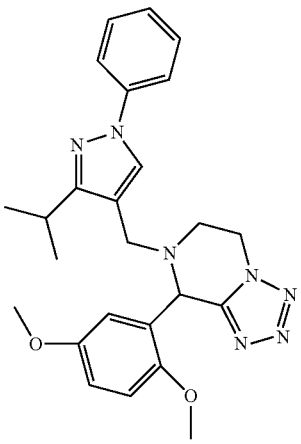 [SMILES: COc1ccc(OC)c(C2c3nnnn3CCN2Cc2cn(-c3ccccc3)nc2C(C)C)c1]

It is synthesized using the procedure as described for Compound 1 utilizing 2,5-dimethoxybenzaldehyde and (3-isopropyl-1-phenyl-1H-pyrazol-4-yl)-methylamine.

Yield: 76 mg, 13%.

Color: Off white solid.

LCMS: (Method A) 460.2 (M+1), RT. 5.3 min, 97.9% (Max), 99.5% (254 nm).

$^1$H NMR (400 MHz, DMSO-d6): δ 8.34 (s, 1H), 7.75 (dd, J=1.1, 8.6 Hz, 2H), 7.44 (dd, J=2.0, 10.8 Hz, 2H), 7.24-7.21 (m, 1H), 7.03 (d, J=9.0 Hz, 1H), 6.93 (dd, J=3.1, 9.0 Hz, 1H), 6.79 (d, J=3.1 Hz, 1H), 5.27 (s, 1H), 4.57-4.53 (m, 1H), 4.43-4.36 (m, 1H), 3.70 (s, 3H), 3.66 (s, 3H), 3.60-3.56 (m, 1H), 3.37-3.33 (m, 1H), 3.26-3.15 (m, 1H), 2.88-2.81 (m, 1H), 2.79-2.74 (m, 1H), 1.2 (d, J=6.6 Hz, 3H), 1.0 (d, J=6.9 Hz, 3H).

HPLC: (Method A) RT. 5.3 min, 97.1% (Max), 98.5% (254 nm).

Compound 14: {4-[7-(2-Fluoro-benzyl)-5,6,7,8-tetrahydro-tetrazolo[1,5-a]pyrazin-8-yl]-phenyl}-dimethyl-amine

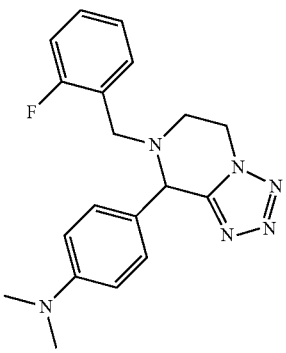 [SMILES: CN(C)c1ccc(C2c3nnnn3CCN2Cc2ccccc2F)cc1]

It is synthesized using the procedure as described for Compound 1 utilizing 4-(N,N-dimethylamino)-benzaldehyde and 2-fluorobenzylamine.

Yield: 92 mg, 21%.

Color: white solid.

LCMS: (Method A) 353.2 (M+1), RT. 3.0 min, 98.8% (Max), 98.0% (220 nm).

$^1$H NMR (400 MHz, DMSO-d6): δ 7.44-7.40 (m, 1H), 7.34-7.29 (m, 1H), 7.20-7.13 (m, 4H), 6.70 (d, J=8.7 Hz, 2H), 4.98 (s, 1H), 4.55-4.51 (m, 1H), 4.48-4.43 (m, 1H), 3.70-3.66 (m, 1H), 3.60-3.56 (m, 1H), 3.18-3.13 (m, 1H), 2.92-2.85 (m, 7H).

HPLC: (Method A) RT. 3.0 min, 99.0% (Max), 97.2% (254 nm).

Compound 15: [4-(7-Benzo[1,3]dioxol-5-ylmethyl-5,6,7,8-tetrahydro-tetrazolo[1,5-a]pyrazin-8-yl)-phenyl]-dimethyl-amine

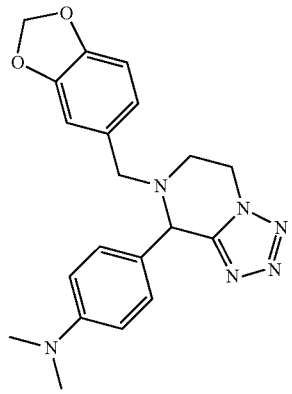 [SMILES: CN(C)c1ccc(C2c3nnnn3CCN2Cc2ccc3c(c2)OCO3)cc1]

It is synthesized using the procedure as described for Compound 1 utilizing 4-(N,N-dimethylamino)-benzaldehyde and benzo[1,3]dioxol-5-ylmethylamine.

Yield: 35 mg, 7%.

Color: Pale yellow solid.

LCMS: (Method A) 379.2 (M+1), RT. 2.9 min, 99.2% (Max), 99.5% (220 nm).

$^1$H NMR (400 MHz, DMSO-d6): δ 7.16 (d, J=8.8 Hz, 2H), 6.85-6.83 (m, 2H), 6.75-6.70 (m, 3H), 5.97 (s, 2H), 4.91 (s, 1H), 4.53-4.49 (m, 1H), 4.45-4.41 (m, 1H), 3.62-3.59 (m, 1H), 3.33-3.29 (m, 1H), 3.16-3.12 (m, 1H), 2.89 (s, 6H), 2.84-2.81 (m, 1H).

HPLC: (Method A) RT. 2.9 min, 98.6% (Max), 98.6% (220 nm).

Compound 16: {4-[7-(2,5-Difluoro-benzyl)-5,6,7,8-tetrahydro-tetrazolo[1,5-a]pyrazin-8-yl]-phenyl}-dimethyl-amine

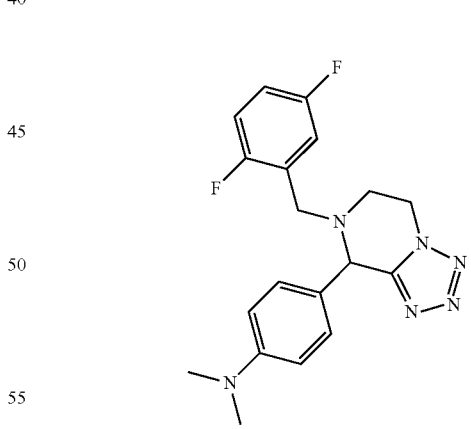

It is synthesized using the procedure as described for Compound 1 utilizing 4-(N,N-dimethylamino)-benzaldehyde and 2,5-difluorobenzylamine.

Yield: 40 mg, 9%.

Color: white solid.

LCMS: (Method A) 371.2 (M+1), RT. 3.1 min, 93.3% (Max), 93.3% (220 nm).

$^1$H NMR (400 MHz, DMSO-d6): δ 7.28-7.12 (m, 5H), 6.69 (d, J=8.8 Hz, 2H), 5.01 (s, 1H), 4.54-4.51 (m, 2H), 3.71-3.59 (m, 2H), 3.18-3.15 (m, 1H), 2.92-2.88 (m, 7H).

HPLC: (Method A) RT. 3.1 min, 96.9% (Max), 96.7% (220 nm).

Compound 17: {4-[7-(3-Fluoro-benzyl)-5,6,7,8-tetrahydro-tetrazolo[1,5-a]pyrazin-8-yl]-phenyl}-dimethyl-amine

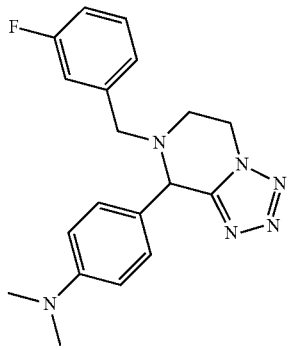 [SMILES: CN(C)c1ccc(C2c3nnnn3CCN2Cc2cccc(F)c2)cc1]

It is synthesized using the procedure as described for Compound 1 utilizing 4-(N,N-dimethylamino)-benzaldehyde and 3-fluorobenzylamine.

Yield: 129 mg, 30%.
Color: Pale yellow solid.
LCMS: (Method A) 353.3 (M+1), RT. 6.3 min, 99.0% (Max), 99.4% (254 nm).
$^1$H NMR (400 MHz, CDCl3): δ 7.42-7.29 (m, 3H), 7.08-6.97 (m, 4H), 6.95-6.60 (m, 1H), 4.86 (s, 1H), 4.55-4.51 (m, 1H), 4.47-4.41 (m, 1H), 3.96-3.93 (m, 1H), 3.40-3.32 (m, 2H), 2.93-3.07 (m, 5H), 2.89-2.82 (m, 2H).
HPLC: (Method A) RT. 6.3 min, 99.3% (Max), 99.4% (254 nm).

Compound 18: {4-[7-(3-Isopropyl-1-phenyl-1H-pyrazol-4-ylmethyl)-5,6,7,8-tetrahydro-tetrazolo[1,5-a]pyrazin-8-yl]-phenyl}-dimethyl-amine

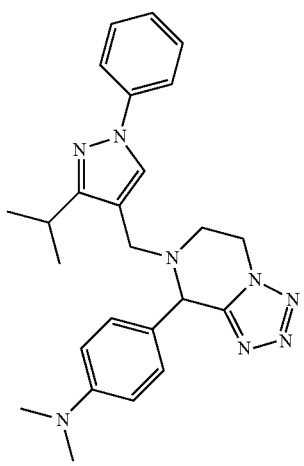 [SMILES: CC(C)c1nn(-c2ccccc2)cc1CN1CCn2nnnc2C1c1ccc(N(C)C)cc1]

It is synthesized using the procedure as described for Compound 1 utilizing 4-(N,N-dimethylamino)-benzaldehyde and (3-isopropyl-1-phenyl-1H-pyrazol-4-yl)-methylamine.

Yield: 138 mg, 23%.
Color: Pale yellow solid.
LCMS: (Method A) 443.2 (M+1), RT. 3.9 min, 97.3% (Max), 95.6% (254 nm).
$^1$H NMR (400 MHz, DMSO-d6): δ 8.34 (s, 1H), 7.76 (dd, J=1.1, 8.7 Hz, 2H), 7.44 (dt, J=1.9, 6.9 Hz, 2H), 7.22 (t, J=7.4 Hz, 1H), 7.14 (d, J=8.8 Hz, 2H), 6.71 (d, J=8.8 Hz, 2H), 4.96 (s, 1H), 4.57-4.52 (m, 1H), 4.46-4.40 (m, 1H), 3.61-3.58 (m, 1H), 3.35-3.45 (m, 1H), 3.28-3.24 (m, 1H), 2.89 (s, 6H), 2.85-2.81 (m, 2H), 1.17 (d, J=6.9 Hz, 3H), 1.1 (d, J=6.9 Hz, 3H).
HPLC: (Method A) RT. 3.9 min, 97.5% (Max), 95.8% (254 nm).

Compound 19: [4-(7-Cyclohexylmethyl-5,6,7,8-tetrahydro-tetrazolo[1,5-a]pyrazin-8-yl)-phenyl]-dimethyl-amine

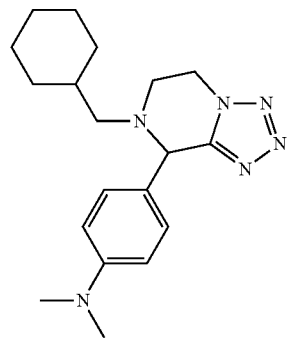 [SMILES: CN(C)c1ccc(C2c3nnnn3CCN2CC2CCCCC2)cc1]

It is synthesized using the procedure as described for Compound 1 utilizing 4-(N,N-dimethylamino)-benzaldehyde and cyclohexylmethylamine.

Yield: 52.42 mg, 12.6%.
Color: Off white solid
LCMS: (Method A) 341.2 (M+1), RT. 3.6 min, 97.56% (Max), 97.68% (220 nm).
$^1$H NMR (400 MHz, DMSO-d6): δ 7.06-7.03 (m, 2H), 6.69-6.65 (m, 2H), 4.76 (s, 1H), 4.57-4.52 (m, 1H), 4.48-4.42 (m, 1H), 3.29-3.32 (m, 1H), 2.88 (s, 6H), 2.82-2.75 (m, 1H), 2.26-2.15 (m, 2H), 1.82-1.79 (m, 1H), 1.60-1.55 (m, 5H), 1.23-0.99 (m, 3H), 0.75-0.67 (m, 1H), 0.58-0.50 (m, 1H).
HPLC: (Method A) RT. 3.65 min, 98.4% (Max), 97.9% (254 nm).

Compound 20: {4-[7-(2,3-Difluoro-benzyl)-5,6,7,8-tetrahydro-tetrazolo[1,5-a]pyrazin-8-yl]-phenyl}-dimethyl-amine

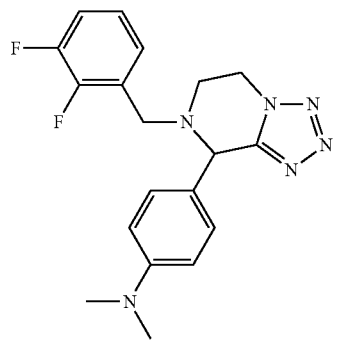 [SMILES: CN(C)c1ccc(C2c3nnnn3CCN2Cc2cccc(F)c2F)cc1]

It is synthesized using the procedure as described for Compound 1 utilizing 4-(N,N-dimethylamino)-benzaldehyde and 2,3-difluorobenzylamine.

Yield: 105.73 mg, 230.3%.

Color: White solid

LCMS: (Method A) 371.2 (M+1), RT. 3.14 min, 97.79% (Max), 98.02% (220 nm).

¹H NMR (400 MHz, DMSO-d6): δ 7.36-7.29 (m, 1H), 7.26-7.23 (m, 1H), 7.21-7.14 (m, 3H), 6.72-6.68 (m, 2H), 5.00 (s, 1H), 4.57-4.52 (m, 1H), 4.49-4.42 (m, 1H), 3.74-3.70 (m, 1H), 3.65-3.61 (m, 1H), 3.19-3.14 (m, 1H), 2.92-2.91 (m, 1H), 2.89 (s, 6H).

HPLC: (Method A) RT. 3.34 min, 96.8% (Max), 93.4% (254 nm).

Compound 21: 8-(2-Fluoro-phenyl)-7-(4-isopropoxy-benzyl)-5,6,7,8-tetrahydro-tetrazolo[1,5-a]pyrazine

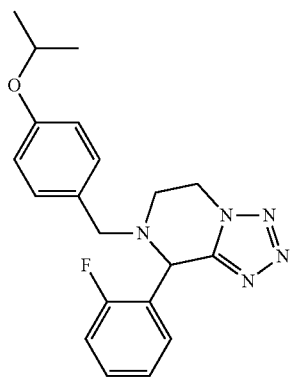 [SMILES: CC(C)Oc1ccc(CN2CCn3nnnc3C2c2ccccc2F)cc1]

It is synthesized using the procedure as described for Compound 1 utilizing 2-fluorobenzaldehyde and 4-isopropoxybenzylamine.

Yield: 187.52 mg, 31.7%.

Color: Yellow gum

LCMS: (Method A) 368.3 (M+1), RT. 5.18 min, 95.1% (Max), 95.3% (220 nm).

¹H NMR (400 MHz, DMSO-d6): δ 7.47-7.41 (m, 2H), 7.30-7.22 (m, 2H), 7.13 (d, J=8.6 Hz, 2H), 6.84 (d, J=8.6 Hz, 2H), 5.29 (s, 1H), 4.58-4.52 (m, 2H), 4.41-4.34 (m, 1H), 3.65-3.62 (m, 1H), 3.40-3.37 (m, 1H), 3.20-3.15 (m, 1H), 2.92-2.85 (m, 1H), 1.22 (d, J=6.0 Hz, 6H).

HPLC: (Method A) RT. 5.66 min, 96.9% (Max), 96.7% (220 nm).

Compound 22: 8-(2-Fluoro-phenyl)-7-(4-methoxy-benzyl)-5,6,7,8-tetrahydro-tetrazolo[1,5-a]pyrazine

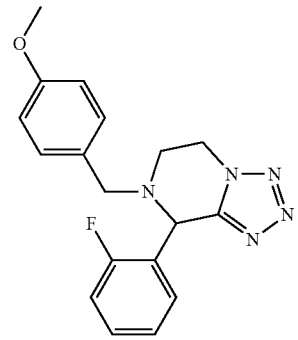 [SMILES: COc1ccc(CN2CCn3nnnc3C2c2ccccc2F)cc1]

It is synthesized using the procedure as described for Compound 1 utilizing 2-fluorobenzaldehyde and 4-methoxybenzylamine Yield: 121.14 mg, 22.2%.

Color: Yellow gum

LCMS: (Method A) 340.3 (M+1), RT. 4.56 min, 95.5% (Max), 95.1% (220 nm).

¹H NMR (400 MHz, DMSO-d6): δ 7.47-7.42 (m, 2H), 7.31-7.22 (m, 2H), 7.16 (d, J=8.5 Hz, 2H), 6.87 (d, J=8.6 Hz, 2H), 5.30 (s, 1H), 4.58-4.54 (m, 1H), 4.41-4.34 (m, 1H), 3.71 (s, 3H), 3.66-3.63 (m, 1H), 3.42-3.38 (m, 1H), 3.18-3.13 (m, 1H), 2.92-2.85 (m, 1H).

HPLC: (Method A) RT 4.78 min, 95.6% (Max), 95.8% (220 nm).

Compound 23: {4-[8-(2-Fluoro-phenyl)-5,6-dihydro-8H-tetrazolo[1,5-a]pyrazin-7-ylmethyl]-phenyl}-dimethyl-amine

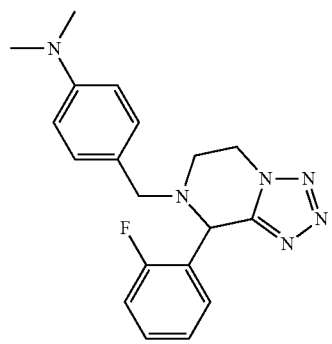 [SMILES: CN(C)c1ccc(CN2CCn3nnnc3C2c2ccccc2F)cc1]

It is synthesized using the procedure as described for Compound 1 utilizing 2-fluorobenzaldehyde and 4-(N,N-dimethylamino)-benzylamine.

Yield: 20.70 mg, 3.6%.

Color: Off white solid

LCMS: (Method B) 353.3 (M+1), RT. 6.23 min, 97.6% (Max), 99.1% (254 nm).

¹H NMR (400 MHz, DMSO-d6): δ 7.47-7.42 (m, 2H), 7.31-7.22 (m, 2H), 7.04 (d, J=8.6 Hz, 2H), 6.66 (d, J=8.7 Hz, 2H), 5.27 (s, 1H), 4.58-4.54 (m, 1H), 4.39-4.32 (m, 1H), 3.63-3.59 (m, 1H), 3.21-3.17 (m, 1H), 2.85-2.82 (m, 7H), 2.41-2.47 (m, 1H).

HPLC: (Method A) RT 6.22 min, 97.2% (Max), 98.9% (254 nm).

Compound 24: 7-(2,5-Difluoro-benzyl)-8-(2-fluoro-phenyl)-5,6,7,8-tetrahydro-tetrazolo[1,5-a]pyrazine

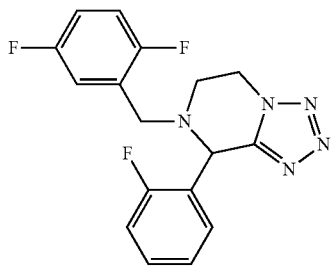 [SMILES: Fc1ccc(F)c(CN2CCn3nnnc3C2c2ccccc2F)c1]

It is synthesized using the procedure as described for Compound 1 utilizing 2-fluorobenzaldehyde and 2,5-difluorobenzylamine.

Yield: 85.35 mg, 15.3%.
Color: White solid
LCMS: (Method A) 346.0 (M+1), RT. 4.72 min, 98.08% (Max), 97.7% (254 nm).
$^1$H NMR (400 MHz, DMSO-d6): δ 7.47-7.39 (m, 2H), 7.27-7.11 (m, 5H), 5.39 (s, 1H), 4.62-4.57 (m, 1H), 4.53-4.46 (m, 1H), 3.71-3.63 (m, 2H), 3.26-3.21 (m, 1H), 3.08-3.01 (m, 1H).
HPLC: (Method A) RT. 4.89 min, 98.8% (Max), 98.4% (254 nm).

Compound 25: 8-(2-Fluoro-phenyl)-7-(3-isopropyl-1-phenyl-1H-pyrazol-4-ylmethyl)-5,6,7,8-tetrahydro-tetrazolo[1,5-a]pyrazine

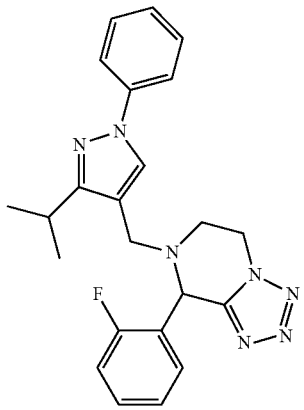 [SMILES: CC(C)c1nn(-c2ccccc2)cc1CN1CCn2nnnc2C1c1ccccc1F]

It is synthesized using the procedure as described for Compound 1 utilizing 2-fluorobenzaldehyde and (3-isopropyl-1-phenyl-1H-pyrazol-4-yl)-methylamine.

Yield: 136.80 mg, 20.3%.
Color: White solid
LCMS: (Method A) 418.2 (M+1), RT. 5.43 min, 99.0% (Max), 98.2% (254 nm).
$^1$H NMR (400 MHz, DMSO-d6): δ 8.36 (s, 1H), 7.77-7.74 (m, 2H), 7.49-7.42 (m, 4H), 7.30-7.21 (m, 3H), 5.29 (s, 1H), 4.61-4.57 (m, 1H), 4.43-4.37 (m, 1H), 3.61-3.58 (m, 1H), 3.42-3.37 (m, 2H), 2.95-2.90 (m, 1H), 2.74-2.71 (m, 1H), 1.13 (d, J=6.8 Hz, 3H), 1.01 (d, J=6.8 Hz, 3H).
HPLC: (Method A) RT. 5.50 min, 99.2% (Max), 98.0% (254 nm).

Compound 26: 7-(2,3-Difluoro-benzyl)-8-(2-fluoro-phenyl)-5,6,7,8-tetrahydro-tetrazolo[1,5-a]pyrazine

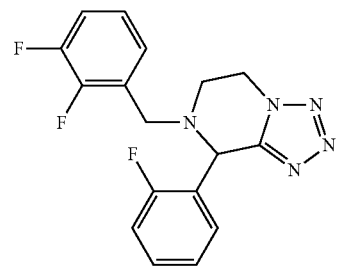 [SMILES: Fc1ccccc1C1c2nnnn2CCN1Cc1cccc(F)c1F]

It is synthesized using the procedure as described for Compound 1 utilizing 2-fluorobenzaldehyde and 2,3-difluorobenzylamine.

Yield: 174.75 mg, 31.4%.
Color: White solid
LCMS: (Method A) 346.2 (M+1), RT. 4.86 min, 92.8% (Max), 91.9% (254 nm).
$^1$H NMR (400 MHz, DMSO-d6): δ 7.46-7.41 (m, 2H), 7.36-7.14 (m, 5H), 5.38 (s, 1H), 4.62-4.57 (m, 1H), 4.47-4.40 (m, 1H), 3.76-3.67 (m, 2H), 3.24-3.19 (m, 1H), 3.06-3.00 (m, 1H).
HPLC: (Method A) RT. 4.93 min, 93.7% (Max), 95.2% (254 nm).

Compound 27: 7-(3-Isopropyl-1-phenyl-1H-pyrazol-4-ylmethyl)-8-m-tolyl-5,6,7,8-tetrahydro-tetrazolo[1,5-a]pyrazine

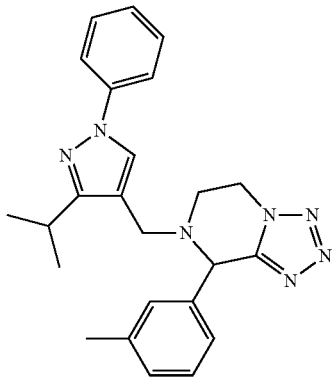 [SMILES: Cc1cccc(C2c3nnnn3CCN2Cc2cn(-c3ccccc3)nc2C(C)C)c1]

It is synthesized using the procedure as described for Compound 1 utilizing 3-methylbenzaldehyde and (3-isopropyl-1-phenyl-1H-pyrazol-4-yl)-methylamine.

Yield: 125.20 mg, 18.2%.
Color: White solid
LCMS: (Method A) 414.2 (M+1), RT. 5.72 min, 99.4% (Max), 99.8% (254 nm).
$^1$H NMR (400 MHz, DMSO-d6): δ 8.37 (s, 1H), 7.78-7.75 (m, 2H), 7.44 (t, J=7.5 Hz, 2H), 7.31-7.28 (m, 1H), 7.25-7.19 (m, 4H), 5.03 (s, 1H), 4.60-4.55 (m, 1H), 4.47-

4.40 (m, 1H), 3.59-3.55 (m, 1H), 3.37-3.34 (m, 1H), 3.23-3.31 (m, 1H), 2.90-2.80 (m, 2H), 2.30 (s, 3H), 1.18 (d, J=6.8 Hz, 3H), 1.07 (d, J=6.8 Hz, 3H).

HPLC: (Method A) RT. 5.76 min, 99.8% (Max), 99.5% (254 nm).

Compound 28: [4-(8-Benzo[1,3]dioxol-5-yl-5,6-dihydro-8H-tetrazolo[1,5-a]pyrazin-7-ylmethyl)-phenyl]-dimethyl-amine

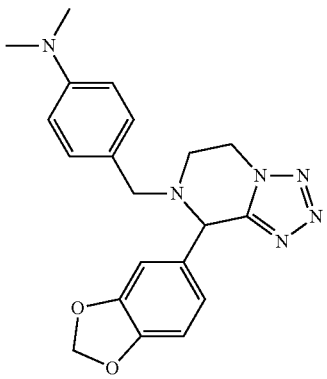 [SMILES: CN(C)c1ccc(CN2CCn3nnnc3C2c2ccc3c(c2)OCO3)cc1]

It is synthesized using the procedure as described for Compound 1 utilizing benzo[1,3]dioxolo-5-carbaldehyde and 4-(N,N-dimethlyamino)-benzylamine.

Yield: 16.63 mg, 3.3%.
Color: Off white solid
LCMS: (Method B) 379.3 (M+1), RT. 6.02 min, 99.1% (Max), 98.3% (254 nm).
$^1$H NMR (400 MHz, DMSO-d6): δ 7.08 (d, J=8.6 Hz, 2H), 6.94-6.90 (m, 3H), 6.68 (d, J=8.6 Hz, 2H), 6.03-6.02 (m, 2H), 4.93 (s, 1H), 4.53-4.48 (m, 1H), 4.41-4.35 (m, 1H), 3.64-3.61 (m, 1H), 3.31-3.28 (m, 1H), 3.09-3.21 (m, 1H), 2.85 (s, 6H), 2.81-2.79 (m, 1H).
HPLC: (Method A) RT. 2.66 min, 99.08% (Max), 99.25% (220 nm).

Compound 29: 8-Benzo[1,3]dioxol-5-yl-7-(3-iso-propyl-1-phenyl-1H-pyrazol-4-ylmethyl)-5,6,7,8-tetrahydro-tetrazolo[1,5-a]pyrazine

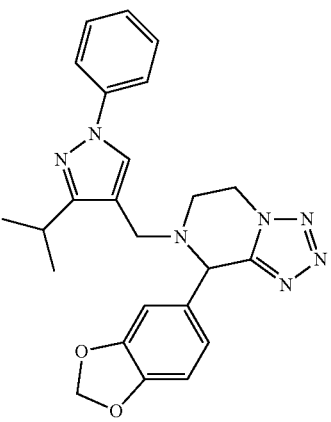 [SMILES: CC(C)c1nn(-c2ccccc2)cc1CN1CCn2nnnc2C1c1ccc2c(c1)OCO2]

It is synthesized using the procedure as described for Compound 1 utilizing benzo[1,3]dioxolo-5-carbaldehyde and (3-isopropyl-1-phenyl-1H-pyrazol-4-yl)-methylamine.

Yield: 181.40 mg, 30.7%.
Color: White solid
LCMS: (Method A) 444.2 (M+1), RT. 5.28 min, 99.3% (Max), 99.1% (254 nm).
$^1$H NMR (400 MHz, DMSO-d6): δ 8.37 (s, 1H), 7.77 (dd, J=1.1, 8.6 Hz, 2H), 7.46-7.42 (m, 2H), 7.23 (t, J=7.4 Hz, 1H), 6.95-6.90 (m, 3H), 6.02 (s, 2H), 5.01 (s, 1H), 4.57-4.53 (m, 1H), 4.46-4.44 (m, 1H), 3.62-3.59 (m, 1H), 3.38-3.34 (m, 1H), 3.29-3.27 (m, 1H), 2.89-2.82 (m, 2H), 1.18 (d, J=6.8 Hz, 3H), 1.10 (d, J=6.8 Hz, 3H).
HPLC: (Method A) RT. 5.27 min, 99.6% (Max), 99.1% (254 nm).

Compound 30: {4-[8-(2,5-Difluoro-phenyl)-5,6-dihydro-8H-tetrazolo[1,5-a]pyrazin-7-ylmethyl]-phenyl}-dimethyl-amine

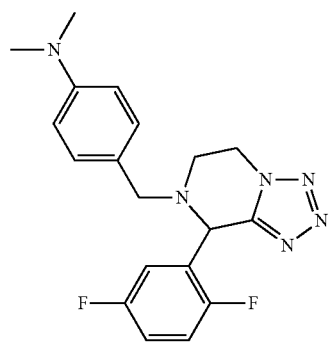 [SMILES: CN(C)c1ccc(CN2CCn3nnnc3C2c2cc(F)ccc2F)cc1]

It is synthesized using the procedure as described for Compound 1 utilizing 2,5-difluorobenzaldehyde and 4-(N,N-dimethylamino)-benzylamine.

Yield: 38.41 mg, 7.4%.
Color: White solid
LCMS: (Method A) 371.2 (M+1), RT. 2.71 min, 99.0% (Max), 99.2% (220 nm).
$^1$H NMR (400 MHz, DMSO-d6): δ 7.38-7.30 (m, 3H), 7.05 (d, J=8.4 Hz, 2H), 6.67 (d, J=8.5 Hz, 2H), 5.28 (s, 1H), 4.56-4.53 (m, 1H), 4.40-4.35 (m, 1H), 3.64-3.61 (m, 1H), 3.39-3.36 (m, 1H), 3.21-3.17 (m, 1H), 2.89-2.85 (m, 7H).
HPLC: (Method A) RT. 2.78 min, 99.8% (Max), 99.7% (220 nm).

Compound 31: 8-(2,5-Difluoro-phenyl)-7-(2-fluoro-benzyl)-5,6,7,8-tetrahydro-tetrazolo[1,5-a]pyrazine

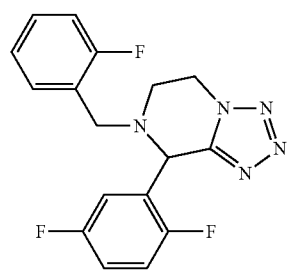 [SMILES: Fc1ccc(F)c(C2c3nnnn3CCN2Cc2ccccc2F)c1]

It is synthesized using the procedure as described for Compound 1 utilizing 2,5-difluorobenzaldehyde and 2-fluorobenzylamine.

Yield: 37.00 mg, 7.6%.
Color: White solid
LCMS: (Method A) 346.0 (M+1), RT. 4.74 min, 95.7% (Max), 95.4% (220 nm).
$^1$H NMR (400 MHz, DMSO-d6): δ 7.42-7.26 (m, 5H), 7.20-7.13 (m, 2H), 5.37 (s, 1H), 4.61-4.57 (m, 1H), 4.47-4.41 (m, 1H), 3.74-3.63 (m, 2H), 3.23-3.20 (m, 1H), 3.05-2.99 (m, 1H).
HPLC: (Method A) RT. 4.79 min, 95.9% (Max), 97.2% (254 nm).

Compound 32: 7-(2,5-Difluoro-benzyl)-8-(2,5-difluoro-phenyl)-5,6,7,8-tetrahydro-tetrazolo[1,5-a]pyrazine

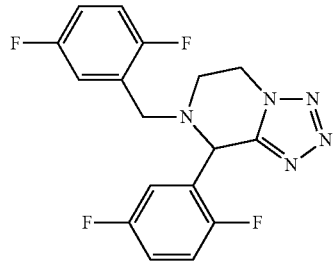 [SMILES: Fc1ccc(F)c(CN2CCn3nnnc3C2c2cc(F)ccc2F)c1]

It is synthesized using the procedure as described for Compound 1 utilizing 2,5-difluorobenzaldehyde and 2,5-difluorobenzylamine.
Yield: 132.85 mg, 26%.
Color: White solid
LCMS: (Method A) 364 (M+1), RT. 4.84 min, 98.6% (Max), 97.7% (254 nm).
$^1$H NMR (400 MHz, DMSO-d6): 400 δ 7.39-7.11 (m, 6H), 5.40 (s, 1H), 4.61-4.56 (m, 1H), 4.54-4.47 (m, 1H), 3.69 (s, 2H), 3.26-3.22 (m, 1H), 3.09-3.02 (m, 1H).
HPLC: (Method A) RT. 4.85 min, 99.3% (Max), 99.2% (254 nm).

Compound 33: 8-(2,5-Difluoro-phenyl)-7-(3-fluoro-benzyl)-5,6,7,8-tetrahydro-tetrazolo[1,5-a]pyrazine

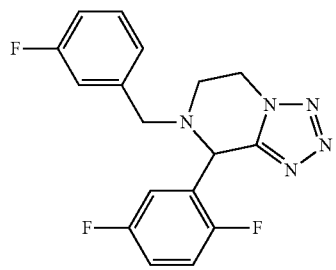 [SMILES: Fc1cccc(CN2CCn3nnnc3C2c2cc(F)ccc2F)c1]

It is synthesized using the procedure as described for Compound 1 utilizing 2,5-difluorobenzaldehyde and 3-fluorobenzylamine.
Yield: 139.63 mg, 28.7%.
Color: White solid
LCMS: (Method A) 346.3 (M+1), RT. 5.47 min, 97.2% (Max), 98.1% (220 nm).
$^1$H NMR (400 MHz, DMSO-d6): δ 7.41-7.25 (m, 4H), 7.13-7.05 (m, 3H), 5.38 (s, 1H), 4.59-4.55 (m, 1H), 4.51-4.44 (m, 1H), 3.75-3.71 (m, 1H), 3.61-3.57 (m, 1H), 3.20-3.15 (m, 1H), 3.02-2.95 (m, 1H).
HPLC: (Method A) RT. 4.85 min, 95.4% (Max), 97.3% (254 nm).

Compound 34: 8-(2,5-Difluoro-phenyl)-7-(3-isopropyl-1-phenyl-1H-pyrazol-4-ylmethyl)-5,6,7,8-tetrahydro-tetrazolo[1,5-a]pyrazine

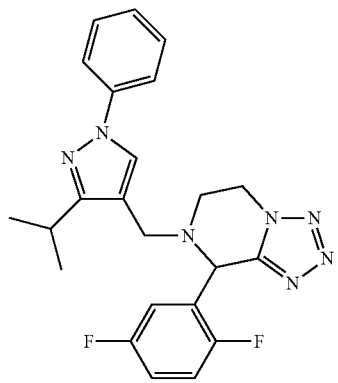 [SMILES: CC(C)c1nn(-c2ccccc2)cc1CN1CCn2nnnc2C1c1cc(F)ccc1F]

It is synthesized using the procedure as described for Compound 1 utilizing 2,5-difluorobenzaldehyde and (3-isopropyl-1-phenyl-1H-pyrazol-4-yl)-methylamine.
Yield: 101.40 mg, 16.6%.
Color: White solid
LCMS: (Method A) 436.2 (M+1), RT. 5.53 min, 99.3% (Max), 99.4% (254 nm).
$^1$H NMR (400 MHz, DMSO-d6): δ 8.38 (s, 1H), 7.76 (d, J=7.8 Hz, 2H), 7.45 (t, J=7.6 Hz, 2H), 7.40-7.28 (m, 3H), 7.23 (t, J=7.3 Hz, 1H), 5.31 (s, 1H), 4.60-4.57 (m, 1H), 4.45-4.38 (m, 1H), 3.62-3.58 (m, 1H), 3.45-3.42 (m, 1H), 3.39-3.32 (m, 1H), 2.97-2.90 (m, 1H), 2.80-2.73 (m, 1H), 1.15 (d, J=6.8 Hz, 3H), 1.04 (d, J=6.8 Hz, 3H).
HPLC: (Method A) RT. 5.57 min, 99.3% (Max), 99.1% (254 nm).

Compound 35: 7-(2,3-Difluoro-benzyl)-8-(2,5-difluoro-phenyl)-5,6,7,8-tetrahydro-tetrazolo[1,5-a]pyrazine

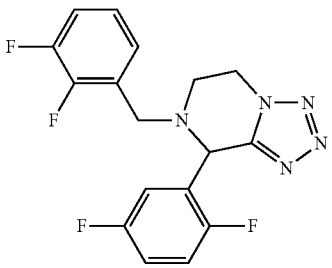 [SMILES: Fc1ccc(F)c(C2c3nnnn3CCN2Cc2cccc(F)c2F)c1]

It is synthesized using the procedure as described for Compound 1 utilizing 2,5-difluorobenzaldehyde and 2,3-difluorobenzylamine.
Yield: 67.74 mg, 13.2%.
Color: White solid
LCMS: (Method A) 364.0 (M+1), RT. 4.85 min, 99.2% (Max), 98.5% (220 nm).

¹H NMR (400 MHz, DMSO-d6): δ 7.36-7.25 (m, 4H), 7.23-7.17 (m, 2H), 5.39 (s, 1H), 4.60-4.57 (m, 1H), 4.48-4.42 (m, 1H), 3.79-3.69 (m, 2H), 3.25-3.21 (m, 1H), 3.08-3.01 (m, 1H).

HPLC: (Method A) RT. 4.85 min, 99.0% (Max), 99.8% (254 nm).

Compound 36: {4-[8-(3-Fluoro-phenyl)-5,6-dihydro-8H-tetrazolo[1,5-a]pyrazin-7-ylmethyl]-phenyl}-dimethyl-amine

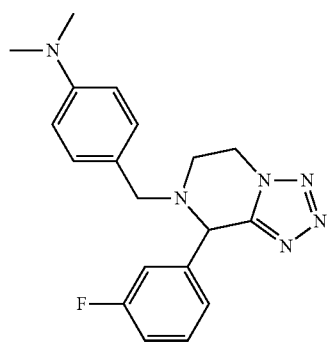 [SMILES: CN(C)c1ccc(CN2CCn3nnnc3C2c2cccc(F)c2)cc1]

It is synthesized using the procedure as described for Compound 1 utilizing 3-fluorbenzaldehyde and 4-(N,N, dimethylamino)-benzylamine.

Yield: 56.25 mg, 7.7%.
Color: White solid
LCMS: (Method A) 353.2 (M+1), RT. 2.80 min, 96.9% (Max), 96.3% (220 nm).
¹H NMR (400 MHz, DMSO-d6): δ 7.47-7.46 (m, 1H), 7.34-7.26 (m, 2H), 7.22-7.20 (m, 1H), 7.10-7.08 (m, 2H), 6.69-6.67 (m, 2H), 5.09 (s, 1H), 4.56-4.53 (m, 1H), 4.47-4.32 (m, 1H), 3.67-3.55 (m, 1H), 3.19-3.16 (m, 2H), 2.93-2.78 (m, 7H).
HPLC: (Method A) RT. 2.81 min, 99.5% (Max), 99.3% (220 nm).

Compound 37: 7-(2,5-Difluoro-benzyl)-8-(3-fluoro-phenyl)-5,6,7,8-tetrahydro-tetrazolo[1,5-a]pyrazine

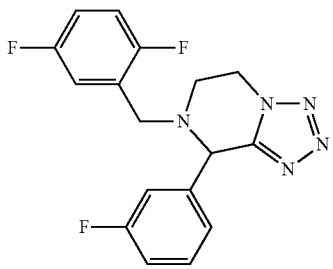 [SMILES: Fc1cccc(C2c3nnnn3CCN2Cc2cc(F)ccc2F)c1]

It is synthesized using the procedure as described for Compound 1 utilizing 3-fluorbenzaldehyde and 2,5-difluorobenzylamine.

Yield: 59.97 mg, 10.8%.
Color: White solid
LCMS: (Method A) 346.3 (M+1), RT. 5.47 min, 95.1% (Max), 97.6% (254 nm).
¹H NMR (400 MHz, DMSO-d6): δ 7.47-7.41 (m, 1H), 7.33-7.29 (m, 3H), 7.24-7.14 (m, 3H), 5.23 (s, 1H), 4.60-4.51 (m, 2H), 3.66 (s, 2H), 3.23-3.18 (m, 1H), 3.02-2.95 (m, 1H).
HPLC: (Method A) RT. 4.85 min, 96.4% (Max), 98.8% (254 nm).

Compound 38: 7-(3-Fluoro-benzyl)-8-(3-fluoro-phenyl)-5,6,7,8-tetrahydro-tetrazolo[1,5-a]pyrazine

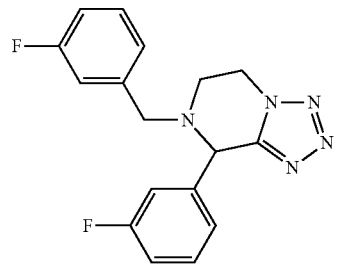 [SMILES: Fc1cccc(CN2CCn3nnnc3C2c2cccc(F)c2)c1]

It is synthesized using the procedure as described for Compound 1 utilizing 3-fluorbenzaldehyde and 3-fluorbenzylamine.

Yield: 130.01 mg, 24.6%.
Color: White solid
LCMS: (Method A) 328.3 (M+1), RT. 4.86 min, 99.3% (Max), 99.3% (220 nm).
¹H NMR (400 MHz, DMSO-d6): δ 7.48-7.43 (m, 1H), 7.40-7.31 (m, 3H), 7.22-7.15 (m, 3H), 7.11-7.06 (m, 1H), 5.20 (s, 1H), 4.58-4.50 (m, 2H), 3.72-3.69 (m, 1H), 3.58-3.55 (m, 1H), 3.18-3.13 (m, 1H), 2.96-2.89 (m, 1H).
HPLC: (Method A) RT. 4.84 min, 99.7% (Max), 99.8% (254 nm).

Compound 39: 7-(4-Chloro-benzyl)-8-(3-fluoro-phenyl)-5,6,7,8-tetrahydro-tetrazolo[1,5-a]pyrazine

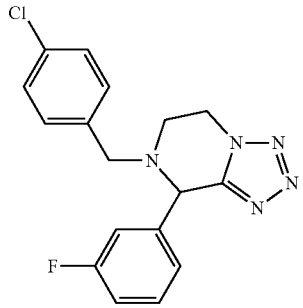 [SMILES: Fc1cccc(C2c3nnnn3CCN2Cc2ccc(Cl)cc2)c1]

It is synthesized using the procedure as described for Compound 1 utilizing 3-fluorbenzaldehyde and 4-chlorobenzylamine.

Yield: 89.53 mg, 16.2%.
Color: Colourless gum
LCMS: (Method A) 344.0 (M+1), RT. 5.13 min, 99.4% (Max), 99.5% (220 nm).
¹H NMR (400 MHz, DMSO-d6): δ 7.48-7.44 (m, 1H), 7.43-7.38 (m, 2H), 7.35-7.30 (m, 4H), 7.23-7.18 (m, 1H), 5.19 (s, 1H), 4.58-4.53 (m, 1H), 4.49-4.42 (m, 1H), 3.70-3.66 (m, 1H), 3.54-3.51 (m, 1H), 3.15-3.10 (m, 1H), 2.94-2.87 (m, 1H).

Compound 40: 8-(3-Fluoro-phenyl)-7-(3-isopropyl-1-phenyl-1H-pyrazol-4-ylmethyl)-5,6,7,8-tetrahydro-tetrazolo[1,5-a]pyrazine

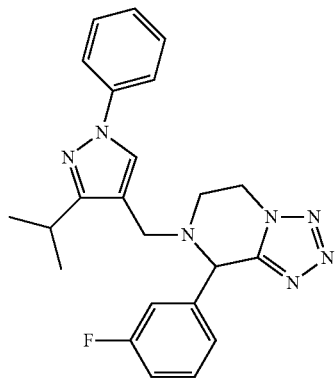

It is synthesized using the procedure as described for Compound 1 utilizing 3-fluorbenzaldehyde and (3-isopropyl-1-phenyl-1H-pyrazol-4-yl)-methylamine.

Yield: 122.60 mg, 18.2%.
Color: Off white solid
LCMS: (Method A) 418.2 (M+1), RT. 5.52 min, 96.8% (Max), 97.7% (254 nm).
$^1$H NMR (400 MHz, DMSO-d6): δ 8.40 (s, 1H), 7.77 (dd, J=1.1, 8.6 Hz, 2H), 7.49-7.43 (m, 3H), 7.31-7.20 (m, 4H), 5.18 (s, 1H), 4.61-4.56 (m, 1H), 4.49-4.43 (m, 1H), 3.60-3.56 (m, 1H), 3.44-3.40 (m, 1H), 3.33-3.27 (m, 1H), 2.94-2.82 (m, 2H), 1.18 (d, J=6.8 Hz, 3H), 1.09 (d, J=6.8 Hz, 3H).
HPLC: (Method A) RT. 5.53 min, 96.9% (Max), 98.1% (254 nm).

Compound 41: 7-(2,3-Difluoro-benzyl)-8-(3-fluoro-phenyl)-5,6,7,8-tetrahydro-tetrazolo[1,5-a]pyrazine

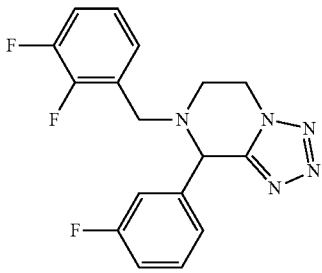 [SMILES: Fc1cccc(C2c3nnnn3CCN2Cc2cccc(F)c2F)c1]

It is synthesized using the procedure as described for Compound 1 utilizing 3-fluorbenzaldehyde and 2,3-difluorobenzaldehyde.

Yield: 106.90 mg, 192%.
Color: Off white solid
LCMS: (Method A) 346.3 (M+1), RT. 4.81 min, 94.7% (Max), 97.0% (254 nm).
$^1$H NMR (400 MHz, DMSO-d6): δ 7.48-7.42 (m, 1H), 7.38-7.24 (m, 4H), 7.22-7.16 (m, 2H), 5.22 (s, 1H), 4.61-4.56 (m, 1H), 4.51-4.45 (m, 1H), 3.75-3.67 (m, 2H), 3.22-3.17 (m, 1H), 3.01-2.94 (m, 1H).

HPLC: (Method A) RT 4.89 min, 96.0% (Max), 96.7% (254 nm).

Compound 42: 8-(4-Chloro-phenyl)-7-(3-fluoro-benzyl)-5,6,7,8-tetrahydro-tetrazolo[1,5-a]pyrazine

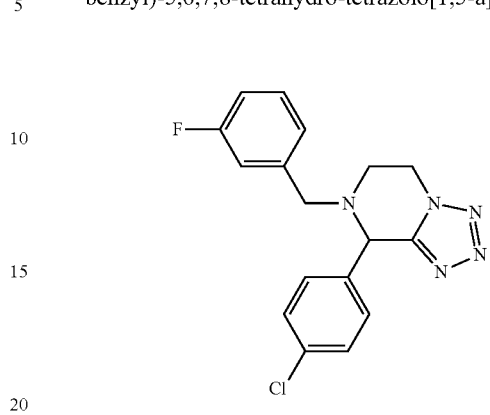

It is synthesized using the procedure as described for Compound 1 utilizing 4-chlorobenzaldehyde and 3-fluorobenzylamine.

Yield: 119.21 mg, 24.4%.
Color: Colourless gum
LCMS: (Method A) 344.2 (M+1), RT. 5.17 min, 97.5% (Max), 97.3% (220 nm).
$^1$H NMR (400 MHz, CDCl3): δ 7.48-7.37 (m, 4H), 7.35-7.30 (m, 1H), 7.08-6.99 (m, 3H), 4.95 (s, 1H), 4.59-4.54 (m, 1H), 4.50-4.43 (m, 1H), 3.91 (d, J=13.6 Hz, 1H), 3.44 (d, J=13.6 Hz, 1H), 3.41-3.35 (m, 1H), 2.95-2.88 (m, 1H).
HPLC: (Method A) RT 5.17 min, 97.0% (Max), 96.7% (220 nm).

Compound 43: 8-(4-Ethoxy-phenyl)-7-(3-isopropyl-1-phenyl-1H-pyrazol-4-ylmethyl)-5,6,7,8-tetrahydro-tetrazolo[1,5-a]pyrazine

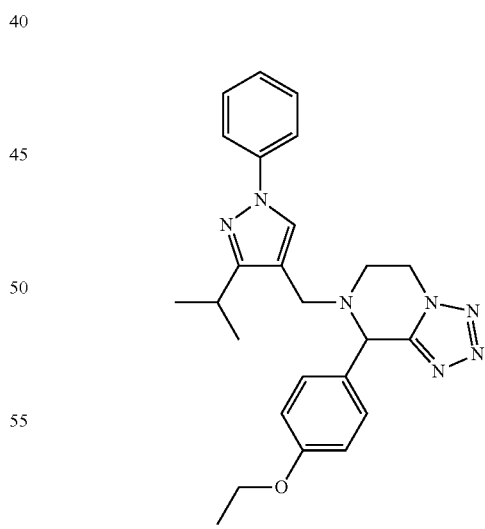

It is synthesized using the procedure as described for Compound 1 utilizing 4-ethoxybenzaldehyde and (3-isopropyl-1-phenyl-1H-pyrazol-4-yl)-methylamine.

Yield: 142.70 mg, 24.2%.
Color: Off white solid
LCMS: (Method A) 444.2 (M+1), RT. 5.63 min, 99.2% (Max), 98.1% (254 nm).

¹H NMR (400 MHz, DMSO-d6): δ 8.35 (s, 1H), 7.76 (dd, J=1.0, 8.6 Hz, 2H), 7.46-7.42 (m, 2H), 7.29-7.21 (m, 3H), 6.94 (d, J=8.8 Hz, 2H), 5.04 (s, 1H), 4.58-4.55 (m, 1H), 4.45-4.43 (m, 1H), 4.05-4.00 (m, 2H), 3.60-3.56 (m, 1H), 3.38-3.34 (m, 1H), 3.31-3.26 (m, 1H), 2.89-2.79 (m, 2H), 1.31 (t, J=6.9 Hz, 3H), 1.17 (d, J=6.8 Hz, 3H), 1.1 (d, J=6.9 Hz, 3H).

HPLC: (Method A) RT. 5.65 min, 98.2% (Max), 97.3% (254 nm).

Compound 44: 7-Cyclohexylmethyl-8-(4-ethoxyphenyl)-5,6,7,8-tetrahydro-tetrazolo[1,5-a]pyrazine

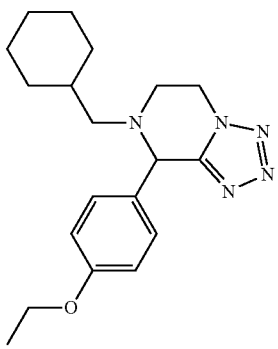 [SMILES: CCOc1ccc(C2c3nnnn3CCN2CC2CCCCC2)cc1]

It is synthesized using the procedure as described for Compound 1 utilizing 4-ethoxybenzaldehyde and cyclohexylmethylamine.

Yield: 37.70 mg, 8.3%.
Color: Yellow solid
LCMS: (Method A) 342.2 (M+1), RT. 5.42 Min, 99.7% (Max), 99.5% (220 nm).
¹H NMR (400 MHz, DMSO-d6): δ 7.18 (d, J=8.6 Hz, 2H), 6.89 (d, J=8.6 Hz, 2H), 4.84 (s, 1H), 4.58-4.54 (m, 1H), 4.49-4.44 (m, 1H), 4.03-3.98 (m, 2H), 3.31-3.27 (m, 1H), 2.84-2.78 (m, 1H), 2.20-2.19 (m, 2H), 1.81-1.78 (m, 1H), 1.57-1.53 (m, 5H), 1.31 (t, J=6.9 Hz, 3H), 1.22-1.01 (m, 3H), 0.72-0.69 (m, 1H), 0.52-0.50 (m, 1H).

HPLC: (Method A) RT. 5.41 min, 99.6% (Max), 99.5% (220 nm).

Compound 45: 7-(2,3-Difluoro-benzyl)-8-(4-ethoxyphenyl)-5,6,7,8-tetrahydro-tetrazolo[1,5-a]pyrazine

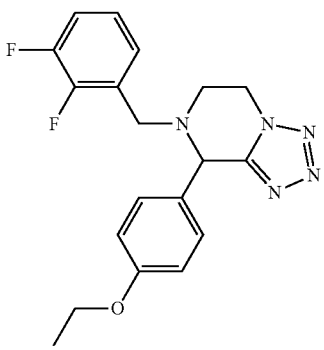 [SMILES: CCOc1ccc(C2c3nnnn3CCN2Cc2cccc(F)c2F)cc1]

It is synthesized using the procedure as described for Compound 1 utilizing 4-ethoxybenzaldehyde and 2,3-difluorobenzylamine.

Yield: 67.89 mg, 13.7%.
Color: Yellow gum
LCMS: (Method A) 372.0 (M+1), RT. 5.0 min, 99.4% (Max), 99.4% (220 nm).
¹H NMR (400 MHz, CDCl₃): δ 7.36-7.34 (m, 2H), 7.14-7.08 (m, 3H), 6.95-6.92 (m, 2H), 4.93 (s, 1H), 4.58-4.54 (m, 1H), 4.51-4.48 (m, 1H), 4.07-4.02 (m, 2H), 3.93-3.89 (m, 1H), 3.68-3.65 (m, 1H), 3.42-3.37 (m, 1H), 2.98-2.91 (m, 1H), 1.42 (t, J=6.9 Hz, 3H).

HPLC: (Method A) RT. 5.07 min, 99.6% (Max), 99.6% (220 nm).

Compound 46: 7-(4-Bromo-benzyl)-8-thiophen-2-yl-5,6,7,8-tetrahydro-tetrazolo[1,5-a]pyrazine

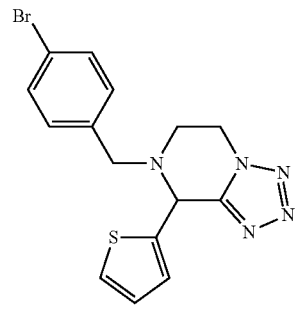 [SMILES: Brc1ccc(CN2CCn3nnnc3C2c2cccs2)cc1]

It is synthesized using the procedure as described for Compound 1 utilizing thiophen-2-carbaldehyde and 4-bromobenzylamine.

Yield: 104.39 mg, 15.6%.
Color: Brown solid
LCMS: (Method A) 376.0 (M+1), RT. 5.04 min, 98.1% (Max), 99.09% (220 nm).
¹H NMR (400 MHz, DMSO-d6): δ 7.57-7.53 (m, 3H), 7.34 (d, J=8.3 Hz, 2H), 7.18-7.17 (m, 1H), 7.05-7.03 (m, 1H), 5.57 (s, 1H), 4.57-4.51 (m, 1H), 4.45-4.39 (m, 1H), 3.79-3.76 (m, 1H), 3.62-3.59 (m, 1H), 3.18-3.13 (m, 1H), 3.00-2.95 (m, 1H).

HPLC: (Method A) RT. 5.07 min, 97.9% (Max), 97.8% (220 nm).

Compound 47: 8-Thiophen-2-yl-7-thiophen-2-ylmethyl-5,6,7,8-tetrahydro-tetrazolo[1,5-a]pyrazine

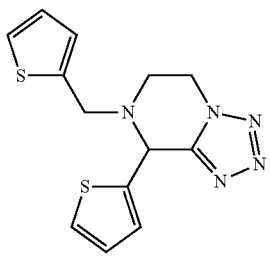 [SMILES: c1csc(CN2CCn3nnnc3C2c2cccs2)c1]

It is synthesized using the procedure as described for Compound 1 utilizing thiophen-2-carbaldehyde and thiophen-2-ylmethylamine.

Yield: 127.09 mg, 23.5%.
Color: Pale yellow solid

LCMS: (Method A) 304.2 (M+1), RT. 4.31 min, 97.8% (Max), 97.1% (220 nm).

¹H NMR (400 MHz, DMSO-d6): δ 7.57 (dd, J=1.1, 5.1 Hz, 1H), 7.48 (dd, J=1.1, 5.1 Hz, 1H), 7.15-7.14 (m, 1H), 7.05-7.03 (m, 2H), 7.00-6.98 (m, 1H), 5.57 (s, 1H), 4.59-4.53 (m, 1H), 4.46-4.40 (m, 1H), 3.99-3.90 (m, 2H), 3.31-3.26 (m, 1H), 3.09-3.03 (m, 1H).

HPLC: (Method A) RT. 4.29 min, 98.7% (Max), 97.4% (254 nm).

Compound 48: 7-(3-Isopropyl-1-phenyl-1H-pyrazol-4-ylmethyl)-8-thiophen-2-yl-5,6,7,8-tetrahydro-tetrazolo[1,5-a]pyrazine

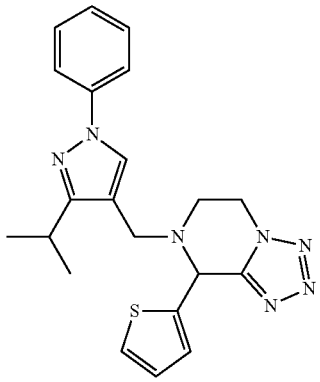 [SMILES: CC(C)c1nn(-c2ccccc2)cc1CN1CCn2nnnc2C1c1cccs1]

It is synthesized using the procedure as described for Compound 1 utilizing thiophen-2-carbaldehyde and (3-isopropyl-1-phenyl-1H-pyrazol-4-yl)-methylamine.

Yield: 27.70 mg, 3.8%.
Color: Brown solid
LCMS: (Method A) 406.2 (M+1), RT. 5.33 min, 97.8% (Max), 99.4% (254 nm).

¹H NMR (400 MHz, DMSO-d6): δ 8.37 (s, 1H), 7.77 (d, J=7.7 Hz, 2H), 7.58-7.57 (m, 1H), 7.47-7.43 (m, 2H), 7.25-7.23 (m, 1H), 7.13-7.12 (m, 1H), 7.05-7.03 (m, 1H), 5.63 (s, 1H), 4.60-4.55 (m, 1H), 4.47-4.43 (m, 1H), 3.73-3.70 (m, 1H), 3.56-3.53 (m, 1H), 3.29-3.24 (m, 1H), 3.08-2.99 (m, 2H), 1.24-1.19 (m, 6H).

HPLC: (Method A) RT. 5.40 min, 99.6% (Max), 99.8% (254 nm).

Compound 49: 7-Cyclohexylmethyl-8-thiophen-2-yl-5,6,7,8-tetrahydro-tetrazolo[1,5-a]pyrazine

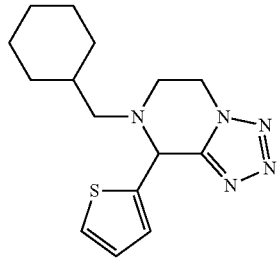 [SMILES: c1csc(C2c3nnnn3CCN2CC2CCCCC2)c1]

It is synthesized using the procedure as described for Compound 1 utilizing thiophen-2-carbaldehyde and cyclohexylmethylamine.

Yield: 70.30 mg, 13.0%.
Color: Yellow gum
LCMS: (Method A) 304.3 (M+1), RT. 5.22 min, 98.9% (Max), 97.5% (254 nm)

¹H NMR (400 MHz, DMSO-d6): δ 7.51 (dd, J=1.3, 5.1 Hz, 1H), 7.04-6.98 (m, 2H), 5.45 (s, 1H), 4.53-4.51 (m, 1H), 4.46-4.44 (m, 1H), 3.31-3.24 (m, 1H), 3.00-2.94 (m, 1H), 2.35-2.31 (m, 2H), 1.81-1.78 (m, 1H), 1.73-1.69 (m, 1H), 1.65-1.59 (m, 4H), 1.22-1.07 (m, 3H), 0.82-0.71 (m, 2H).

HPLC: (Method A) RT. 5.29 min, 99.1% (Max), 97.9% (254 nm).

Compound 50: 7-(2,3-Difluoro-benzyl)-8-thiophen-2-yl-5,6,7,8-tetrahydro-tetrazolo[1,5-a]pyrazine

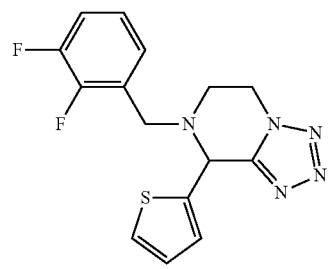 [SMILES: Fc1cccc(CN2CCn3nnnc3C2c2cccs2)c1F]

It is synthesized using the procedure as described for Compound 1 utilizing thiophen-2-carbaldehyde and 2,3-difluorobenzylamine.

Yield: 50.25 mg, 8.5%.
Color: Yellow gum
LCMS: (Method A) 334.0 (M+1), RT. 4.57 min, 98.0% (Max), 97.6% (220 nm).

¹H NMR (400 MHz, CDCl₃): δ 7.37-7.36 (m, 1H), 7.25-7.20 (m, 2H), 7.16-7.11 (m, 2H), 7.05-7.03 (m, 1H), 5.44 (s, 1H), 4.58-4.53 (m, 1H), 4.50-4.43 (m, 1H), 3.99-3.95 (m, 1H), 3.85-3.82 (m, 1H), 3.47-3.41 (m, 1H), 3.05-2.99 (m, 1H).

HPLC: (Method A) RT. 4.65 min, 98.1% (Max), 95.1% (254 nm).

Compound 51: 8-(3-Isopropyl-1-phenyl-1H-pyrazol-4-yl)-7-(4-methoxy-benzyl)-5,6,7,8-tetrahydro-tetrazolo[1,5-a]pyrazine

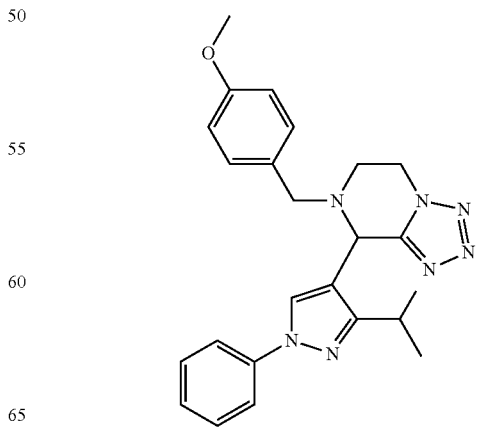

It is synthesized using the procedure as described for Compound 1 utilizing 3-isopropyl-1-phenyl-1H-pyrazole-4-carbaldehyde and 4-methoxybenzylamine.

Yield: 90.58 mg, 22.6%.

Color: Off white solid

LCMS: (Method A) 430.2 (M+1), RT. 5.37 min, 98.2% (Max), 98.7% (254 nm).

$^1$H NMR (400 MHz, DMSO-d6): δ 8.38 (s, 1H), 7.79-7.77 (m, 2H), 7.45 (t, J=7.6 Hz, 2H), 7.27-7.21 (m, 3H), 6.89 (d, J=8.4 Hz, 2H), 5.18 (s, 1H), 4.58-4.53 (m, 1H), 4.39-4.33 (m, 1H), 3.81-3.77 (m, 1H), 3.72 (s, 3H), 3.44-3.41 (m, 1H), 3.23-3.18 (m, 1H), 2.92-2.84 (m, 2H), 1.26 (d, J=6.8 Hz, 3H), 1.07 (d, J=6.8 Hz, 3H).

HPLC: (Method A) RT. 5.45 min, 98.6% (Max), 99.2% (254 nm).

Compound 52: 7-(4-Bromo-benzyl)-8-(3-isopropyl-1-phenyl-1H-pyrazol-4-yl)-5,6,7,8-tetrahydro-tetrazolo[1,5-a]pyrazine

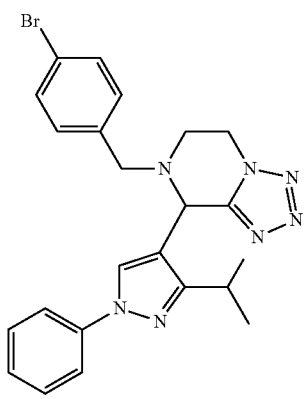 [SMILES: CC(C)c1nn(-c2ccccc2)cc1C1c2nnnn2CCN1Cc1ccc(Br)cc1]

It is synthesized using the procedure as described for Compound 1 utilizing 3-isopropyl-1-phenyl-1H-pyrazole-4-carbaldehyde and 4-bromobenzylamine.

Yield: 56.68 mg, 12.7%.

Color: Yellow solid

LCMS: (Method A) 478.0 (M+1), RT. 6.07 min, 97.3% (Max), 98.5% (254 nm).

$^1$H NMR (400 MHz, DMSO-d6): δ 8.39 (s, 1H), 7.78-7.76 (m, 2H), 7.52 (d, J=8.4 Hz, 2H), 7.45 (t, J=7.5 Hz, 2H), 7.30-7.23 (m, 3H), 5.23 (s, 1H), 4.59-4.53 (m, 1H), 4.43-4.37 (m, 1H), 3.84-3.80 (m, 1H), 3.52-3.49 (m, 1H), 3.22-3.16 (m, 1H), 2.94-2.87 (m, 2H), 1.26-1.22 (m, 3H), 1.07 (d, J=6.8 Hz, 3H).

HPLC: (Method A) RT. 5.98 min, 97.7% (Max), 98.6% (254 nm).

Compound 53: 7-(4-Fluoro-benzyl)-8-(3-isopropyl-1-phenyl-1H-pyrazol-4-yl)-5,6,7,8-tetrahydro-tetrazolo[1,5-a]pyrazine

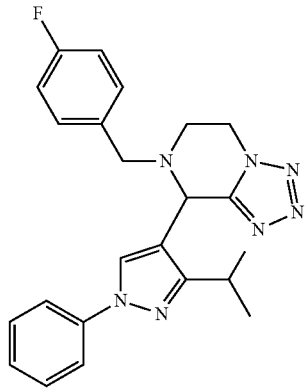 [SMILES: CC(C)c1nn(-c2ccccc2)cc1C1c2nnnn2CCN1Cc1ccc(F)cc1]

It is synthesized using the procedure as described for Compound 1 utilizing 3-isopropyl-1-phenyl-1H-pyrazole-4-carbaldehyde and 4-fluorobenzylamine.

Yield: 120.11 mg, 30.8%.

Color: Pale yellow solid

LCMS: (Method A) 418.2 (M+1), RT. 5.57 min, 99.0% (Max), 99.8% (254 nm).

$^1$H NMR (400 MHz, CDCl$_3$): δ 7.75 (s, 1H), 7.65-7.63 (m, 2H), 7.42 (t, J=7.6 Hz, 2H), 7.32-7.29 (m, 1H), 7.25-7.24 (m, 2H), 7.05 (t, J=8.6 Hz, 2H), 5.07 (s, 1H), 4.56-4.51 (m, 1H), 4.45-4.39 (m, 1H), 4.06-4.03 (m, 1H), 3.42-3.35 (m, 2H), 3.03-2.98 (m, 1H), 2.88-2.81 (m, 1H), 1.41-1.38 (m, 3H), 1.24 (d, J=6.8 Hz, 3H).

HPLC: (Method A) RT. 5.65 min, 99.4% (Max), 99.7% (254 nm).

Compound 54: 7-(2,5-Dimethoxy-benzyl)-8-(3-isopropyl-1-phenyl-1H-pyrazol-4-yl)-5,6,7,8-tetrahydro-tetrazolo[1,5-a]pyrazine

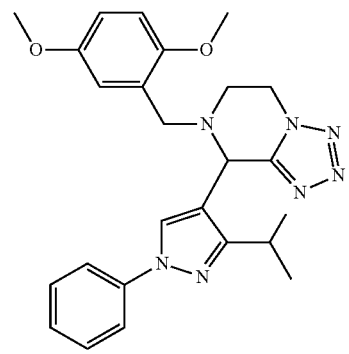 [SMILES: COc1ccc(OC)c(CN2CCn3nnnc3C2c2cn(-c3ccccc3)nc2C(C)C)c1]

It is synthesized using the procedure as described for Compound 1 utilizing 3-isopropyl-1-phenyl-1H-pyrazole-4-carbaldehyde and 2,5-dimethoxy-benzylamine.

Yield: 55.12 mg, 12.9%.

Color: Off white solid

LCMS: (Method A) 460.2 (M+1), RT. 5.15 min, 97.0% (Max), 97.7% (254 nm).

$^1$H NMR (400 MHz, DMSO-d6): δ 8.32 (s, 1H), 7.77-7.75 (m, 2H), 7.44 (t, J=7.7 Hz, 2H), 7.24 (t, J=7.4 Hz, 1H), 7.19 (d, J=8.2 Hz, 1H), 6.53-6.49 (m, 2H), 5.17 (s, 1H), 4.59-4.55 (m, 1H), 4.41-4.37 (m, 1H), 3.73 (s, 3H), 3.69 (s, 3H), 3.67-3.64 (m, 1H), 3.52-3.49 (m, 1H), 3.30-3.21 (m, 1H), 2.93-2.49 (m, 2H), 1.2 (d, J=6.8 Hz, 3H), 1.0 (d, J=6.8 Hz, 3H).

HPLC: (Method A) RT. 5.24 min, 97.0% (Max), 97.5% (254 nm).

Compound 55: {4-[8-(3-Isopropyl-1-phenyl-1H-pyrazol-4-yl)-5,6-dihydro-8H-tetrazolo[1,5-a]pyrazin-7-ylmethyl]-phenyl}-dimethyl-amine

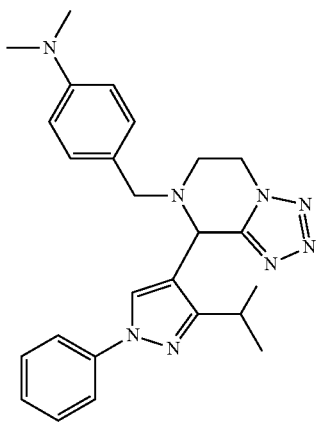 [SMILES: CC(C)c1nn(-c2ccccc2)cc1C1c2nnnn2CCN1Cc1ccc(N(C)C)cc1]

It is synthesized using the procedure as described for Compound 1 utilizing 3-isopropyl-1-phenyl-1H-pyrazole-4-carbaldehyde and 4-(N,N-dimethylamino)-benzylamine.

Yield: 106.35 mg, 25.7%.
Color: Off white solid
LCMS: (Method B) 443.2 (M+1), RT. 7.07 min, 99.0% (Max), 98.1% (254 nm).

$^1$H NMR (400 MHz, DMSO-d6): δ 8.38 (s, 1H), 7.78 (d, J=7.8 Hz, 2H), 7.45 (t, J=7.6 Hz, 2H), 7.25 (t, J=7.4 Hz, 1H), 7.10 (d, J=8.6 Hz, 2H), 6.68 (d, J=8.7 Hz, 2H), 5.15 (s, 1H), 4.57-4.52 (m, 1H), 4.37-4.32 (m, 1H), 3.76-3.73 (m, 1H), 3.37-3.32 (m, 1H), 3.24-3.20 (m, 1H), 2.92-2.84 (m, 8H), 1.26 (d, J=6.8 Hz, 3H), 1.06 (d, J=6.8 Hz, 3H).

HPLC: (Method B) RT. 7.05 min, 98.6% (Max), 98.4% (254 nm).

Compound 56: 7-(2-Fluoro-benzyl)-8-(3-isopropyl-1-phenyl-1H-pyrazol-4-yl)-5,6,7,8-tetrahydro-tetrazolo[1,5-a]pyrazine

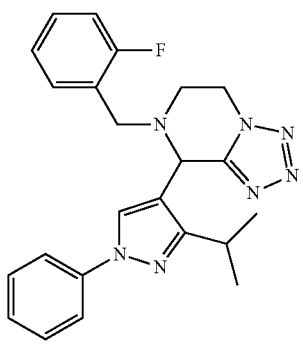 [SMILES: CC(C)c1nn(-c2ccccc2)cc1C1c2nnnn2CCN1Cc1ccccc1F]

It is synthesized using the procedure as described for Compound 1 utilizing 3-isopropyl-1-phenyl-1H-pyrazole-4-carbaldehyde and 2-fluorobenzylamine.

Yield: 108.77 mg, 27.9%.
Color: Pale yellow solid
LCMS: (Method A) 418.2 (M+1), RT. 5.55 min, 95.8% (Max), 98.3% (254 nm).

$^1$H NMR (400 MHz, DMSO-d6): δ 8.37 (s, 1H), 7.76 (d, J=7.7 Hz, 2H), 7.47-7.42 (m, 3H), 7.37-7.34 (m, 1H), 7.32-7.25 (m, 1H), 7.23-7.15 (m, 2H), 5.23 (s, 1H), 4.62-4.57 (m, 1H), 4.45-4.39 (m, 1H), 3.85-3.82 (m, 1H), 3.67-3.62 (m, 1H), 3.28-3.22 (m, 1H), 3.01-2.95 (m, 1H), 2.89-2.82 (m, 1H), 1.22 (d, J=6.8 Hz, 3H), 1.0 (d, J=6.8 Hz, 3H).

HPLC: (Method A) RT. 5.58 min, 96.2% (Max), 98.6% (254 nm).

Compound 57: 8-(3-Isopropyl-1-phenyl-1H-pyrazol-4-yl)-7-(3-methyl-benzyl)-5,6,7,8-tetrahydro-tetrazolo[1,5-a]pyrazine

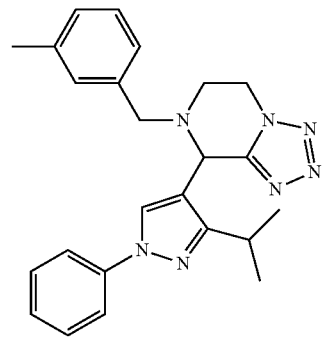 [SMILES: Cc1cccc(CN2CCn3nnnc3C2c2cn(-c3ccccc3)nc2C(C)C)c1]

It is synthesized using the procedure as described for Compound 1 utilizing 3-isopropyl-1-phenyl-1H-pyrazole-4-carbaldehyde and 3-methylbenzylamine.

Yield: 110.19 mg, 28.6%.
Color: Pale yellow solid
LCMS: (Method A) 414.3 (M+1), RT. 5.85 min, 96.8% (Max), 99.5% (254 nm).

$^1$H NMR (400 MHz, DMSO-d6): δ 8.39 (s, 1H), 7.77 (d, J=7.9 Hz, 2H), 7.45 (t, J=7.6 Hz, 2H), 7.27-7.19 (m, 2H), 7.12-7.06 (m, 3H), 5.19 (s, 1H), 4.58-4.55 (m, 1H), 4.40-4.39 (m, 1H), 3.83-3.80 (m, 1H), 3.47-3.44 (m, 1H), 3.24-3.20 (m, 1H), 2.92-2.89 (m, 2H), 2.27 (s, 3H), 1.25 (d, J=6.7 Hz, 3H), 1.05 (d, J=6.7 Hz, 3H).

HPLC: (Method A) RT. 5.87 min, 96.4% (Max), 99.5% (254 nm).

Compound 58: 7-Benzo[1,3]dioxol-5-ylmethyl-8-(3-isopropyl-1-phenyl-1H-pyrazol-4-yl)-5,6,7,8-tetrahydro-tetrazolo[1,5-a]pyrazine

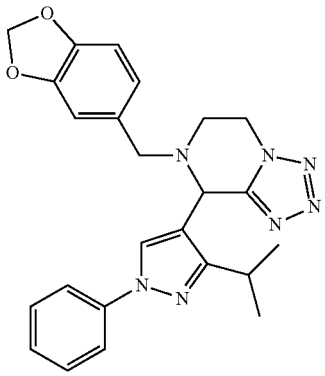 [SMILES: CC(C)c1nn(-c2ccccc2)cc1C1c2nnnn2CCN1Cc1ccc2c(c1)OCO2]

It is synthesized using the procedure as described for Compound 1 utilizing 3-isopropyl-1-phenyl-1H-pyrazole-4-carbaldehyde and benzo[1,3]dioxol-5-ylmethylamine.

Yield: 154.73 mg, 37.4%.
Color: White solid
LCMS: (Method A) 444.3 (M+1), RT. 5.35 min, 95.3% (Max), 98.1% (254 nm).
$^1$H NMR (400 MHz, DMSO-d6): δ 8.39 (s, 1H), 7.77 (d, J=7.6 Hz, 2H), 7.45 (t, J=7.6 Hz, 2H), 7.25 (t, J=7.4 Hz, 1H), 6.88-6.84 (m, 2H), 6.78-6.76 (m, 1H), 5.98-5.96 (m, 2H), 5.19 (s, 1H), 4.57-4.53 (m, 1H), 4.42-4.37 (m, 1H), 3.77-3.74 (m, 1H), 3.43-3.40 (m, 1H), 3.26-3.14 (m, 1H), 2.94-2.86 (m, 2H), 1.27 (d, J=6.84 Hz, 3H), 1.1 (d, J=6.9 Hz, 3H).
HPLC: (Method A) RT. 5.37 min, 97.2% (Max), 98.8% (254 nm).

Compound 59: 7-(2,5-Difluoro-benzyl)-8-(3-isopropyl-1-phenyl-1H-pyrazol-4-yl)-5,6,7,8-tetrahydro-tetrazolo[1,5-a]pyrazine

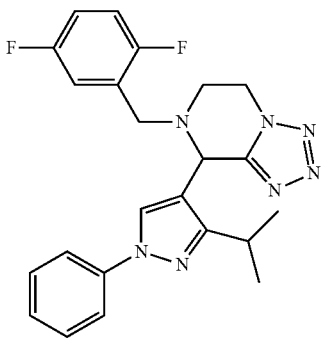 [SMILES: CC(C)c1nn(-c2ccccc2)cc1C1c2nnnn2CCN1Cc1cc(F)ccc1F]

It is synthesized using the procedure as described for Compound 1 utilizing 3-isopropyl-1-phenyl-1H-pyrazole-4-carbaldehyde and 2,5-difluorobenzylamine.

Yield: 110.00 mg, 27.1%.
Color: Pale yellow solid
LCMS: (Method A) 436.3 (M+1), RT. 5.6 min, 96.8% (Max), 97.9% (254 nm).
$^1$H NMR (400 MHz, DMSO-d6): δ 8.39 (s, 1H), 7.75 (d, J=7.8 Hz, 2H), 7.45 (t, J=7.6 Hz, 2H), 7.31-7.14 (m, 4H), 5.26 (s, 1H), 5.26-4.58 (m, 1H), 4.51-4.44 (m, 1H), 3.83-3.80 (m, 1H), 3.69-3.64 (m, 1H), 3.26-3.23 (m, 1H), 3.04-2.98 (m, 1H), 2.92-2.85 (m, 1H), 1.22 (d, J=6.8 Hz, 3H), 1.03 (d, J=6.8 Hz, 3H).
HPLC: (Method A) RT. 5.63 min, 97.1% (Max), 97.7% (254 nm).

Compound 60: 7-(4-Ethoxy-benzyl)-8-(3-isopropyl-1-phenyl-1H-pyrazol-4-yl)-5,6,7,8-tetrahydro-tetrazolo[1,5-a]pyrazine It is synthesized using the procedure as described for Compound 1 utilizing 3-isopropyl-1-phenyl-1H-pyrazole-4-carbaldehyde and 4-ethoxy-benzylamine.

Yield: 89.69 mg, 21.7%.
Color: Pale yellow solid
LCMS: (Method A) 444.2 (M+1), RT. 5.67 min, 98.2% (Max), 99.7% (254 nm).
$^1$H NMR (400 MHz, DMSO-d6): δ 8.38 (s, 1H), 7.77 (d, J=7.8 Hz, 2H), 7.45 (t, J=7.6 Hz, 2H), 7.27-7.20 (m, 3H), 6.87 (d, J=8.6 Hz, 2H), 5.18 (s, 1H), 4.57-4.53 (m, 1H), 4.38-4.34 (m, 1H), 4.01-3.95 (m, 2H), 3.80-3.77 (m, 1H), 3.44-3.40 (m, 1H), 3.23-3.19 (m, 1H), 2.94-2.83 (m, 2H), 1.31-1.25 (m, 6H), 1.07 (d, J=6.8 Hz, 3H).
HPLC: (Method A) RT. 5.74 min, 98.6% (Max), 99.8% (254 nm).

Compound 61: 8-(3-Isopropyl-1-phenyl-1H-pyrazol-4-yl)-7-thiophen-2-ylmethyl-5,6,7,8-tetrahydro-tetrazolo[1,5-a]pyrazine

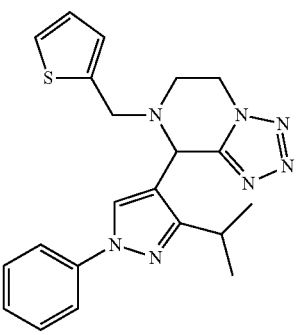 [SMILES: CC(C)c1nn(-c2ccccc2)cc1C1c2nnnn2CCN1Cc1cccs1]

It is synthesized using the procedure as described for Compound 1 utilizing 3-isopropyl-1-phenyl-1H-pyrazole-4-carbaldehyde and thiophen-2-methylamine.

Yield: 137.95 mg, 36.5%.

Color: Pale yellow solid

LCMS: (Method A) 406.2 (M+1), RT. 5.45 min, 99.4% (Max), 99.6% (254 nm).

$^1$H NMR (400 MHz, DMSO-d6): δ 8.40 (s, 1H), 7.79-7.77 (m, 2H), 7.48-7.44 (m, 3H), 7.26 (t, J=7.4 Hz, 1H), 7.04-7.02 (m, 1H), 6.99-6.97 (m, 1H), 5.26 (s, 1H), 4.61-4.57 (m, 1H), 4.42-4.37 (m, 1H), 4.01-3.98 (m, 1H), 3.84-3.80 (m, 1H), 3.25-3.32 (m, 1H), 2.99-2.90 (m, 2H), 1.29 (d, J=6.8 Hz, 3H), 1.04 (d, J=6.8 Hz, 3H)

HPLC: (Method A) RT. 5.47 min, 99.1% (Max), 99.7% (254 nm).

Compound 62: 8-(3-Isopropyl-1-phenyl-1H-pyrazol-4-yl)-7-(3-isopropyl-1-phenyl-1H-pyrazol-4-ylmethyl)-5,6,7,8-tetrahydro-tetrazolo[1,5-a]pyrazine

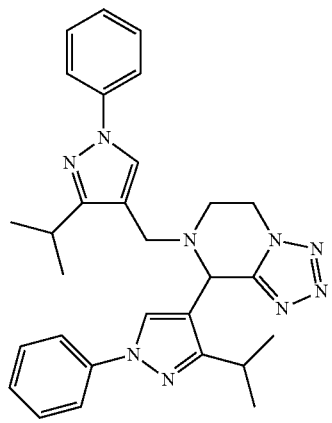 [SMILES: CC(C)c1nn(-c2ccccc2)cc1CN1CCn2nnnc2C1c1cn(-c2ccccc2)nc1C(C)C]

It is synthesized using the procedure as described for Compound 1 utilizing 3-isopropyl-1-phenyl-1H-pyrazole-4-carbaldehyde and (3-isopropyl-1-phenyl-1H-pyrazol-4-yl)-methylamine.

Yield: 27.60 mg, 5.8%.

Color: Off White solid

LCMS: (Method A) 508.2 (M+1), RT. 6.15 min, 99.1% (Max), 97.2% (254 nm).

$^1$H NMR (400 MHz, DMSO-d6): δ 8.36 (d, J=7.7 Hz, 2H), 7.77-7.75 (m, 4H), 7.47-7.43 (m, 4H), 7.24 (q, J=7.3 Hz, 2H), 5.25 (s, 1H), 4.62-4.57 (m, 1H), 4.46-4.40 (m, 1H), 3.74-3.70 (m, 1H), 3.47-3.44 (m, 1H), 3.35-3.39 (m, 1H), 3.01-2.87 (m, 3H), 1.23 (d, J=6.84 Hz, 3H), 1.18 (d, J=6.8 Hz, 3H), 1.09 (d, J=6.8 Hz, 6H).

HPLC: (Method A) RT. 6.21 min, 99.1% (Max), 97.3% (254 nm).

Compound 63: 7-(2,3-Difluoro-benzyl)-8-(3-isopropyl-1-phenyl-1H-pyrazol-4-yl)-5,6,7,8-tetrahydro-tetrazolo[1,5-a]pyrazine

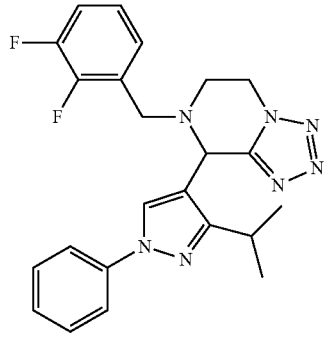 [SMILES: CC(C)c1nn(-c2ccccc2)cc1C1c2nnnn2CCN1Cc1cccc(F)c1F]

It is synthesized using the procedure as described for Compound 1 utilizing 3-isopropyl-1-phenyl-1H-pyrazole-4-carbaldehyde and 2,3-difluorobenzylamine.

Yield: 87.53 mg, 21.6%.

Color: Pale yellow solid

LCMS: (Method A) 436.2 (M+1), RT. 5.62 min, 97.6% (Max), 98.3% (254 nm).

$^1$H NMR (400 MHz, DMSO-d6): δ 8.37 (s, 1H), 7.76 (d, J=7.8 Hz, 2H), 7.45 (t, J=7.6 Hz, 2H), 7.37-7.31 (m, 1H), 7.27-7.24 (m, 2H), 7.21-7.16 (m, 1H), 5.25 (s, 1H), 4.63-4.57 (m, 1H), 4.46-4.40 (m, 1H), 3.90-3.86 (m, 1H), 3.72-3.68 (m, 1H), 3.28-3.23 (m, 1H), 3.04-2.97 (m, 1H), 2.88-2.81 (m, 1H), 1.22 (d, J=6.8 Hz, 3H), 1.0 (d, J=6.8 Hz, 3H).

HPLC: (Method A) RT. 5.64 min, 98.3% (Max), 99.2% (254 nm).

Compound 64: 8-Cyclohexyl-7-(4-isopropoxy-benzyl)-5,6,7,8-tetrahydro-tetrazolo[1,5-a]pyrazine

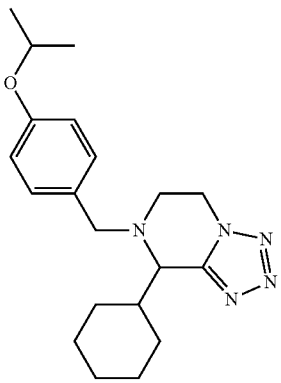 [SMILES: CC(C)Oc1ccc(CN2CCn3nnnc3C2C2CCCCC2)cc1]

It is synthesized using the procedure as described for Compound 1 utilizing cyclohexylcarbaldehyde and 4-isopropoxybenzylamine.

Yield: 84.20 mg, 13.3%.

Color: White solid

LCMS: (Method A) 356.3 (M+1), RT. 5.55 min, 99.8% (Max), 99.8% (220 nm).

$^1$H NMR (400 MHz, DMSO-d6): δ 7.20 (d, J=8.5 Hz, 2H), 6.86 (d, J=8.5 Hz, 2H), 4.61-4.46 (m, 2H), 4.33-4.28 (m, 1H), 3.71-3.69 (m, 1H), 3.63-3.51 (m, 2H), 3.28-3.23

(m, 1H), 2.99-2.96 (m, 1H), 1.97-1.95 (m, 1H), 1.77-1.71 (m, 2H), 1.71-1.61 (m, 2H), 1.60-1.53 (m, 1H), 1.24 (d, J=6.0 Hz, 6H), 1.15-1.09 (m, 4H), 0.98-0.85 (m, 1H).

HPLC: (Method A) RT. 5.54 min, 99.3% (Max), 99.0% (220 nm).

Compound 65: 7-(3-Bromo-benzyl)-8-cyclohexyl-5,6,7,8-tetrahydro-tetrazolo[1,5-a]pyrazine

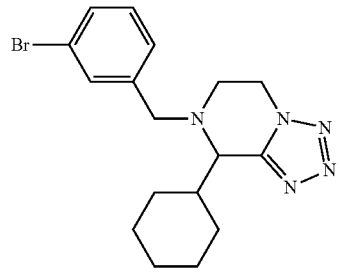 [SMILES: Brc1cccc(CN2CCn3nnnc3C2C2CCCCC2)c1]

It is synthesized using the procedure as described for Compound 1 utilizing cyclohexylcarbaldehyde and 3-bromobenzylamine.

Yield: 220.90 mg, 32.9%.
Color: White solid
LCMS: (Method A) 376.2 (M+1), RT. 5.72 min, 99.3% (Max), 99.3% (220 nm).
$^1$H NMR (400 MHz, DMSO-d6): δ 7.55 (s, 1H), 7.47 (d, J=7.6 Hz, 1H), 7.36-7.29 (m, 2H), 4.54-4.48 (m, 1H), 4.34-4.31 (m, 1H), 3.73-3.70 (m, 2H), 3.66-3.62 (m, 1H), 3.32-3.24 (m, 1H), 3.01-2.97 (m, 1H), 1.99-1.96 (m, 1H), 1.78-1.58 (m, 5H), 1.20-1.04 (m, 4H), 0.96-0.93 (m, 1H).

HPLC: (Method A) RT. 5.71 min, 99.3% (Max), 99.2% (220 nm).

Compound 66: [4-(8-Cyclohexyl-5,6-dihydro-8H-tetrazolo[1,5-a]pyrazin-7-ylmethyl)-phenyl]-dimethyl-amine

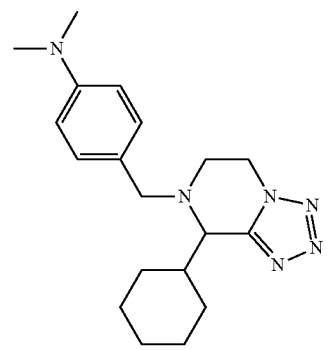 [SMILES: CN(C)c1ccc(CN2CCn3nnnc3C2C2CCCCC2)cc1]

It is synthesized using the procedure as described for Compound 1 utilizing cyclohexylcarbaldehyde and 4-(N,N-dimethylamino)-benzylamine.

Yield: 7.04 mg, 7.1%.
Color: White solid
LCMS: (Method B) 341.3 (M+1), RT. 6.88 min, 93.6% (Max), 95.1% (254 nm).
$^1$H NMR (400 MHz, DMSO-d6): δ 7.10 (d, J=8.6 Hz, 2H), 6.68 (d, J=8.7 Hz, 2H), 4.55-4.46 (m, 1H), 4.32-4.27 (m, 1H), 3.69-3.67 (m, 1H), 3.58-3.55 (m, 1H), 3.49-3.46 (m, 1H), 3.28-3.23 (m, 1H), 3.00-2.96 (m, 1H), 2.86 (s, 6H), 1.98-1.95 (m, 1H), 1.77-1.57 (m, 5H), 1.27-1.02 (m, 4H), 0.95-0.82 (m, 1H).

HPLC: (Method A) RT. 3.19 min, 93.1% (Max), 93.4% (220 nm).

Compound 67: 8-Cyclohexyl-7-(4-ethoxy-benzyl)-5,6,7,8-tetrahydro-tetrazolo[1,5-a]pyrazine

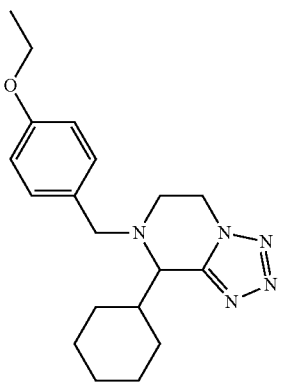 [SMILES: CCOc1ccc(CN2CCn3nnnc3C2C2CCCCC2)cc1]

It is synthesized using the procedure as described for Compound 1 utilizing cyclohexylcarbaldehyde and 4-ethoxy-benzylamine.

Yield: 78.64 mg, 13.1%.
Color: White gum
LCMS: (Method A) 342.3 (M+1), RT. 5.28 min, 99.4% (Max), 99.2% (220 nm).
$^1$H NMR (400 MHz, DMSO-d6): δ 7.21 (d, J=8.6 Hz, 2H), 6.88 (d, J=8.6 Hz, 2H), 4.49-4.46 (m, 1H), 4.32-4.28 (m, 1H), 4.02-3.97 (m, 2H), 3.70-3.68 (m, 1H), 3.64-3.60 (m, 1H), 3.55-3.51 (m, 1H), 3.21-3.31 (m, 1H), 2.99-2.96 (m, 1H), 1.98-1.95 (m, 1H), 1.77-1.57 (m, 5H), 1.32-1.31 (m, 3H), 1.24-1.02 (m, 4H), 0.98-0.82 (m, 1H).

HPLC: (Method A) RT. 5.27 min, 99.3% (Max), 99.2% (220 nm).

Compound 68: 8-Cyclohexyl-7-thiophen-2-ylmethyl-5,6,7,8-tetrahydro-tetrazolo[1,5-a]pyrazine It is synthesized using the procedure as described for Compound 1 utilizing cyclohexylcarbaldehyde and thiophen-2-benzylamine.

Yield: 105.70 mg, 19.6%.
Color: White solid
LCMS: (Method A) 304.3 (M+1), RT. 5.10 min, 99.1% (Max), 99.3% (220 nm).

¹H NMR (400 MHz, DMSO-d6): δ 7.47 (dd, J=1.4, 4.9 Hz, 1H), 6.98-6.94 (m, 2H), 4.58-4.47 (m, 1H), 4.35-4.30 (m, 1H), 3.99-3.95 (m, 1H), 3.85-3.77 (m, 2H), 3.31-3.26 (m, 1H), 3.10-3.06 (m, 1H), 2.04-1.90 (m, 1H), 1.80-1.64 (m, 4H), 1.62-1.56 (m, 1H), 1.28-1.03 (m, 4H), 0.98-0.82 (m, 1H).

HPLC: (Method A) RT. 5.10 min, 99.4% (Max), 99.1% (220 nm).

Compound 69: 8-Cyclohexyl-7-cyclohexylmethyl-5,6,7,8-tetrahydro-tetrazolo[1,5-a]pyrazine

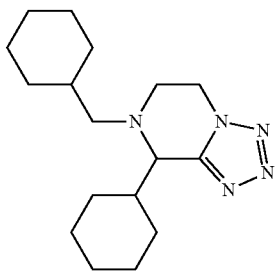 [SMILES: C1CCC(CN2CCn3nnnc3C2C2CCCCC2)CC1]

It is synthesized using the procedure as described for Compound 1 utilizing cyclohexylcarbaldehyde and cyclohexylmethylamine.

Yield: 181.65 mg, 33.6%.
Color: White gum
LCMS: (Method A) 304.3 (M+1), RT. 5.77 min, 99.8% (Max), 99.7% (220 nm).
¹H NMR (400 MHz, DMSO-d6): δ 4.54-4.37 (m, 1H), 4.29-4.25 (m, 1H), 3.63 (d, J=8.4 Hz, 1H), 3.31-3.25 (m, 1H), 2.99-2.96 (m, 1H), 2.34-2.29 (m, 1H), 2.18-2.13 (m, 1H), 2.09-1.89 (m, 1H), 1.87-1.53 (m, 10H), 1.52-1.38 (m, 1H), 1.28-1.03 (m, 7H), 1.00-1.91 (m, 1H), 0.72-0.88 (m, 2H).
HPLC: (Method A) RT. 5.76 min, 99.2% (Max), 99.3% (220 nm).

Compound 70: 7-(3-Bromo-benzyl)-8-(2,3-difluoro-phenyl)-5,6,7,8-tetrahydro-tetrazolo[1,5-a]pyrazine

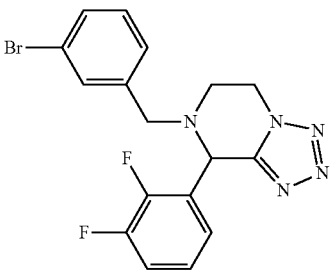 [SMILES: Fc1cccc(C2c3nnnn3CCN2Cc2cccc(Br)c2)c1F]

It is synthesized using the procedure as described for Compound 1 utilizing 2,3-difluorobenzaldehyde and 3-bromo-benzylamine.

Yield: 29.74 mg, 5.2%.
Color: Off white solid
LCMS: (Method A) 406.0 (M+1), RT. 5.19 min, 95.9% (Max), 95.8% (220 nm).
¹H NMR (400 MHz, DMSO-d6): δ 7.50-7.42 (m, 3H), 7.28-7.21 (m, 4H), 5.43 (s, 1H), 4.61-4.56 (m, 1H), 4.49-4.42 (m, 1H), 3.75-3.72 (m, 1H), 3.59-3.56 (m, 1H), 3.21-3.16 (m, 1H), 3.03-2.96 (m, 1H).

HPLC: (Method A) RT. 5.26 min, 96.8% (Max), 97.0% (220 nm).

Compound 71: 8-(2,3-Difluoro-phenyl)-7-(2,5-dimethoxy-benzyl)-5,6,7,8-tetrahydro-tetrazolo[1,5-a]pyrazine

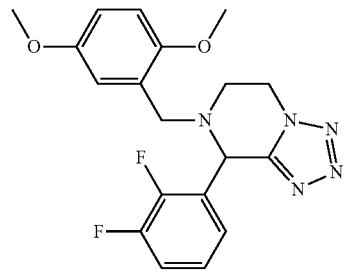 [SMILES: COc1ccc(OC)c(CN2CCn3nnnc3C2c2cccc(F)c2F)c1]

It is synthesized using the procedure as described for Compound 1 utilizing 2,3-difluorobenzaldehyde and 2,5-dimethoxy-benzylamine.

Yield: 219.14 mg, 40.2%.
Color: Pale yellow solid
LCMS: (Method A) 388.3 (M+1), RT. 4.70 min, 91.9% (Max), 91.6% (220 nm).
¹H NMR (400 MHz, DMSO-d6): δ 7.48-7.42 (m, 1H), 7.35-7.31 (m, 1H), 7.26-7.20 (m, 1H), 6.89-6.85 (m, 2H), 6.80-6.77 (m, 1H), 5.39 (s, 1H), 4.60-4.57 (m, 1H), 4.49-4.42 (m, 1H), 3.67 (s, 3H), 3.65-3.53 (m, 5H), 3.28-3.24 (m, 1H), 3.01-2.95 (m, 1H).
HPLC: (Method A) RT. 4.73 min, 91.8% (Max), 92.0% (220 nm).

Compound 72: {4-[8-(2,3-Difluoro-phenyl)-5,6-dihydro-8H-tetrazolo[1,5-a]pyrazin-7-ylmethyl]-phenyl}-dimethyl-amine

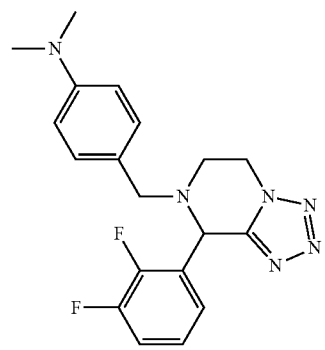 [SMILES: CN(C)c1ccc(CN2CCn3nnnc3C2c2cccc(F)c2F)cc1]

It is synthesized using the procedure as described for Compound 1 utilizing 2,3-difluorobenzaldehyde and 4-(N,N-dimethylamino)-benzylamine.

Yield: 55.70 mg, 10.7%.
Color: White solid
LCMS: (Method B) 371.3 (M+1), RT. 6.29 min, 99.7% (Max), 99.5% (254 nm).
¹H NMR (400 MHz, DMSO-d6): δ 7.51-7.44 (m, 1H), 7.30-7.25 (m, 2H), 7.05 (d, J=8.3 Hz, 2H), 6.67 (d, J=8.4 Hz, 2H), 5.33 (s, 1H), 4.58-4.55 (m, 1H), 4.38-4.34 (m, 1H), 3.65-3.62 (m, 1H), 3.45-3.35 (m, 1H), 3.21-3.18 (m, 1H), 2.90-2.85 (m, 7H).

HPLC: (Method A) RT: 2.81 min, 98.9% (Max), 98.9% (220 nm).

Compound 73: 8-(2,3-Difluoro-phenyl)-7-(2-fluoro-benzyl)-5,6,7,8-tetrahydro-tetrazolo[1,5-a]pyrazine

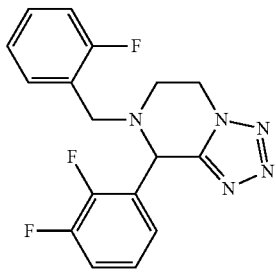 [SMILES: Fc1ccccc1CN1CCn2nnnc2C1c1cccc(F)c1F]

It is synthesized using the procedure as described for Compound 1 utilizing 2,3-difluorobenzaldehyde and 2-fluoro-benzylamine.

Yield: 14.20 mg, 2.9%.
Color: Off white solid
LCMS: (Method A) 346.0 (M+1), RT. 6.17 min, 99.1% (Max), 94.6% (220 nm).
$^1$H NMR (400 MHz, DMSO-d6): δ 7.49-7.37 (m, 2H), 7.35-7.30 (m, 2H), 7.26-7.21 (m, 1H), 7.19-7.12 (m, 2H), 5.42 (s, 1H), 4.62-4.58 (m, 1H), 4.46-4.40 (m, 1H), 3.74-3.64 (m, 2H), 3.24-3.21 (m, 1H), 3.06-2.99 (m, 1H).
HPLC: (Method A) RT. 6.20 min, 97.3% (Max), 97.0% (254 nm).

Compound 74: 7-(2,5-Difluoro-benzyl)-8-(2,3-difluoro-phenyl)-5,6,7,8-tetrahydro-tetrazolo[1,5-a]pyrazine

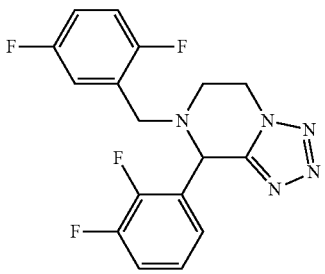 [SMILES: Fc1ccc(F)c(CN2CCn3nnnc3C2c2cccc(F)c2F)c1]

It is synthesized using the procedure as described for Compound 1 utilizing 2,3-difluorobenzaldehyde and 2,5-difluoro-benzylamine.

Yield: 65.25 mg, 12.8%.
Color: White solid
LCMS: (Method A) 364.0 (M+1), RT. 4.83 min, 97.9% (Max), 98.0% (254 nm).
$^1$H NMR (400 MHz, DMSO-d6): δ 7.48-7.41 (m, 1H), 7.32-7.29 (m, 1H), 7.27-7.11 (m, 4H), 5.45 (s, 1H), 4.67-4.59 (m, 1H), 4.51-4.48 (m, 1H), 3.70 (s, 2H), 3.27-3.23 (m, 1H), 3.10-3.03 (m, 1H).
HPLC: (Method A) RT 4.90 min, 97.9% (Max), 96.7% (254 nm).

Compound 75: 8-(2,3-Difluoro-phenyl)-7-(3-fluoro-benzyl)-5,6,7,8-tetrahydro-tetrazolo[1,5-a]pyrazine

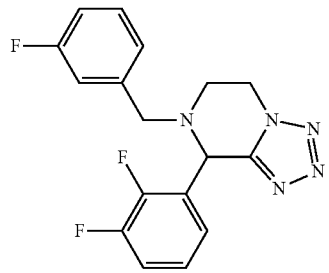 [SMILES: Fc1cccc(CN2CCn3nnnc3C2c2cccc(F)c2F)c1]

It is synthesized using the procedure as described for Compound 1 utilizing 2,3-difluorobenzaldehyde and 3-fluoro-benzylamine.

Yield: 112.77 mg, 23.2%.
Color: White solid
LCMS: (Method A) 346.0 (M+1), RT. 4.82 min, 95.8% (Max), 96.0% (220 nm).
$^1$H NMR (400 MHz, DMSO-d6): δ 7.50-7.43 (m, 1H), 7.38-7.29 (m, 2H), 7.27-7.22 (m, 1H), 7.12-7.05 (m, 3H), 5.44 (s, 1H), 4.61-4.57 (m, 1H), 4.50-4.43 (m, 1H), 3.76-3.72 (m, 1H), 3.60-3.57 (m, 1H), 3.20-3.15 (m, 1H), 3.03-2.96 (m, 1H).
HPLC: (Method A) RT. 4.93 min, 98.1% (Max), 96.4% (254 nm).

Compound 76: 8-(2,3-Difluoro-phenyl)-7-(4-ethoxy-benzyl)-5,6,7,8-tetrahydro-tetrazolo[1,5-a]pyrazine

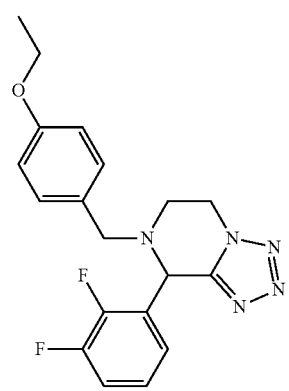 [SMILES: CCOc1ccc(CN2CCn3nnnc3C2c2cccc(F)c2F)cc1]

It is synthesized using the procedure as described for Compound 1 utilizing 2,3-difluorobenzaldehyde and 4-ethoxy-benzylamine.

Yield: 58.22 mg, 11.1%.
Color: Off white solid
LCMS: (Method A) 372.0 (M+1), RT. 5.02 min, 98.4% (Max), 98.0% (220 nm).
$^1$H NMR (400 MHz, DMSO-d6): δ 7.51-7.44 (m, 1H), 7.32-7.24 (m, 2H), 7.15 (d, J=8.6 Hz, 2H), 6.88-6.84 (m, 2H), 5.37 (s, 1H), 4.60-4.55 (m, 1H), 4.41-4.35 (m, 1H), 4.00-3.95 (m, 2H), 3.68-3.65 (m, 1H), 3.44-3.40 (m, 1H), 3.20-3.14 (m, 1H), 2.94-2.88 (m, 1H), 1.29 (t, J=6.9 Hz, 3H).

HPLC: (Method A) RT. 5.11 min, 98.1% (Max), 97.8% (220 nm).

Compound 77: 8-(2,3-Difluoro-phenyl)-7-thiophen-2-ylmethyl-5,6,7,8-tetrahydro-tetrazolo[1,5-a]pyrazine

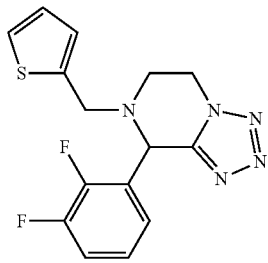 [SMILES: Fc1cccc(C2c3nnnn3CCN2Cc2cccs2)c1F]

It is synthesized using the procedure as described for Compound 1 utilizing 2,3-difluorobenzaldehyde and thiophen-2-carbaldehyde.

Yield: 116.36 mg, 24.8%.
Color: Brown solid
LCMS: (Method A) 334.0 (M+1), RT. 4.61 min, 97.2% (Max), 94.4% (254 nm).
$^1$H NMR (400 MHz, DMSO-d6): δ 7.50-7.45 (m, 2H), 7.32-7.25 (m, 2H), 7.00-6.97 (m, 2H), 5.43 (s, 1H), 4.64-4.59 (m, 1H), 4.46-4.40 (m, 1H), 3.91-3.82 (m, 2H), 3.31-3.29 (m, 1H), 3.07-3.01 (m, 1H).
HPLC: (Method A) RT. 4.66 min, 98.2% (Max), 95.5% (254 nm).

Compound 78: 8-(2,3-Difluoro-phenyl)-7-(3-isopropyl-1-phenyl-1H-pyrazol-4-ylmethyl)-5,6,7,8-tetrahydro-tetrazolo[1,5-a]pyrazine

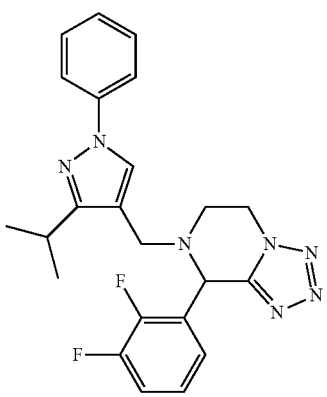 [SMILES: CC(C)c1nn(-c2ccccc2)cc1CN1CCn2nnnc2C1c1cccc(F)c1F]

It is synthesized using the procedure as described for Compound 1 utilizing 2,3-difluorobenzaldehyde and (3-isopropyl-1-phenyl-1H-pyrazol-4-yl)-methylamine.

Yield: 123.60 mg, 20.2%.
Color: White solid
LCMS: (Method A) 436.2 (M+1), RT. 5.62 min, 98.0% (Max), 94.9% (254 nm).
$^1$H NMR (400 MHz, DMSO-d6): δ 8.37 (s, 1H), 7.76 (dd, J=1.1, 8.6 Hz, 2H), 7.51-7.42 (m, 3H), 7.34-7.21 (m, 3H), 5.37 (s, 1H), 4.63-4.59 (m, 1H), 4.44-4.37 (m, 1H), 3.63-3.59 (m, 1H), 3.45-3.42 (m, 1H), 3.40-3.35 (m, 1H), 2.98-2.91 (m, 1H), 2.77-2.70 (m, 1H), 1.13 (d, J=6.8 Hz, 3H), 1.03 (d, J=6.9 Hz, 3H).
HPLC: (Method A) RT. 5.59 min, 97.9% (Max), 95.0% (254 nm).

Compound 79: 7-(2,3-Difluoro-benzyl)-8-(2,3-difluoro-phenyl)-5,6,7,8-tetrahydro-tetrazolo[1,5-a]pyrazine

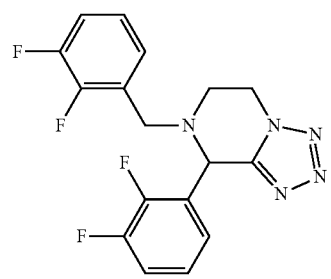 [SMILES: Fc1cccc(CN2CCn3nnnc3C2c2cccc(F)c2F)c1F]

It is synthesized using the procedure as described for Compound 1 utilizing 2,3-difluorobenzaldehyde and 2,3-difluoro-benzylamine.

Yield: 74.71 mg, 14.6%.
Color: White solid
LCMS: (Method A) 364.0 (M+1), RT. 4.84 min, 98.6% (Max), 98.8% (254 nm). $^1$H NMR (400 MHz, DMSO-d6): δ 7.49-7.42 (m, 1H), 7.36-7.28 (m, 2H), 7.25-7.14 (m, 3H), 5.44 (s, 1H), 4.63-4.58 (m, 1H), 4.48-4.41 (m, 1H), 3.80-3.70 (m, 2H), 3.26-3.21 (m, 1H), 3.09-3.02 (m, 1H).
HPLC: (Method A) RT. 4.92 min, 98.5% (Max), 98.2% (220 nm).

Compound 80: 7-(2,4-Dimethoxy-benzyl)-8-(3-fluoro-phenyl)-5,6,7,8-tetrahydro-tetrazolo[1,5-a]pyrazine

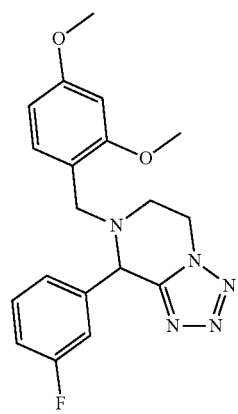 [SMILES: COc1ccc(CN2CCn3nnnc3C2c2cccc(F)c2)c(OC)c1]

It is synthesized using the procedure as described for Compound 1 utilizing 3-fluorobenzaldehyde and 2,4-dimethoxy-benzylamine.

Yield: 28 g, 90%.
Color: Off white solid.
LCMS: (Method A) 370.2 (M+1), RT. 4.6 min, 77.8% (Max).

Compound 81: 8-(3-Fluoro-phenyl)-5,6,7,8-tetrahydro-tetrazolo[1,5-a]pyrazine

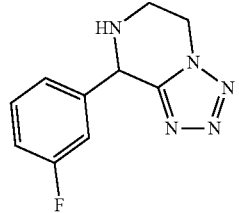 [SMILES: Fc1cccc(C2NCCn3nnnc32)c1]

Procedure: To a solution of 7-(2,4-dimethoxy-benzyl)-8-(3-fluoro-phenyl)-5,6,7,8-tetrahydro-tetrazolo[1,5-a]pyrazine (900 mg, 2.43 mmol) (Compound 80) in dry dichloromethane (10 mL), trifluoroacetic acid (20%, 5 mL) is added at 0° C. and allowed to stir for 4 h at RT. The completion of the reaction is monitored by the TLC, the reaction mixture is quenched with cold water (10 mL), washed with saturated aq. $NaHCO_3$ (2×10 mL), brine (1×10 mL), dried over anhydrous $Na_2SO_4$ and concentrated to get the product.

Yield: 300 mg, 56%.
Color: Off white solid.
LCMS: (Method A) 220.2 (M+1), RT. 0.65 min, 63.7% (Max).

Compound 82: (3-Bromo-phenyl)-[8-(3-fluoro-phenyl)-5,6-dihydro-8H-tetrazolo[1,5-a]pyrazin-7-yl]-methanone

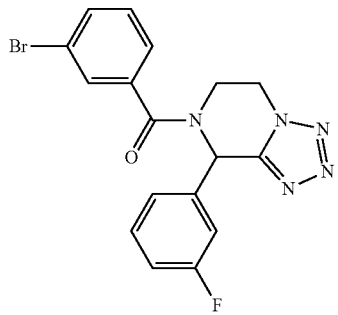 [SMILES: O=C(c1cccc(Br)c1)N1CCn2nnnc2C1c1cccc(F)c1]

Procedure: To a solution of 8-(3-fluoro-phenyl)-5,6,7,8-tetrahydro-tetrazolo[1,5-a]pyrazine (300 mg, 1.36 mmol) (Compound 81) in dry dichloromethane (10 mL), diisopropylethylamine (0.7 mL, 4.1 mmol), 3-bromo-benzoic acid (411 mg, 2.05 mmol) and $T_3P$ (871 mg, 2.73 mmol) are added at 0° C. and allowed to stir for 6 h at RT. The completion of the reaction is monitored by the TLC, the reaction mixture is quenched with cold water (10 mL), washed with brine (1×10 mL), dried over anhydrous Na2SO4 and concentrated. The crude product is purified by the Isolera flash column chromatography to get the product.

Yield: 33.90 mg, 5.2%.
Color: White solid
LCMS: (Method A) 402.0 (M+1), RT. 4.48 min, 99.4% (Max), 99.5% (220 nm).
$^1$H NMR (400 MHz, DMSO-d6, @100° C.): δ 7.71-7.69 (m, 2H), 7.52-7.42 (m, 3H), 7.27-7.19 (m, 3H), 6.94 (s, 1H), 4.67-4.63 (m, 1H), 4.55-4.48 (m, 1H), 4.29-4.24 (m, 1H), 3.74-3.66 (m, 1H).
HPLC: (Method A) RT. 4.52 min, 99.4% (Max), 99.4% (220 nm).

Compound 83: 8-(4-Fluoro-phenyl)-7-pyridin-3-ylmethyl-5,6,7,8-tetrahydro-tetrazolo[1,5-a]pyrazine

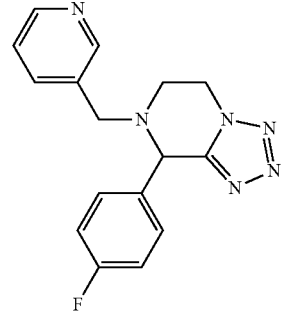 [SMILES: Fc1ccc(C2c3nnnn3CCN2Cc2cccnc2)cc1]

It is synthesized using the procedure as described for Compound 1 utilizing 4-fluorobenzaldehyde and pyrdin-3-ylmethylamine.

Yield: 63.25 mg, 12.6%.
Color: Yellow gum
LCMS: (Method A) 311.2 (M+1), RT. 2.05 min, 96.9% (Max), 95.2% (254 nm).
$^1$H NMR (400 MHz, DMSO-d6): δ 8.49-8.46 (m, 2H), 7.70 (d, J=7.8 Hz, 1H), 7.52-7.48 (m, 2H), 7.36-7.33 (m, 1H), 7.26-7.22 (m, 2H), 5.19 (s, 1H), 4.59-4.54 (m, 1H), 4.49-4.43 (m, 1H), 3.73-3.69 (m, 1H), 3.57-3.53 (m, 1H), 3.17-3.12 (m, 1H), 2.96-2.90 (m, 1H).
HPLC: (Method A) RT. 2.11 min, 97.4% (Max), 96.1% (254 nm).

Compound 84: 8-(4-Fluoro-phenyl)-7-pyridin-4-ylmethyl-5,6,7,8-tetrahydro-tetrazolo[1,5-a]pyrazine

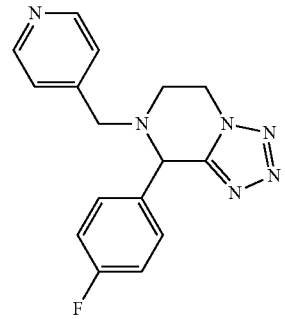 [SMILES: Fc1ccc(C2c3nnnn3CCN2Cc2ccncc2)cc1]

It is synthesized using the procedure as described for Compound 1 utilizing 4-fluorobenzaldehyde and pyrdin-4-ylmethylamine.

Yield: 52.93 mg, 10.6%.
Color: White solid
LCMS: (Method A) 311.2 (M+1), RT. 2.0 min, 91.6% (Max), 92.5% (254 nm).
$^1$H NMR (400 MHz, DMSO-d6): δ 8.50 (d, J=5.9 Hz, 2H), 7.51-7.47 (m, 2H), 7.34 (d, J=5.8 Hz, 2H), 7.22 (t, J=8.8 Hz, 2H), 5.20 (s, 1H), 4.59-4.51 (m, 2H), 3.71-3.67 (m, 1H), 3.59-3.55 (m, 1H), 3.14-3.10 (m, 1H), 2.98-2.93 (m, 1H).

Compound 85: 8-(4-Fluoro-phenyl)-7-(1-methyl-1H-pyrazol-3-ylmethyl)-5,6,7,8-tetrahydro-tetrazolo[1,5-a]pyrazine

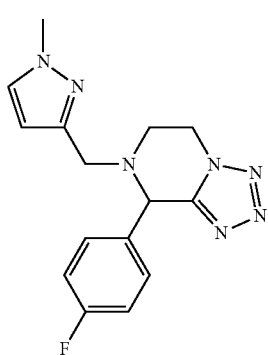 [SMILES: Cn1ccc(CN2CCn3nnnc3C2c2ccc(F)cc2)n1]

It is synthesized using the procedure as described for Compound 1 utilizing 4-fluorobenzaldehyde and (1-methyl-1H-pyrazol-3-yl)-methylamine.

Yield: 54.49 mg, 10.8%.
Color: Yellow gum
LCMS: (Method A) 314.2 (M+1), RT. 3.2 min, 95.8% (Max), 95.8% (220 nm).
$^1$H NMR (400 MHz, DMSO-d6): δ 7.62 (d, J=2.1 Hz, 1H), 7.46-7.42 (m, 2H), 7.26-7.20 (m, 2H), 6.13 (d, J=2.1 Hz, 1H), 5.09 (s, 1H), 4.58-4.54 (m, 1H), 4.46-4.44 (m, 1H), 3.78 (s, 3H), 3.64-3.61 (m, 1H), 3.49-3.45 (m, 1H), 3.31-3.28 (m, 1H), 2.94-2.89 (m, 1H).
HPLC: (Method A) RT. 3.13 min, 95.0% (Max), 95.0% (220 nm).

Compound 86: 7-(3-Methyl-benzyl)-8-pyridin-2-yl-5,6,7,8-tetrahydro-tetrazolo[1,5-a]pyrazine

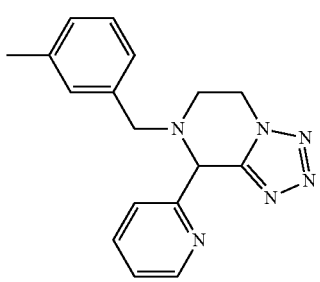 [SMILES: Cc1cccc(CN2CCn3nnnc3C2c2ccccn2)c1]

It is synthesized using the procedure as described for Compound 1 utilizing pyridin-2-carbaldehyde and 3-methyl-benzylamine.

Yield: 55.15 mg, 9.6%.
Color: Brown solid
LCMS: (Method A) 307.3 (M+1), RT. 3.17 min, 98.2% (Max), 98.2% (254 nm).
$^1$H NMR (400 MHz, DMSO-d6): δ 8.53-8.51 (m, 1H), 7.89-7.85 (m, 1H), 7.51 (d, J=7.8 Hz, 1H), 7.40-7.37 (m, 1H), 7.23-7.19 (m, 1H), 7.12-7.06 (m, 3H), 5.36 (s, 1H), 4.55-4.48 (m, 2H), 3.67-3.63 (m, 1H), 3.57-3.53 (m, 1H), 3.31-3.27 (m, 1H), 2.92-2.86 (m, 1H), 2.27 (s, 3H).
HPLC: (Method A) RT. 3.23 min, 98.9% (Max), 98.8% (254 nm).

Compound 87: 7-(3-Methyl-benzyl)-8-pyridin-4-yl-5,6,7,8-tetrahydro-tetrazolo[1,5-a]pyrazine

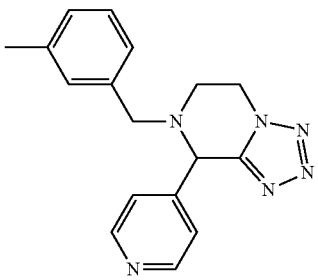 [SMILES: Cc1cccc(CN2CCn3nnnc3C2c2ccncc2)c1]

It is synthesized using the procedure as described for Compound 1 utilizing pyridine-4-carbaldehyde and 3-methyl-benzylamine.

Yield: 17.90 mg, 3.1%.
Color: Brown solid
LCMS: (Method A) 307.3 (M+1), RT. 2.83 min, 99.8% (Max), 99.6% (254 nm).
$^1$H NMR (400 MHz, DMSO-d6): δ 8.62 (dd, J=1.4, 4.6 Hz, 2H), 7.49 (dd, J=1.5, 4.5 Hz, 2H), 7.24-7.20 (m, 1H), 7.13-7.07 (m, 3H), 5.22 (s, 1H), 4.60-4.55 (m, 1H), 4.47-4.41 (m, 1H), 3.68-3.65 (m, 1H), 3.53-3.49 (m, 1H), 3.17-3.12 (m, 1H), 2.97-2.90 (m, 1H), 2.28 (s, 3H).
HPLC: (Method A) RT. 2.88 min, 95.9% (Max), 94.6% (254 nm).

Compound 88: 7-Benzyl-8-(4-isopropoxy-phenyl)-5,6,7,8-tetrahydro-tetrazolo[1,5-a]pyrazine

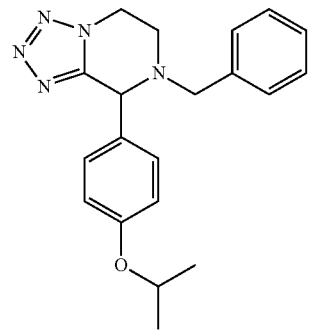 [SMILES: CC(C)Oc1ccc(C2c3nnnn3CCN2Cc2ccccc2)cc1]

It is synthesized using the procedure as described for Compound 1 utilizing 4-isopropoxybenzaldehyde and benzylamine.

Yield: 105.32 mg, 24.8%.
Color: White solid
LCMS: (Method B) 350.3 (M+1), RT. 6.61 min, 99.5% (Max), 98.3% (220 nm).
$^1$H NMR (400 MHz, DMSO-d6): δ 7.35-7.24 (m, 7H), 6.93-6.91 (m, 2H), 5.02 (s, 1H), 4.63-4.52 (m, 2H), 4.46-4.42 (m, 1H), 3.73-3.69 (m, 1H), 3.46-3.43 (m, 1H), 3.16-3.11 (m, 1H), 2.89-2.84 (m, 1H), 1.26-1.24 (m, 6H).
HPLC: (Method A) RT. 5.22 min, 99.5% (Max), 99.5% (220 nm).

Compound 89: 7-Benzyl-8-(3-fluoro-phenyl)-5,6,7,8-tetrahydro-tetrazolo[1,5-a]pyrazine

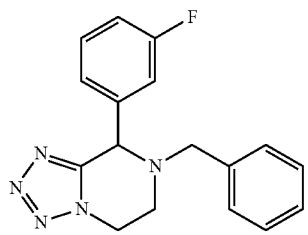 [SMILES: Fc1cccc(C2c3nnnn3CCN2Cc2ccccc2)c1]

It is synthesized using the procedure as described for Compound 1 utilizing 3-fluorobenzaldehyde and benzylamine.

Yield: 183.00 mg, 36.7%.

Color: Pale yellow solid

LCMS: (Method A) 310.3 (M+1), RT. 4.74 min, 98.6% (Max), 99.0% (220 nm).

$^1$H NMR (400 MHz, DMSO-d6): δ 7.49-7.44 (m, 1H), 7.36-7.18 (m, 8H), 5.17 (s, 1H), 4.58-4.53 (m, 1H), 4.49-4.45 (m, 1H), 3.73-3.70 (m, 1H), 3.52-3.49 (m, 1H), 3.17-3.12 (m, 1H), 2.93-2.88 (m, 1H).

HPLC: (Method A) RT. 4.77 min, 98.5% (Max), 96.8% (254 nm).

Compound 90: 7-Benzyl-8-(4-ethyl-phenyl)-5,6,7,8-tetrahydro-tetrazolo[1,5-a]pyrazine

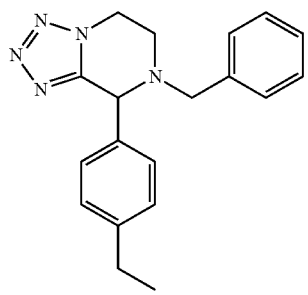 [SMILES: CCc1ccc(C2c3nnnn3CCN2Cc2ccccc2)cc1]

It is synthesized using the procedure as described for Compound 1 utilizing 4-ethylbenzaldehyde and benzylamine.

Yield: 208.44 mg, 43.8%.

Color: White solid

LCMS: (Method A) 320.2 (M+1), RT. 5.28 min, 98.1% (Max), 98.3% (220 nm).

$^1$H NMR (400 MHz, DMSO-d6): δ 7.35-7.31 (m, 6H), 7.29-7.23 (m, 3H), 5.06 (s, 1H), 4.57-4.53 (m, 1H), 4.47-4.44 (m, 1H), 3.72-3.68 (m, 1H), 3.48-3.44 (m, 1H), 3.16-3.13 (m, 1H), 2.90-2.86 (m, 1H), 2.63-2.57 (m, 2H), 1.17 (t, J=7.6 Hz, 3H).

HPLC: (Method A) RT. 5.31 min, 99.5% (Max), 99.5% (220 nm).

Compound 91: 7-(4-Fluoro-benzyl)-8-(3-fluoro-phenyl)-5,6,7,8-tetrahydro-tetrazolo[1,5-a]pyrazine

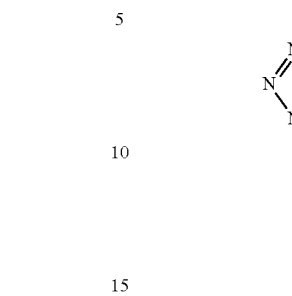

It is synthesized using the procedure as described for Compound 1 utilizing 3-fluorobenzaldehyde and 4-fluorobenzylamine.

Yield: 130.02 mg, 24.7%.

Color: White solid

LCMS: (Method A) 328.3 (M+1), RT. 4.72 min, 98.8% (Max), 98.3% (254 nm).

$^1$H NMR (400 MHz, DMSO-d6): δ 7.48-7.43 (m, 1H), 7.37-7.30 (m, 4H), 7.23-7.13 (m, 3H), 5.18 (s, 1H), 4.59-4.53 (m, 1H), 4.48-4.42 (m, 1H), 3.70-3.66 (m, 1H), 3.53-3.50 (m, 1H), 3.16-3.11 (m, 1H), 2.93-2.86 (m, 1H).

HPLC: (Method A) RT. 4.87 min, 99.5% (Max), 99.0% (254 nm).

Compound 92: 7-(3-Bromo-benzyl)-8-m-tolyl-5,6,7,8-tetrahydro-tetrazolo[1,5-a]pyrazine

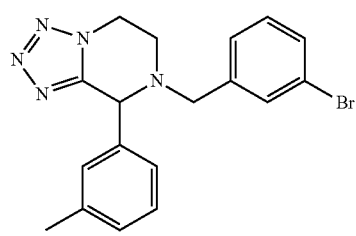 [SMILES: Cc1cccc(C2c3nnnn3CCN2Cc2cccc(Br)c2)c1]

It is synthesized using the procedure as described for Compound 1 utilizing 3-methylbenzaldehyde and 3-bromobenzylamine.

Yield: 292.80 mg, 45.9%.

Color: Off white solid

LCMS: (Method A) 384.2 (M+1), RT. 5.5 min, 98.7% (Max), 98.1% (220 nm).

$^1$H NMR (400 MHz, DMSO-d6): δ 7.48-7.44 (m, 2H), 7.33-7.27 (m, 3H), 7.21-7.16 (m, 3H), 5.06 (s, 1H), 4.57-4.53 (m, 1H), 4.50-4.45 (m, 1H), 3.70-3.66 (m, 1H), 3.52-3.48 (m, 1H), 3.18-3.13 (m, 1H), 2.94-2.88 (m, 1H), 2.30 (s, 3H).

HPLC: (Method A) RT. 5.45 min, 98.7% (Max), 98.3% (220 nm).

Compound 93: 8-(4-Fluoro-phenyl)-7-(3-methyl-benzyl)-5,6,7,8-tetrahydro-tetrazolo[1,5-a]pyrazine

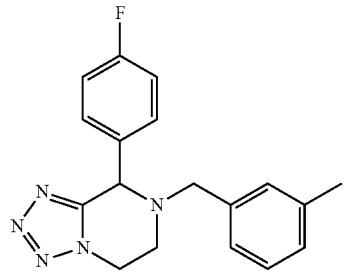

It is synthesized using the procedure as described for Compound 1 utilizing 4-fluorobenzaldehyde and 3-methyl-benzylamine.

Yield: 110.10 mg, 21.1%.

Color: Off white solid

LCMS: (Method A) 324.2 (M+1), RT. 5.05 min, 97.8% (Max), 97.9% (220 nm).

$^1$H NMR (400 MHz, DMSO-d6): δ 7.51-7.46 (m, 2H), 7.27-7.19 (m, 3H), 7.09-7.06 (m, 3H), 5.12 (s, 1H), 4.58-4.53 (m, 1H), 4.46-4.40 (m, 1H), 3.68-3.64 (m, 1H), 3.43-3.40 (m, 1H), 3.18-3.12 (m, 1H), 2.91-2.84 (m, 1H), 2.27 (s, 3H).

HPLC: (Method A) RT. 5.06 min, 97.9% (Max), 97.8% (220 nm).

Compound 94: 7-Benzyl-8-(3-bromo-phenyl)-5,6,7,8-tetrahydro-tetrazolo[1,5-a]pyrazine

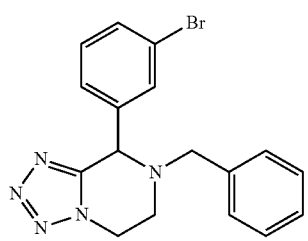 [SMILES: Brc1cccc(C2c3nnnn3CCN2Cc2ccccc2)c1]

It is synthesized using the procedure as described for Compound 1 utilizing 3-bromobenzaldehyde and benzylamine.

Yield: 240.66 mg, 60.3%.

Color: Off white solid

LCMS: (Method A) 370.0 (M+1), RT. 5.11 min, 94.8% (Max), 95.0% (220 nm).

$^1$H NMR (400 MHz, DMSO-d6): δ 7.69-7.68 (m, 1H), 7.58-7.56 (m, 1H), 7.50-7.48 (m, 1H), 7.40-7.38 (m, 1H), 7.36-7.25 (m, 5H), 5.16 (s, 1H), 4.59-4.53 (m, 1H), 4.49-4.43 (m, 1H), 3.73-3.69 (m, 1H), 3.51-3.47 (m, 1H), 3.18-3.12 (m, 1H), 2.93-2.86 (m, 1H).

HPLC: (Method A) RT. 5.14 min, 96.8% (Max), 96.5% (220 nm).

Compound 95: 8-(2,3-Dihydro-benzo[1,4]dioxin-6-yl)-7-(3-methyl-benzyl)-5,6,7,8-tetrahydro-tetrazolo[1,5-a]pyrazine

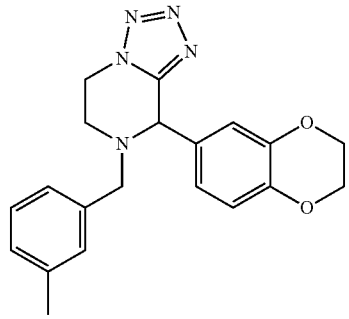 [SMILES: Cc1cccc(CN2CCn3nnnc3C2c2ccc3c(c2)OCCO3)c1]

It is synthesized using the procedure as described for Compound 1 utilizing 2,3-dihydro-benzo[1,4]dioxine-6-carbaldehyde and 3-methyl-benzylamine.

Yield: 225.78 mg, 51%.

Color: Pale yellow solid

LCMS: (Method B) 364.3 (M+1), RT. 3.93 min, 97.5% (Max), 95.7% (220 nm).

$^1$H NMR (400 MHz, DMSO-d6): δ 7.23-7.19 (m, 1H), 7.10-7.06 (m, 3H), 6.90-6.87 (m, 3H), 4.96 (s, 1H), 4.53-4.49 (m, 1H), 4.45-4.42 (m, 1H), 4.29-4.19 (m, 4H), 3.70-3.67 (m, 1H), 3.42-3.39 (m, 1H), 3.18-3.12 (m, 1H), 2.85-2.81 (m, 1H), 2.28 (s, 3H).

HPLC: (Method A) RT. 4.84 min, 98.8% (Max), 98.2% (220 nm).

Compound 96: 7-(3-Bromo-benzyl)-8-(4-fluoro-phenyl)-5,6,7,8-tetrahydro-tetrazolo[1,5-a]pyrazine

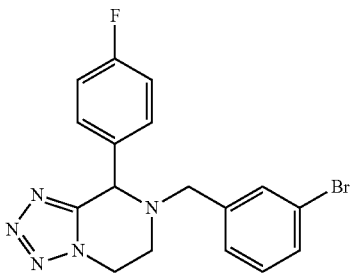 [SMILES: Fc1ccc(C2c3nnnn3CCN2Cc2cccc(Br)c2)cc1]

It is synthesized using the procedure as described for Compound 1 utilizing 4-fluorobenzaldehyde and 3-bromo-benzylamine.

Yield: 268.60 mg, 43.1%.

Color: White solid

LCMS: (Method A) 388.0 (M+1), RT. 5.17 min, 99.2% (Max), 99.4% (220 nm).

$^1$H NMR (400 MHz, DMSO-d6): δ 7.49-7.44 (m, 4H), 7.31-7.21 (m, 4H), 5.16 (s, 1H), 4.59-4.53 (m, 1H), 4.50-4.43 (m, 1H), 3.70-3.66 (m, 1H), 3.53-3.49 (m, 1H), 3.17-3.11 (m, 1H), 2.95-2.88 (m, 1H).

HPLC: (Method A) RT. 5.22 min, 99.6% (Max), 99.3% (220 nm).

Compound 97: 8-(4-Chloro-phenyl)-7-(3-methyl-benzyl)-5,6,7,8-tetrahydro-tetrazolo[1,5-a]pyrazine

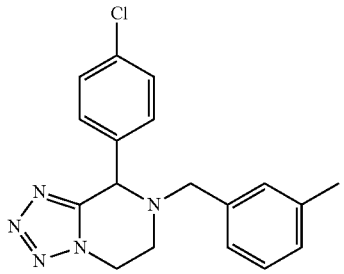 [SMILES: Cc1cccc(CN2CCn3nnnc3C2c2ccc(Cl)cc2)c1]

It is synthesized using the procedure as described for Compound 1 utilizing 4-chlorobenzaldehyde and 3-methyl-benzylamine.

Yield: 207.01 mg, 42.9%.
Color: Pale yellow solid
LCMS: (Method A) 340.3 (M+1), RT. 5.33 min, 97.3% (Max), 97.1% (220 nm).
$^1$H NMR (400 MHz, DMSO-d6): δ 7.52-7.43 (m, 4H), 7.23-7.19 (m, 1H), 7.09-7.06 (m, 3H), 5.13 (s, 1H), 4.58-4.53 (m, 1H), 4.46-4.39 (m, 1H), 3.68-3.64 (m, 1H), 3.44-3.41 (m, 1H), 3.17-3.12 (m, 1H), 2.92-2.85 (m, 1H), 2.27 (s, 3H).
HPLC: (Method A) RT. 5.42 min, 97.5% (Max), 97.4% (220 nm).

Compound 151: 7-(2,3-Difluoro-benzyl)-8-(2,5-dimethoxy-phenyl)-5,6,7,8-tetrahydro-tetrazolo[1,5-a]pyrazine

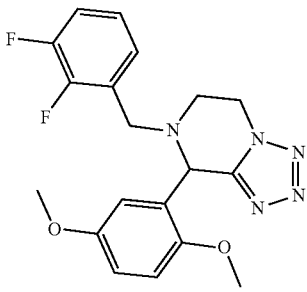 [SMILES: COc1ccc(OC)c(C2c3nnnn3CCN2Cc2cccc(F)c2F)c1]

It is synthesized using the procedure as described for Compound 1 utilizing 2,5-dimethoxybenzaldehyde and 2,3-fluorobenzylamine.

Yield: 178 mg, 38%.
Color: white solid.
LCMS: (Method A) 388.3 (M+1), RT. 4.7 min, 98.4% (Max), 98.0% (220 nm).
$^1$H NMR (400 MHz, DMSO-d6): δ 7.36-7.29 (m, 1H), 7.21-7.14 (m, 2H), 7.02 (d, J=9.0 Hz, 1H), 6.90 (dd, J=3.1, 8.9 Hz, 1H), 6.80 (d, J=3.1 Hz, 1H), 5.36 (s, 1H), 4.57-4.52 (m, 1H), 4.49-4.42 (m, 1H), 3.73-3.70 (m, 4H), 3.66-3.64 (m, 4H), 3.24-3.19 (m, 1H), 3.02-2.95 (m, 1H).
HPLC: (Method A) RT. 4.7 min, 98.9% (Max), 99.1% (254 nm).

The following Compounds according to the present invention are prepared using the procedure as described for Compound 1 utilizing the respective aldehyde and amine and are shown in Table 2:

TABLE 2

| Compound No. | Chemical Name |
|---|---|
| 98 | 7-Benzyl-8-(4-butoxy-phenyl)-5,6,7,8-tetrahydro-tetrazolo[1,5-a]pyrazine |
| 99 | 8-(4-Isopropoxy-phenyl)-7-(3-methyl-benzyl)-5,6,7,8-tetrahydro-tetrazolo[1,5-a]pyrazine |
| 100 | 7-Benzyl-8-m-tolyl-5,6,7,8-tetrahydro-tetrazolo[1,5-a]pyrazine |
| 101 | 7-Benzyl-8-(3,5-difluoro-phenyl)-5,6,7,8-tetrahydro-tetrazolo[1,5-a]pyrazine |
| 102 | 7-Benzyl-8-(4-fluoro-phenyl)-5,6,7,8-tetrahydro-tetrazolo[1,5-a]pyrazine |
| 103 | 8-(4-Butoxy-phenyl)-7-(3-methyl-benzyl)-5,6,7,8-tetrahydro-tetrazolo[1,5-a]pyrazine |
| 104 | 7-(3-Bromo-benzyl)-8-(4-isopropyl-phenyl)-5,6,7,8-tetrahydro-tetrazolo[1,5-a]pyrazine |
| 105 | 7-(3-Methyl-benzyl)-8-phenyl-5,6,7,8-tetrahydro-tetrazolo[1,5-a]pyrazine |
| 106 | 8-(4-Chloro-phenyl)-7-thiophen-2-ylmethyl-5,6,7,8-tetrahydro-tetrazolo[1,5-a]pyrazine |
| 107 | 7-(3-Bromo-benzyl)-8-(3,5-difluoro-phenyl)-5,6,7,8-tetrahydro-tetrazolo[1,5-a]pyrazine |
| 108 | 7-(3-Bromo-benzyl)-8-(2,5-difluoro-phenyl)-5,6,7,8-tetrahydro-tetrazolo[1,5-a]pyrazine |
| 109 | {4-[7-(3-Bromo-benzyl)-5,6,7,8-tetrahydro-tetrazolo[1,5-a]pyrazin-8-yl]-phenyl}-dimethyl-amine |
| 110 | 7-(3-Bromo-benzyl)-8-(4-isopropoxy-phenyl)-5,6,7,8-tetrahydro-tetrazolo[1,5-a]pyrazine |
| 111 | 7-Benzyl-8-(4-chloro-phenyl)-5,6,7,8-tetrahydro-tetrazolo[1,5-a]pyrazine |
| 112 | 7-Benzyl-8-(2,5-difluoro-phenyl)-5,6,7,8-tetrahydro-tetrazolo[1,5-a]pyrazine |
| 113 | 7-Benzyl-8-(2,3-difluoro-phenyl)-5,6,7,8-tetrahydro-tetrazolo[1,5-a]pyrazine |
| 114 | 7-Cyclohexyl-8-(3-isopropyl-1-phenyl-1H-pyrazol-4-yl)-5,6,7,8-tetrahydro-tetrazolo[1,5-a]pyrazine |
| 115 | 7-(3-Bromo-benzyl)-8-(4-ethoxy-phenyl)-5,6,7,8-tetrahydro-tetrazolo[1,5-a]pyrazine |
| 116 | 8-(3-Fluoro-phenyl)-7-(3-methyl-benzyl)-5,6,7,8-tetrahydro-tetrazolo[1,5-a]pyrazine |
| 117 | 8-(3-Fluoro-phenyl)-7-thiophen-2-ylmethyl-5,6,7,8-tetrahydro-tetrazolo[1,5-a]pyrazine |
| 118 | 8-(4-Ethoxy-phenyl)-7-(3-methyl-benzyl)-5,6,7,8-tetrahydro-tetrazolo[1,5-a]pyrazine |
| 119 | 7-(3-Bromo-benzyl)-8-(2-fluoro-phenyl)-5,6,7,8-tetrahydro-tetrazolo[1,5-a]pyrazine |
| 120 | 7-(3-Bromo-benzyl)-8-(4-methoxy-phenyl)-5,6,7,8-tetrahydro-tetrazolo[1,5-a]pyrazine |
| 121 | 8-(4-Isopropoxy-phenyl)-7-thiophen-2-ylmethyl-5,6,7,8-tetrahydro-tetrazolo[1,5-a]pyrazine |
| 122 | 7-Benzyl-8-(4-methoxy-phenyl)-5,6,7,8-tetrahydro-tetrazolo[1,5-a]pyrazine |
| 123 | 7-(3-Bromo-benzyl)-8-phenyl-5,6,7,8-tetrahydro-tetrazolo[1,5-a]pyrazine |
| 124 | 8-(3,5-Difluoro-phenyl)-7-thiophen-2-ylmethyl-5,6,7,8-tetrahydro-tetrazolo[1,5-a]pyrazine |
| 125 | 8-(4-Fluoro-phenyl)-7-thiophen-2-ylmethyl-5,6,7,8-tetrahydro-tetrazolo[1,5-a]pyrazine |
| 126 | {4-[7-(4-Fluoro-benzyl)-5,6,7,8-tetrahydro-tetrazolo[1,5-a]pyrazin-8-yl]-phenyl}-dimethyl-amine |
| 127 | 7-Benzyl-8-phenyl-5,6,7,8-tetrahydro-tetrazolo[1,5-a]pyrazine |
| 128 | 8-(2,5-Dimethoxy-phenyl)-7-(4-fluoro-benzyl)-5,6,7,8-tetrahydro-tetrazolo[1,5-a]pyrazine |
| 129 | Dimethyl-{4-[7-(3-methyl-benzyl)-5,6,7,8-tetrahydro-tetrazolo[1,5-a]pyrazin-8-yl]-phenyl}-amine |
| 130 | 8-(4-Butoxy-phenyl)-7-(2-fluoro-benzyl)-5,6,7,8-tetrahydro-tetrazolo[1,5-a]pyrazine |
| 131 | 7-Benzo[1,3]dioxol-5-ylmethyl-8-(4-isopropoxy-phenyl)-5,6,7,8-tetrahydro-tetrazolo[1,5-a]pyrazine |
| 132 | 7-(4-Fluoro-benzyl)-8-(4-isopropoxy-phenyl)-5,6,7,8-tetrahydro-tetrazolo[1,5-a]pyrazine |
| 133 | 8-(2,3-Dihydro-benzo[1,4]dioxin-6-yl)-7-(4-fluoro-benzyl)-5,6,7,8-tetrahydro-tetrazolo[1,5-a]pyrazine |
| 134 | 8-(4-Ethoxy-phenyl)-7-(4-fluoro-benzyl)-5,6,7,8-tetrahydro-tetrazolo[1,5-a]pyrazine |
| 135 | 7-Benzyl-8-(2,5-dimethoxy-phenyl)-5,6,7,8-tetrahydro-tetrazolo[1,5-a]pyrazine |

TABLE 2-continued

| Compound No. | Chemical Name |
|---|---|
| 136 | 8-(2,4-Difluoro-phenyl)-7-(3-methyl-benzyl)-5,6,7,8-tetrahydro-tetrazolo[1,5-a]pyrazine |
| 137 | 8-(2-Fluoro-phenyl)-7-thiophen-2-ylmethyl-5,6,7,8-tetrahydro-tetrazolo[1,5-a]pyrazine |
| 138 | 8-(4-Chloro-phenyl)-7-(2-fluoro-benzyl)-5,6,7,8-tetrahydro-tetrazolo[1,5-a]pyrazine |
| 139 | 8-Phenyl-7-thiophen-2-ylmethyl-5,6,7,8-tetrahydro-tetrazolo[1,5-a]pyrazine |
| 140 | 8-(2,5-Difluoro-phenyl)-7-thiophen-2-ylmethyl-5,6,7,8-tetrahydro-tetrazolo[1,5-a]pyrazine |
| 141 | 8-(2,5-Dimethoxy-phenyl)-7-(2-fluoro-benzyl)-5,6,7,8-tetrahydro-tetrazolo[1,5-a]pyrazine |
| 142 | 8-(4-Isopropoxy-phenyl)-7-(5-methyl-furan-2-ylmethyl)-5,6,7,8-tetrahydro-tetrazolo[1,5-a]pyrazine |
| 143 | 7-(3-Chloro-benzyl)-8-(3-isopropyl-1-phenyl-1H-pyrazol-4-yl)-5,6,7,8-tetrahydro-tetrazolo[1,5-a]pyrazine |
| 144 | 8-(3-Cyclopropyl-1-ethyl-1H-pyrazol-4-yl)-7-thiophen-2-ylmethyl-5,6,7,8-tetrahydro-tetrazolo[1,5-a]pyrazine |
| 145 | 8-(3-Isopropyl-1-methyl-1H-pyrazol-4-yl)-7-thiophen-2-ylmethyl-5,6,7,8-tetrahydro-tetrazolo[1,5-a]pyrazine |
| 146 | 7-(4-Fluoro-benzyl)-8-(4-methoxy-phenyl)-5,6,7,8-tetrahydro-tetrazolo[1,5-a]pyrazine |
| 147 | 7-(3-Methoxy-benzyl)-8-(4-methoxy-phenyl)-5,6,7,8-tetrahydro-tetrazolo[1,5-a]pyrazine |
| 148 | 7-(4-Chloro-benzyl)-8-(3-isopropyl-1-phenyl-1H-pyrazol-4-yl)-5,6,7,8-tetrahydro-tetrazolo[1,5-a]pyrazine |
| 149 | {4-[7-(4-Isopropoxy-benzyl)-5,6,7,8-tetrahydro-tetrazolo[1,5-a]pyrazin-8-yl]-phenyl}-dimethyl-amine |
| 150 | 7-Benzyl-8-(3-isopropyl-1-phenyl-1H-pyrazol-4-yl)-5,6,7,8-tetrahydro-tetrazolo[1,5-a]pyrazine |
| 152 | 7-Benzyl-8-(4-ethyl-phenyl-1H-pyrazol-4-yl)-5,6,7,8-tetrahydro-tetrazolo[1,5-a]pyrazine |
| 153 | 8-(3-Isopropyl-1-phenyl-1H-pyrazol-4-yl)-7-(2H-pyrazol-3-ylmethyl)-5,6,7,8-tetrahydro-tetrazolo[1,5-a]pyrazine |
| 154 | 8-(3-Isopropyl-1-phenyl-1H-pyrazol-4-yl)-7-pyrazolo[1,5-a]pyridin-3-ylmethyl-5,6,7,8-tetrahydro-tetrazolo[1,5-a]pyrazine |
| 155 | 7-(1-Ethyl-1H-pyrazol-4-ylmethyl)-8-(3-isopropyl-1-phenyl-1H-pyrazol-4-yl)-5,6,7,8-tetrahydro-tetrazolo[1,5-a]pyrazine |
| 156 | 7-(1,5-Dimethyl-1H-pyrazol-4-ylmethyl)-8-(3-isopropyl-1-phenyl-1H-pyrazol-4-yl)-5,6,7,8-tetrahydro-tetrazolo[1,5-a]pyrazine |
| 157 | 8-(3-Isopropyl-1-phenyl-1H-pyrazol-4-yl)-7-(1,3,5-trimethyl-1H-pyrazol-4-ylmethyl)-5,6,7,8-tetrahydro-tetrazolo[1,5-a]pyrazine |
| 158 | 7-(2-Chloro-benzyl)-8-(3-isopropyl-1-phenyl-1H-pyrazol-4-yl)-5,6,7,8-tetrahydro-tetrazolo[1,5-a]pyrazine |
| 159 | 8-(3-Cyclopropyl-1-methyl-1H-pyrazol-4-yl)-7-thiophen-2-ylmethyl-5,6,7,8-tetrahydro-tetrazolo[1,5-a]pyrazine |
| 160 | 8-(1-Benzyl-3-tert-butyl-1H-pyrazol-4-yl)-7-thiophen-2-ylmethyl-5,6,7,8-tetrahydro-tetrazolo[1,5-a]pyrazine |
| 161 | 7-(1-Benzyl-1H-pyrazol-4-ylmethyl)-8-(3-isopropyl-1-phenyl-1H-pyrazol-4-yl)-5,6,7,8-tetrahydro-tetrazolo[1,5-a]pyrazine |
| 162 | 8-(1-Benzyl-3-isopropyl-1H-pyrazol-4-yl)-7-thiophen-2-ylmethyl-5,6,7,8-tetrahydro-tetrazolo[1,5-a]pyrazine |
| 163 | 7-(3-Bromo-benzyl)-8-(3-fluoro-phenyl)-5,6,7,8-tetrahydro-tetrazolo[1,5-a]pyrazine |
| 164 | [4-(7-Benzyl-5,6,7,8-tetrahydro-tetrazolo[1,5-a]pyrazin-8-yl)-phenyl]-dimethyl-amine |

The racemic Compounds according to the present invention and shown in Table 3 are separated into the respective (R)- and (S)-enantiomers using preparative SFC with chiral column material.

Detailed Conditions are:

SFC Berger Minigram System

Column: ChiralPak AS-H, 250×4.6 mm

Eluent: $CO_2$/Methanol 85:15, isocratic flow: 5 mL/min; wavelength: 220 nm

TABLE 3

| Compound No. racemate | Compound Nos. separated enatiomers and retention time | Chemical Name |
|---|---|---|
| 61 | 61-a and 61-b retention a: 3.21 min retention b: 5.63 min | 8-(3-Isopropyl-1-phenyl-1H-pyrazol-4-yl)-7-thiophen-2-ylmethyl-5,6,7,8-tetrahydro-tetrazolo[1,5-a]pyrazine |
| 90 | 90-a and 90-b retention a: 3.83 min retention b: 5.16 min | 7-Benzyl-8-(4-ethyl-phenyl)-5,6,7,8-tetrahydro-tetrazolo[1,5-a]pyrazine |
| 91 | 91-a and 91-b retention a: 3.50 min retention b: 5.46 min | 7-(4-Fluoro-benzyl)-8-(3-fluoro-phenyl)-5,6,7,8-tetrahydro-tetrazolo[1,5-a]pyrazine |
| 92 | 92-a and 92-b retention a: 4.12 min retention b: 5.11 min | 7-(3-Bromo-benzyl)-8-m-tolyl-5,6,7,8-tetrahydro-tetrazolo[1,5-a]pyrazine |
| 93 | 93-a and 93-b retention a: 7.83 min retention b: 8.45 min | 8-(4-Fluoro-phenyl)-7-(3-methyl-benzyl)-5,6,7,8-tetrahydro-tetrazolo[1,5-a]pyrazine |
| 96 | 96-a and 96-b retention a: 4.15 min retention b: 5.53 min | 7-(3-Bromo-benzyl)-8-(4-fluoro-phenyl)-5,6,7,8-tetrahydro-tetrazolo[1,5-a]pyrazine |
| 98 | 98-a and 98-b retention a: 3.48 min retention b: 5.49 min | 7-Benzyl-8-(4-butoxy-phenyl)-5,6,7,8-tetrahydro-tetrazolo[1,5-a]pyrazine |

"a" means - compound eluting from column first
"b" means - compound eluting from column second Biological Activity To assess the inhibitory potential of the compounds according to the present invention on ROR γ, IC50-values are determined, as shown in Table 4 below, by applying a TR-FRET assay and a ROR γ GAl4 Reporter Gene Assay. Both assays are performed in analogy to those described in, inter alia, EP 2511263 A1.

TR-FRET Assay

RORγ is an orphan member of the nuclear receptor (NR) family displaying constitutive activity. The activity of nuclear receptors can be modulated by ligand-induced cofactor protein interactions. For example, agonist binding leads to recruitment of coactivator protein, and antagonist binding either blocks coactivator interaction or facilitates the recruitment of corepressors. A great number of co-activators have been shown to interact with nuclear receptors through a canonical 'LXXLL'-type motif while co-repressors bind via a slightly longer variation of the motif (LXXI/HIXXXI/L). The conformational change induced by ligand binding influences interactions with LXXLL motif peptides.

RORγ (t) is a thymus-specific isoform of RORγ which is widely expressed. It shares the same ligand binding domain (LBD) sequence with RORγ. Thus, a screen using the LBD will yield antagonists targeting both RORγ and RORγt.

In order to identify compounds which block activity of the human nuclear receptor Retinoid-related Orphan Receptor gamma (RORγ) a biochemical cofactor interaction assay based on the TR-FRET principle is performed. In this assay, a GST-tagged human RORγ ligand binding domain (GST-hRORγ-LBD) interacts with a synthetic biotinylated TRAP220 cofactor peptide containing an LXXLL motif (amino acids 631-655 from NP_004765). The ligand-binding domain (LBD) of RORγ is expressed as fusion protein with GST in BL-21 (BL3) cells using the vector pDEST15. Cells are lysed by lysozyme-treatment and sonication, and the fusion proteins purified over glutathione sepharose (Pharmacia) according to the manufacturers instructions. The strong constitutive interaction is disrupted upon binding of functional antagonists. The strength of the interaction is monitored by TR-FRET between streptavidine APC interacting with the biotinylated peptide and Europium-labelled Anti-GST.

6 µl RORγ-LBD-GST solution (final 8.7 nM) in assay buffer (20 mM Tris-HCl, pH 6.8, 5 mM MgCl2, 60 mM KCl, 0.1% delipidated BSA, 1 mM DTT) are dispensed into black 384 well small volume plates (Greiner #784076). 6 µl TRAP220 peptide (final 400 nM), SA-APC (final 1.6 ng/µl), Eu-anti-GST (final 0.125 ng/µl) in assay buffer and 2 µl test compounds (DMSO stocks prediluted in 20 mM Tris-HCl, pH 6.8, 5 mM MgCl2, 60 mM KCl) are added and the mixture incubated 60 min at RT in the dark before measuring FRET (excitation 337 nm, emission at 615 and 665 nm).

As for other TR-FRET assays, the calculation of the fluorescence ratio (665 nm/620 nm) eliminates possible photophysical interferences and allows the assay to be unaffected by e.g. colored compounds.

ROR γ GAl4 Reporter Gene Assay

A Mammalian one-hybrid system is used to perform a cell-based functional transactivation assay for detecting RORγ activity modulators.

The Mammalian-1-Hybrid is derived from the Mammalian-2-Hybrid setup. Whereas in the latter, the binding partners are defined in their role as interaction, transactivation and DNA-binding components, the Mammalian-1-Hybrid makes use of the fact that all mammalian cell types express a set of Nuclear Receptors and their associated cofactors. The M1H construct is a Gal-DNA binding domain (Gal4-DBD; pCMV-BD from Stratagene) fusion construct with the RORγ Ligand binding domain (RORγ-LBD, aa 238-497, NP_001001523). A Gal4 minimal promoter driven luciferase construct (pFR-Luc from Stratagene, containing a synthetic promoter with five tandem repeats of the yeast GAL4 binding sites controlling expression of the Photinus pyralis luciferase gene) is used as reporter. The Gal4-DBD-NR-LBD fusion protein by itself cannot initiate transcription and is dependent on the presence of cofactors present in the cellular system used.

In order to rule out cytotoxic and unspecific transcriptional compound effects a transfection with a firefly luciferase driven by the constitutive CMV promoter is performed in parallel.

For the assay 12,500 293T cells (DSMZ no ACC 635) per 384 well are seeded in 30 µl inMEM Eagle medium, supplemented with 10% FBS, 2 mM Glutamax, 0.1 mM nonessential amino acids, 1 mM Sodium Pyruvate, Penicillin-Streptomycin into white/white bottom 384 well cell culture plates (Greiner #781080) and incubated for 24 h at 37° C., 5% $CO_2$ and 90% rH. The medium is removed, 8 µl/well transfection mix (a OptiMEM-PEI (Sigma-Aldrich #408727)-based transfection-reagent) added and the cells incubated for 4-6 h at 37° C., 5% $CO_2$ and 90% rH after centrifugation for 1 min at 1200 rpm.

After transfection 18 µl complete MEM medium containing 3% charcoal-dextran treated FBS is added as well as 4 µl test compounds (DMSO stocks prediluted in OptiMem (Invitrogen)) followed by incubation for 16-24 h at 37° C., 5% $CO_2$ and 90% rH.

Firefly luciferase activity is measured using the Promega ONE-Glo™ Luciferase Assay System.

Compounds are classified according to their $IC_{50}$ values in the assays described above in three groups:

Group A $IC_{50}$ is in the range of ≥10 nM to ≤990 nM

Group B $IC_{50}$ is in the range of >990 nM to ≤9.9 µM

Group C $IC_{50}$ is in the range of >9.9 µM to ≤40 µM

TABLE 4

| Compound No. | $IC_{50}$ (TR-FRET Assay) | $IC_{50}$ (M1H Assay) |
|---|---|---|
| 1 | C | n.d. |
| 2 | B | B |
| 3 | C | n.d. |
| 4 | C | n.d. |
| 5 | C | n.d. |
| 6 | C | n.d. |
| 7 | B | B |
| 8 | C | n.d. |
| 9 | C | n.d. |
| 10 | C | n.d. |
| 11 | C | n.d. |
| 12 | C | n.d. |
| 13 | C | n.d. |
| 14 | B | A |
| 15 | B | C |
| 16 | C | n.d. |
| 17 | A | B |
| 18 | C | n.d. |
| 19 | C | n.d. |
| 20 | C | n.d. |
| 21 | C | n.d. |
| 22 | C | n.d. |
| 23 | C | n.d. |
| 24 | C | n.d. |
| 25 | B | B |
| 26 | C | n.d. |
| 27 | C | n.d. |
| 28 | C | n.d. |
| 29 | C | n.d. |
| 30 | C | n.d. |
| 31 | C | n.d. |
| 32 | C | n.d. |
| 33 | B | C |
| 34 | A | B |
| 35 | C | n.d. |
| 36 | C | n.d. |
| 37 | C | n.d. |
| 38 | B | B |
| 39 | C | n.d. |
| 40 | C | n.d. |
| 41 | C | n.d. |
| 42 | A | C |
| 43 | C | n.d. |
| 44 | C | n.d. |
| 45 | C | n.d. |
| 46 | C | n.d. |
| 47 | C | n.d. |
| 48 | A | C |
| 49 | C | n.d. |
| 50 | C | n.d. |
| 51 | C | C |
| 52 | A | B |
| 53 | C | n.d. |
| 54 | C | C |
| 55 | B | B |
| 56 | C | n.d. |
| 57 | C | n.d. |
| 58 | C | B |
| 59 | C | n.d. |
| 60 | C | n.d. |
| 61 | A | A |
| 61-a | A | A |
| 61-b | C | B |
| 62 | C | n.d. |
| 63 | C | A |
| 64 | C | n.d. |
| 65 | C | C |
| 66 | C | n.d. |
| 67 | C | n.d. |
| 68 | B | C |
| 69 | C | n.d. |
| 70 | B | B |
| 71 | C | C |
| 72 | C | n.d. |
| 73 | C | n.d. |
| 74 | C | n.d. |
| 75 | B | B |
| 76 | C | n.d. |

TABLE 4-continued

| Compound No. | IC$_{50}$ (TR-FRET Assay) | IC$_{50}$ (M1H Assay) |
|---|---|---|
| 77 | B | B |
| 79 | C | n.d. |
| 80 | B | B |
| 82 | C | n.d. |
| 83 | C | n.d. |
| 84 | B | A |
| 85 | C | n.d. |
| 86 | C | n.d. |
| 87 | C | n.d. |
| 88 | A | B |
| 89 | A | B |
| 90 | A | B |
| 90-a | C | n.d. |
| 90-b | A | B |
| 91 | B | A |
| 91-a | C | n.d. |
| 91-b | B | B |
| 92 | A | B |
| 92-a | C | n.d. |
| 92-b | A | B |
| 93 | A | C |
| 93-a | A | B |
| 93-b | C | n.d. |
| 94 | A | B |
| 95 | A | B |
| 96 | A | B |
| 96-a | A | B |
| 96-b | C | n.d. |
| 97 | A | B |
| 98 | A | B |
| 98-a | A | B |
| 98-b | C | n.d. |
| 99 | A | B |
| 100 | A | C |
| 101 | A | C |
| 102 | A | C |
| 103 | A | B |
| 104 | A | B |
| 105 | A | C |
| 106 | A | C |
| 107 | A | C |
| 108 | A | C |
| 109 | A | C |
| 110 | A | B |
| 111 | B | C |
| 112 | B | C |
| 113 | B | C |
| 114 | B | C |
| 115 | B | B |
| 116 | B | B |
| 117 | B | C |
| 118 | B | C |
| 119 | B | B |
| 120 | B | C |
| 121 | B | B |
| 122 | B | C |
| 123 | B | C |
| 124 | B | C |
| 125 | B | C |
| 126 | B | C |
| 127 | B | C |
| 128 | B | C |
| 129 | B | C |
| 130 | B | B |
| 131 | B | C |
| 132 | B | C |
| 133 | B | C |
| 134 | B | C |
| 135 | B | C |
| 136 | B | C |
| 137 | B | C |
| 138 | B | C |
| 139 | B | C |
| 140 | C | C |
| 141 | C | C |
| 142 | C | C |
| 143 | A | A |
| 144 | B | C |
| 145 | B | C |
| 146 | C | B |
| 147 | C | n.d. |
| 148 | C | B |
| 149 | C | n.d. |
| 150 | C | A |
| 151 | C | n.d. |
| 152 | C | n.d. |
| 153 | C | n.d. |
| 154 | C | B |
| 155 | C | n.d. |
| 156 | C | C |
| 157 | C | n.d. |
| 158 | C | n.d. |
| 159 | C | n.d. |
| 160 | C | B |
| 161 | B | B |
| 162 | A | B |
| 163 | A | C |
| 164 | A | C |

The invention claimed is:
1. A compound of formula (I):

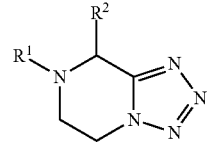

or a physiologically acceptable salt, tautomer or stereoisomer thereof,
wherein:
R$^1$ denotes R$^3$, —CH$_2$—R$^3$ or —(C═O)—R$^3$;
R$^2$ denotes Ar$^2$, Hetar$^2$ or C$_{3-7}$-cycloalkyl;
R$^3$ denotes Ar$^3$, Hetar$^3$ or C$_{3-7}$-cycloalkyl;
Ar$^2$ and Ar$^3$ denote independently a monocyclic or bicyclic aromatic hydrocarbon system having 6 to 10 carbon atoms which system is unsubstituted or substituted with one or more identical or different substituents selected from the group consisting of C$_{1-6}$-alkyl, C$_{1-6}$-alkoxy, C$_{3-7}$-cycloalkyl, —NH$_2$, N—(C$_{1-6}$-alkyl)amino, N,N-(di-C$_{1-6}$-alkyl)amino, halogen, and —O—C$_{1-3}$-alkylene-O—;
Hetar$^2$ denotes an aromatic monocyclic or bicyclic 4- to 10-membered heterocycle having 1, 2 or 3 heteroatoms selected from the group consisting of nitrogen, oxygen and sulfur, which heterocycle is unsubstituted or substituted with one or more identical or different substituents selected from the group consisting of C$_{1-6}$-alkyl, C$_{3-7}$-cycloalkyl, and (C$_{1-6}$-alkyl)$_m$-aryl wherein m is 0 or 1 and aryl is a monocyclic or bicyclic aromatic hydrocarbon system having 6 to 10 carbon atoms which aromatic hydrocarbon system is unsubstituted or substituted with one or more identical or different substituents selected from the group consisting of C$_{1-6}$-alkyl, C$_{1-6}$-alkoxy, C$_{3-7}$-cycloalkyl, —NH$_2$, N—(C$_{1-6}$-alkyl)amino, N,N-(di-C$_{1-6}$-alkyl)amino, and halogen;
Hetar$^3$ denotes an aromatic monocyclic or bicyclic 4- to 10-membered heterocycle having 1, 2 or 3 heteroatoms selected from the group consisting of nitrogen, oxygen and sulfur, which heterocycle is unsubstituted or substituted with one or more identical or different substituents selected from the group consisting of C$_{1-6}$-alkyl, $C_{3-7}$-cycloalkyl, and $(C_{1-6}$-alkyl$)_n$-aryl wherein n is 0 or 1 and aryl is a monocyclic or bicyclic aromatic hydrocarbon system having 6 to 10 carbon atoms which aromatic hydrocarbon system is unsubstituted or substituted with one or more identical or different substituents selected from the group consisting of $C_{1-6}$-alkyl, $C_{1-6}$-alkoxy, $C_{3-7}$-cycloalkyl, —NH$_2$, N—($C_{1-6}$-alkyl)amino, N,N-(di-$C_{1-6}$-alkyl)amino, and halogen;

with the proviso that the following compound of formula (I) is excluded:

7-benzyl-8-(4-methoxyphenyl)-5,6,7,8-tetrahydro-tetrazolo[1,5-a]pyrazine.

2. The compound according to claim 1, wherein
$R^1$ denotes —CH$_2$—R$^3$;
$R^2$ denotes Ar$^e$ or Hetar$^2$; and
$R^3$ denotes Ar$^3$ or Hetar$^3$.

3. The compound according to claim 2, wherein
Ar$^2$ denotes phenyl which is unsubstituted or substituted with one or two identical or different substituents selected from the group consisting of methyl, ethyl, n-propyl, iso-propyl, n-butyl, tert-butyl, methoxy, ethoxy, n-propoxy, iso-propoxy, n-butoxy, tert-butoxy, —N,N-(di-methyl)amino, F, Cl, Br, —O—CH$_2$—O— and —O—CH$_2$—CH$_2$—O—;

or

Hetar$^2$ denotes an aromatic monocyclic heterocycle which is selected from the group consisting of pyridin-2-yl, pyridin-4-yl, thien-2-yl, and pyrazol-4-yl, wherein said heterocycle is unsubstituted or substituted with one or two identical or different substituents selected from the group consisting of phenyl, —CH$_2$-phenyl, methyl, ethyl, iso-propyl, tert-butyl, and cyclopropyl.

4. The compound according to claim 3, wherein
Ar$^2$ denotes a phenyl which is selected from the group consisting of phenyl, 3-methyl-phenyl, 4-ethyl-phenyl, 4-(iso-propyl)-phenyl, 4-methoxy-phenyl, 2,5-dimethoxy-phenyl, 4-ethoxy-phenyl, 4-(iso-propoxy)-phenyl, 4-(n-butoxy)-phenyl, 4-(N,N-dimethyl)amino-phenyl, 2-fluoro-phenyl, 3-fluoro-phenyl, 4-fluoro-phenyl, 2,3-difluoro-phenyl, 2,4-difluoro-phenyl, 2,5-difluoro-phenyl, 3,5-difluoro-phenyl, 4-chloro-phenyl, 3-bromo-phenyl, 2,3-dihydro-benzo[1,4]dioxin-6-yl, and benzo[1,3]dioxol-5-yl;

or

Hetar$^2$ denotes an aromatic monocyclic heterocycle which is selected from the group consisting of pyridin-2-yl, pyridin-4-yl, thien-2-yl, 3-cyclopropyl-1-methyl-1H-pyrazol-4-yl, 3-cyclopropyl-1 ethyl-1H-pyrazol-4-yl, 1-phenyl-3-(iso-propyl)-1H-pyrazol-4-yl, 1-methyl-3-(iso-propyl)-1H-pyrazol-4-yl, 1-benzyl-3-(iso-propyl)-1H-pyrazol-4-yl, and 1-benzyl-3-(tert-butyl)-1H-pyrazol-4-yl.

5. The compound according to claim 2, wherein
Ar$^3$ denotes phenyl which is unsubstituted or substituted with one or two identical or different substituents selected from the group consisting of methyl, methoxy, ethoxy, iso-propoxy, —N,N-(di-methyl)amino, F, Cl, Br and —O—CH$_2$—O—;

or

Hetar$^3$ denotes a heterocycle which is selected from the group consisting of pyridin-2-yl, pyridin-3-yl, pyridin-4-yl, fur-2-yl, thien-2-yl, pyrazol-3-yl, pyrazol-4-yl, pyrazol-5-yl, and pyrazolo[1,5-a]pyridin-3-yl, wherein said heterocycle is unsubstituted or substituted with one or two identical or different substituents selected from the group consisting of phenyl, —CH$_2$— phenyl, methyl, ethyl, and iso-propyl.

6. The compound according to claim 5, wherein
Ar$^3$ denotes a phenyl which is selected from the group consisting of phenyl, 3-methyl-phenyl, 3-methoxy-phenyl, 4-methoxy-phenyl, 2,4-dimethoxy-phenyl, 2,5-dimethoxy-phenyl, 4-ethoxy-phenyl, 4-(iso-propoxy)-phenyl, 4-(N,N-dimethyl)amino-phenyl, 2-fluoro-phenyl, 3-fluoro-phenyl, 4-fluoro-phenyl, 2,3-difluoro-phenyl, 2,4-difluoro-phenyl, 2,5-difluoro-phenyl, 3-chloro-phenyl, 4-chloro-phenyl, 3-bromo-phenyl, 4-bromo-phenyl, and benzo[1,3]dioxol-5-yl;

or

Hetar$^3$ denotes a heterocycle which is selected from the group consisting of pyridin-3-yl, pyridin-4-yl, 5-methyl-fur-2-yl, thien-2-yl, 1-methyl-1H-pyrazol-3-yl, 1,3-dimethyl-1H-pyrazol-4-yl, 1,5-dimethyl-1H-pyrazol-4-yl, 1-ethyl-1H-pyrazol-4-yl, 1-benzyl-1H-pyrazol-4-yl, 1-phenyl-3-(iso-propyl)-1H-pyrazol-4-yl, 2H-pyrazol-3-yl, and pyrazolo[1,5-a]pyridin-3-yl.

7. The compound according claim 2, wherein
Ar$^2$ denotes a phenyl which is selected from the group consisting of phenyl, 3-methyl-phenyl, 4-ethyl-phenyl, 4-(iso-propyl)-phenyl, 4-methoxy-phenyl, 2,5-dimethoxy-phenyl, 4-ethoxy-phenyl, 4-(iso-propoxy)-phenyl, 4-(n-butoxy)-phenyl, 4-(N,N-dimethyl)amino-phenyl, 2-fluoro-phenyl, 3-fluoro-phenyl, 4-fluoro-phenyl, 2,3-difluoro-phenyl, 2,4-difluoro-phenyl, 2,5-difluoro-phenyl, 3,5-difluoro-phenyl, 4-chloro-phenyl, 3-bromo-phenyl, and 2,3-dihydro-benzo[1,4]dioxin-6-yl;

or

Hetar$^2$ denotes a heterocycle which is selected from the group consisting of thien-2-yl, 3-cyclopropyl-1-ethyl-1H-pyrazol-4-yl, 1-phenyl-3-(iso-propyl)-1H-pyrazol-4-yl, 1-benzyl-3-(iso-propyl)-1H-pyrazol-4-yl, and 1-benzyl-3-(tert-butyl)-1H-pyrazol-4-yl;

and

Ar$^3$ denotes a phenyl which is selected from the group consisting of phenyl, 3-methyl-phenyl, 4-ethoxy-phenyl, 4-(N,N-dimethyl)amino-phenyl, 2-fluoro-phenyl, 3-fluoro-phenyl, 4-fluoro-phenyl, 2,3-difluoro-phenyl, 3-chloro-phenyl, 4-chloro-phenyl, 3-bromo-phenyl, 4-bromo-phenyl, and benzo[1,3]dioxol-5-yl;

or

Hetar$^3$ denotes a heterocycle which is selected from the group consisting of pyridin-4-yl, thien-2-yl, 1-benzyl-1H-pyrazol-4-yl, 1-phenyl-3-(iso-propyl)-1H-pyrazol-4-yl, 2H-pyrazol-3-yl, 1H-pyrazol-5-yl, and pyrazolo[1,5-a]pyridin-3-yl.

8. The compound according to claim 7, wherein
Ar$^2$ denotes a phenyl which is selected from the group consisting of phenyl, 3-methyl-phenyl, 4-ethyl-phenyl, 4-(iso-propyl)-phenyl, 4-(iso-propoxy)-phenyl, 4-(n-butoxy)-phenyl, 4-(N,N-dimethyl)amino-phenyl, 3-fluoro-phenyl, 4-fluoro-phenyl, 2,5-difluoro-phenyl, 3,5-difluoro-phenyl, 4-chloro-phenyl, 3-bromo-phenyl, and 2,3-dihydro-benzo[1,4]dioxin-6-yl;

or

Hetar$^2$ denotes 1-phenyl-3-(iso-propyl)-1H-pyrazol-4-yl;

and

Ar$^3$ denotes a phenyl which is selected from the group consisting of phenyl, 3-methyl-phenyl, 4-ethoxy-phenyl, 3-fluoro-phenyl, 4-fluoro-phenyl, 2,3-difluoro-phenyl, 3-chloro-phenyl, 3-bromo-phenyl, and benzo[1,3]dioxol-5-yl;

or

Hetar$^3$ is denotes thien-2-yl.

9. The compound according to claim 1, wherein
$Ar^2$ and $Ar^3$ denote independently phenyl which is unsubstituted or substituted with one or two identical or different substituents selected from the group consisting of $C_{1-4}$-alkyl, $C_{1-4}$-alkoxy, —N,N-(di-$C_{1-6}$-alkyl) amino, F, Cl, Br, —O—CH$_2$—O— and —O—CH$_2$—CH$_2$—O—;

$Hetar^2$ denotes an aromatic monocyclic 5- to 6-membered heterocycle having 1 or 2 heteroatoms selected from the group consisting of nitrogen and sulfur, which heterocycle is unsubstituted or substituted with one or more identical or different substituents selected from the group consisting of $C_{1-4}$-alkyl, cyclopropyl, phenyl and —CH$_2$-phenyl wherein phenyl is unsubstituted or substituted with one or two identical or different substituents selected from the group consisting of $C_{1-6}$-alkyl, $C_{1-6}$-alkoxy and halogen;

$Hetar^3$ denotes an aromatic monocyclic 5- to 6-membered or a bicyclic 8- to 9-membered heterocycle having 1 or 2 heteroatoms selected from the group consisting of nitrogen, oxygen and sulfur, which heterocycle is unsubstituted or substituted with one or more identical or different substituents selected from the group consisting of $C_{1-4}$-alkyl, cyclopropyl, phenyl and —CH$_2$— phenyl wherein phenyl is unsubstituted or substituted with one or two identical or different substituents selected from the group consisting of $C_{1-6}$-alkyl, $C_{1-6}$-alkoxy and halogen.

10. The compound according to claim 1, wherein the compound is a stereoisomer, wherein the stereoisomer is an enantiomeric mixture consisting of formula (R)-(Ia) and formula (S)-(Ia):

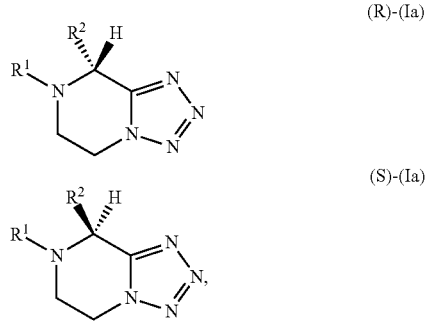

wherein:
  (i) the enantiomer of formula (R)-(Ia) is present in at least 90%; or
  (ii) the enantiomer of formula (S)-(Ia) is present in at least 90%.

11. The compound according to claim 1, selected from the group consisting of
  7-(2,5-Dimethoxy-benzyl)-8-(4-isopropoxy-phenyl)-5,6,7,8-tetrahydro-tetrazolo[1,5-a]pyrazine,
  7-(2-Fluoro-benzyl)-8-(4-isopropoxy-phenyl)-5,6,7,8-tetrahydro-tetrazolo[1,5-a]pyrazine,
  7-Cyclohexylmethyl-8-(4-isopropoxy-phenyl)-5,6,7,8-tetrahydro-tetrazolo[1,5-a]pyrazine,
  7-(2-Fluoro-benzyl)-8-(4-methoxy-phenyl)-5,6,7,8-tetrahydro-tetrazolo[1,5-a]pyrazine,
  7-(3-Isopropyl-1-phenyl-1H-pyrazol-4-ylmethyl)-8-(4-methoxy-phenyl)-5,6,7,8-tetrahydro-tetrazolo[1,5-a]pyrazine,
  7-(3-Bromo-benzyl)-8-(3-bromo-phenyl)-5,6,7,8-tetrahydro-tetrazolo[1,5a]pyrazine,
  7-(3-Bromo-benzyl)-8-(2,3-difluoro-phenyl)-5,6,7,8-tetrahydro-tetrazolo[1,5-a]pyrazine,
  8-(3-Bromo-phenyl)-7-thiophen-2-ylmethyl-5,6,7,8-tetrahydro-tetrazolo[1,5-a]pyrazine,
  8-(3-Bromo-phenyl)-7-(3-isopropyl-1-phenyl-1H-pyrazol-4-ylmethyl)-5,6,7,8-tetrahydro-tetrazolo[1,5-a]pyrazine,
  8-(3-Bromo-phenyl)-7-cyclohexylmethyl-5,6,7,8-tetrahydro-tetrazolo[1,5a]pyrazine,
  8-(3-Bromo-phenyl)-7-(2,3-difluoro-benzyl)-5,6,7,8-tetrahydro-tetrazolo[1,5-a]pyrazine,
  8-(4-Fluoro-phenyl)-7-(3-isopropyl-1-phenyl-1H-pyrazol-4-ylmethyl)-5,6,7,8-tetrahydro-tetrazolo[1,5-a]pyrazine,
  8-(2,5-Dimethoxy-phenyl)-7-(4-isopropoxy-benzyl)-5,6,7,8-tetrahydro-tetrazolo[1,5-a]pyrazine,
  8-(2,5-Dimethoxy-phenyl)-7-(3-isopropyl-1-phenyl-1H-pyrazol-4-ylmethyl)-5,6,7,8-tetrahydro-tetrazolo[1,5a]pyrazine,
  {4-[7-(2-Fluoro-benzyl)-5,6,7,8-tetrahydro-tetrazolo[1,5-a]pyrazin-8-yl]-phenyl}-dimethyl-amine,
  [4-(7-Benzo[1,3]dioxol-5-ylmethyl-5,6,7,8-tetrahydro-tetrazolo[1,5-a]pyrazin-8-yl)-phenyl]-dimethyl-amine,
  {4-[7-(2,5-Difluoro-benzyl)-5,6,7,8-tetrahydro-tetrazolo[1,5-a]pyrazin-8-yl]-phenyl}-dimethyl-amine,
  {4-[7-(3-Fluoro-benzyl)-5,6,7,8-tetrahydro-tetrazolo[1,5-a]pyrazin-8-yl]-phenyl}-dimethyl-amine,
  {4-[7-(3-Isopropyl-1-phenyl-1H-pyrazol-4-ylmethyl)-5,6,7,8-tetrahydro-tetrazolo[1,5-a]pyrazin-8-yl]-phenyl}-dimethyl-amine,
  [4-(7-Cyclohexylmethyl-5,6,7,8-tetrahydro-tetrazolo[1,5-a]pyrazin-8-yl)-phenyl]-dimethyl-amine,
  {4-[7-(2,3-Difluoro-benzyl)-5,6,7,8-tetrahydro-tetrazolo[1,5-a]pyrazin-8-yl]-phenyl}-dimethyl-amine,
  8-(2-Fluoro-phenyl)-7-(4-isopropoxy-benzyl)-5,6,7,8-tetrahydro-tetrazolo[1,5-a]pyrazine,
  8-(2-Fluoro-phenyl)-7-(4-methoxy-benzyl)-5,6,7,8-tetrahydro-tetrazolo[1,5-a]pyrazine,
  {4-[8-(2-Fluoro-phenyl)-5,6-dihydro-8H-tetrazolo[1,5-a]pyrazin-7-ylmethyl]-phenyl}-dimethyl-amine,
  7-(2,5-Difluoro-benzyl)-8-(2-fluoro-phenyl)-5,6,7,8-tetrahydro-tetrazolo[1,5-a]pyrazine,
  8-(2-Fluoro-phenyl)-7-(3-isopropyl-1-phenyl-1H-pyrazol-4-ylmethyl)-5,6,7,8-tetrahydro-tetrazolo[1,5-a]pyrazine,
  7-(2,3-Difluoro-benzyl)-8-(2-fluoro-phenyl)-5,6,7,8-tetrahydro-tetrazolo[1,5-a]pyrazine,
  7-(3-Isopropyl-1-phenyl-1H-pyrazol-4-ylmethyl)-8-m-tolyl-5,6,7,8-tetrahydro-tetrazolo[1,5-a]pyrazine,
  [4-(8-Benzo[1,3]dioxol-5-yl-5,6-dihydro-8H-tetrazolo[1,5-a]pyrazin-7-ylmethyl)-phenyl]-dimethyl-amine,
  8-Benzo[1,3]dioxol-5-yl-7-(3-isopropyl-1-phenyl-1H-pyrazol-4-ylmethyl)-5,6,7,8-tetrahydro-tetrazolo[1,5-a]pyrazine,
  {4-[8-(2,5-Difluoro-phenyl)-5,6-dihydro-8H-tetrazolo[1,5-a]pyrazin-7-ylmethyl]-phenyl}-dimethyl-amine,
  8-(2,5-Difluoro-phenyl)-7-(2-fluoro-benzyl)-5,6,7,8-tetrahydro-tetrazolo[1,5-a]pyrazine,
  7-(2,5-Difluoro-benzyl)-8-(2,5-difluoro-phenyl)-5,6,7,8-tetrahydro-tetrazolo[1,5-a]pyrazine,
  8-(2,5-Difluoro-phenyl)-7-(3-fluoro-benzyl)-5,6,7,8-tetrahydro-tetrazolo[1,5-a]pyrazine,
  8-(2,5-Difluoro-phenyl)-7-(3-isopropyl-1-phenyl-1H-pyrazol-4-ylmethyl)-5,6,7,8-tetrahydro-tetrazolo[1,5-a]pyrazine, 7-(2,3-Difluoro-benzyl)-8-(2,5-difluoro-phenyl)-5,6,7,8-tetrahydro-tetrazolo[1,5-a]pyrazine,
{4-[8-(3-Fluoro-phenyl)-5,6-dihydro-8H-tetrazolo[1,5-a]pyrazin-7-ylmethyl]-phenyl}-dimethyl-amine,
7-(2,5-Difluoro-benzyl)-8-(3-fluoro-phenyl)-5,6,7,8-tetrahydro-tetrazolo[1,5-a]pyrazine,
7-(3-Fluoro-benzyl)-8-(3-fluoro-phenyl)-5,6,7,8-tetrahydro-tetrazolo[1,5-a]pyrazine,
7-(4-Chloro-benzyl)-8-(3-fluoro-phenyl)-5,6,7,8-tetrahydro-tetrazolo[1,5-a]pyrazine,
8-(3-Fluoro-phenyl)-7-(3-isopropyl-1-phenyl-1H-pyrazol-4-ylmethyl)-5,6,7,8-tetrahydro-tetrazolo[1,5-a]pyrazine,
7-(2,3-Difluoro-benzyl)-8-(3-fluoro-phenyl)-5,6,7,8-tetrahydro-tetrazolo[1,5-a]pyrazine,
8-(4-Chloro-phenyl)-7-(3-fluoro-benzyl)-5,6,7,8-tetrahydro-tetrazolo[1,5-a]pyrazine,
8-(4-Ethoxy-phenyl)-7-(3-isopropyl-1-phenyl-1H-pyrazol-4-ylmethyl)-5,6,7,8-tetrahydro-tetrazolo[1,5-a]pyrazine,
7-Cyclohexylmethyl-8-(4-ethoxy-phenyl)-5,6,7,8-tetrahydro-tetrazolo[1,5-a]pyrazine,
7-(2,3-Difluoro-benzyl)-8-(4-ethoxy-phenyl)-5,6,7,8-tetrahydro-tetrazolo[1,5-a]pyrazine,
7-(4-Bromo-benzy-8-thiophen-2-yl-5,6,7,8-tetrahydro-tetrazolol[1,5-a]pyrazine,
8-Thiophen-2-yl-7-thiophen-2-ylmethyl-5,6,7,8-tetrahydro-tetrazolo[1,5-a]pyrazine,
7-(3-Isopropyl-1-phenyl-H-pyrazol-4-ylmethyl)-8-thiophen-2-yl-5,6,7,8-tetrahydro-tetrazolo[1,5-a]pyrazine,
7-Cyclohexylmethyl-8-thiophen-2-yl-5,6,7,8-tetrahydro-tetrazolo[1,5-a]pyrazine,
7-(2,3-Difluoro-benzyl)-8-thiophen-2-yl-5,6,7,8-tetrahydro-tetrazolo[1,5-a]pyrazine,
8-(3-Isopropyl-1-phenyl-1H-pyrazol-4-yl)-7-(4-methoxy-benzyl)-5,6,7(8-tetrahydro-tetrazolo[1,5-a]pyrazine,
7-(4-Bromo-benzyl)-8-(3-isopropyl-1-phenyl-1H-pyrazol-4-yl)-5,6,7,8-tetrahydro-tetrazolo[1,5-a]pyrazine,
7-(4-Fluoro-benzyl)-8-(3-isopropyl-1-phenyl-1H-pyrazol-4-yl)-5,6,7,8-tetrahydro-tetrazolo[1,5-a]pyrazine,
7-(2,5-Dimethoxy-benzyl)-8-(3-isopropyl-1-phenyl-1H-pyrazol-4-yl)-5,6,7,8-tetrahydro-tetrazolo[1,5-a]pyrazine,
{4-[8-(3-Isopropyl-1-phenyl-1H-pyrazol-4-yl)-5,6-dihydro-8H-tetrazolo[1,5-a]pyrazin-7-ylmethyl]-phenyl}-dimethyl-amine,
7-(2-Fluoro-benzyl)-8-(3-isopropyl-1-phenyl-1H-pyrazol-4-yl)-5,6,7,8-tetrahydro-tetrazolo[1,5-a]pyrazine,
8-(3-Isopropyl-1-phenyl-1H-pyrazol-4-yl)-7-(3-methyl-benzyl)-5,6,7,8-tetrahydro-tetrazolo[1,5-a]pyrazine,
7-Benzo[1,3]dioxol-5-ylmethyl-8-(3-isopropyl-1-phenyl-1H-pyrazol-4-yl)-5,6,7,8-tetrahydro-tetrazolo[1,5-a]pyrazine,
7-(2,5-Difluoro-benzyl)-8-(3-isopropyl-1-phenyl-1H-pyrazol-4-yl)-5,6,7,8-tetrahydro-tetrazolo[1,5-a]pyrazine,
7-(4-Ethoxy-benzyl)-8-(3-isopropyl-1-phenyl-1H-pyrazol-4-yl)-5,6,7,8-tetrahydro-tetrazolo[1,5-a]pyrazine,
8-(3-Isopropyl-1-phenyl-1H-pyrazol-4-yl)-7-thiophen-2-ylmethyl-5,6,7,8-tetrahydro-tetrazolo[1,5-a]pyrazine,
8-(3-Isopropyl-1-phenyl-1H-pyrazol-4-yl)-7-(3-isopropyl-1-phenyl-1H-pyrazol-4-ylmethyl)-5,6,7,8-tetrahydro-tetrazolo[1,5-a]pyrazine,
7-(2,3-Difluoro-benzyl)-8-(3-isopropyl-1-phenyl-1H-pyrazol-4-yl)-5,6,7,8-tetrahydro-tetrazolo[1,5-a]pyrazine,
8-Cyclohexyl-7-(4-isopropoxy-benzyl)-5,6,7,8-tetrahydro-tetrazolo[1,5-a]pyrazine,
7-(3-Bromo-benzyl)-8-cyclohexyl-5,6,7,8-tetrahydro-tetrazolo[1,5-a]pyrazine,
[4-(8-Cyclohexyl-5,6-dihydro-8H-tetrazolo[1,5-a]pyrazin-7-ylmethyl)-phenyl]-dimethyl-amine,
8-Cyclohexyl-7-(4-ethoxy-benzyl)-5,6,7,8-tetrahydro-tetrazolo[1,5-a]pyrazine,
8-Cyclohexyl-7-thiophen-2-ylmethyl-5,6,7,8-tetrahydro-tetrazolo[1,5-a]pyrazine,
8-Cyclohexyl-7-cyclohexylmethyl-5,6,7,8-tetrahydro-tetrazolo[1,5-a]pyrazine,
7-(3-Bromo-benzyl)-8-(2,3-difluoro-phenyl)-5,6,7,8-tetrahydro-tetrazolo[1,5-a]pyrazine,
8-(2,3-Difluoro-phenyl)-7-(2,5-dimethoxy-benzyl)-5,6,7,8-tetrahydro-tetrazolo[1,5-a]pyrazine,
{4-[8-(2,3-Difluoro-phenyl)-5,6-dihydro-8H-tetrazolo[1,5-a]pyrazin-7-ylmethyl]-phenyl}-dimethyl-amine,
8-(2,3-Difluoro-phenyl)-7-(2-fluoro-benzyl)-5,6,7,8-tetrahydro-tetrazolo[1,5-a]pyrazine,
7-(2,5-Difluoro-benzyl)-8-(2,3-difluoro-phenyl)-5,6,7,8-tetrahydro-tetrazolo[1,5-a]pyrazine,
8-(2,3-Difluoro-phenyl)-7-(3-fluoro-benzyl)-5,6,7,8-tetrahydro-tetrazolo[1,5-a]pyrazine,
8-(2,3-Difluoro-phenyl)-7-(4-ethoxy-benzyl)-5,6,7,8-tetrahydro-tetrazolo[1,5-a]pyrazine,
8-(2,3-Difluoro-phenyl)-7-thiophen-2-ylmethyl-5,6,7,8-tetrahydro-tetrazolo[1,5-a]pyrazine,
8-(2,3-Difluoro-phenyl)-7-(3-isopropyl-1-phenyl-1H-pyrazol-4-ylmethyl)-5,6,7,8-tetrahydro-tetrazolo[1,5-a]pyrazine,
7-(2,3-Difluoro-benzyl)-8-(2,3-difluoro-phenyl)-5,6,7,8-tetrahydro-tetrazolo[1,5-a]pyrazine,
7-(2,4-Dimethoxy-benzyl)-8-(3-fluoro-phenyl)-5,6,7,8-tetrahydro-tetrazolo[1,5-a]pyrazine,
8-(3-Fluoro-phenyl)-5,6,7,8-tetrahydro-tetrazolo[1,5-a]pyrazine,
(3-Bromo-phenyl)-[8-(3-fluoro-phenyl)-5,6-dihydro-8H-tetrazolo[1,5-a]pyrazin-7-yl]-methanone,
8-(4-Fluoro-phenyl)-7-pyridin-3-ylmethyl-5,6,7,8-tetrahydro-tetrazolo[1,5-a]pyrazine,
8-(4-Fluoro-phenyl)-7-pyridin-4-ylmethyl-5,6,7,8-tetrahydro-tetrazolo[1,5-a]pyrazine,
8-(4-Fluoro-phenyl)-7-(1-methyl-1H-pyrazol-3-ylmethyl)-5,6,7,8-tetrahydro-tetrazolo[1,5-a]pyrazine,
7-(3-Methyl-benzyl)-8-pyridin-2-yl-5,6,7,8-tetrahydro-tetrazolo[1,5-a]pyrazine,
7-(3-Methyl-benzyl)-8-pyridin-4-yl-5,6,7,8-tetrahydro-tetrazolo[1,5-a]pyrazine,
7-Benzyl-8-(4-isopropoxy-phenyl)-5,6,7,8-tetrahydro-tetrazolo[1,5-a]pyrazine,
7-Benzyl-8-(3-fluoro-phenyl)-5,6,7,8-tetrahydro-tetrazolo[1,5-a]pyrazine,
7-Benzyl-8-(4-ethyl-phenyl)-5,6,7,8-tetrahydro-tetrazolo[1,5-a]pyrazine,
7-(4-Fluoro-benzyl)-8-(3-fluoro-phenyl)-5,6,7,8-tetrahydro-tetrazolo[1,5-a]pyrazine,
7-(3-Bromo-benzyl)-8-m-tolyl-5,6,7,8-tetrahydro-tetrazolo[1,5-a]pyrazine,
8-(4-Fluoro-phenyl)-7-(3-methyl-benzyl)-5,6,7,8-tetrahydro-tetrazolo[1,5-a]pyrazine,
7-Benzyl-8-(3-bromo-phenyl)-5,6,7,8-tetrahydro-tetrazolo[1,5-a]pyrazine,
8-(2,3-Dihydro-benzo[1,4]dioxin-6-yl-7-methyl-benzyl)-5,6,7,8-tetrahydro-tetrazolo[1,5-a]pyrazine,
7-(3-Bromo-benzyl)-8-(4-fluoro-phenyl)-5,6,7,8-tetrahydro-tetrazolo[1,5-a]pyrazine, 8-(4-Chloro-phenyl)-7-(3-methyl-benzyl)-5,6,7,8-tetrahydro-tetrazolo[1,5-a]pyrazine,
7-(2,3-Difluoro-benzyl)-8-(2,5-dimethoxy-phenyl)-5,6,7,8-tetrahydro-tetrazolo[1,5-a]pyrazine,
7-Benzyl-8-(4-butoxy-phenyl)-5,6,7,8-tetrahydro-tetrazolo[1,5-a]pyrazine,
8-(4-Isopropoxy-phenyl)-7-(3-methyl-benzyl)-5,6,7,8-tetrahydro-tetrazolo[1,5-a]pyrazine,
7-Benzyl-8-m-tolyl-5,6,7,8-tetrahydro-tetrazolo[1,5-a]pyrazine,
7-Benzyl-8-(3,5-difluoro-phenyl)-5,6,7,8-tetrahydro-tetrazolo[1,5-a]pyrazine,
7-Benzyl-8-(4-fluoro-phenyl)-5,6,7,8-tetrahydro-tetrazolo[1,5-a]pyrazine,
8-(4-Butoxy-phenyl)-7-(3-methyl-benzyl)-5,6,7,8-tetrahydro-tetrazolo[1,5-a]pyrazine,
7-(3-Bromo-benzyl)-8-(4-isopropyl-phenyl)-5,6,7,8-tetrahydro-tetrazolo[1,5-a]pyrazine,
7-(3-Methyl-benzyl)-8-phenyl-5,6,7,8-tetrahydro-tetrazolo[1,5-a]pyrazine,
8-(4-Chloro-phenyl)-7-thiophen-2-ylmethyl-5,6,7,8-tetrahydro-tetrazolo[1,5-a]pyrazine,
7-(3-Bromo-benzyl)-8-(3,5-difluoro-phenyl)-5,6,7,8-tetrahydro-tetrazolo[1,5-a]pyrazine,
7-(3-Bromo-benzyl)-8-(2,5-difluoro-phenyl)-5,6,7,8-tetrahydro-tetrazolo[1,5-a]pyrazine,
{4-[7-(3-Bromo-benzyl)-5,6,7,8-tetrahydro-tetrazolo[1,5-a]pyrazin-8-yl]-phenyl}-dimethyl-amine,
7-(3-Bromo-benzyl)-8-(4-isopropoxy-phenyl)-5,6,7,8-tetrahydro-tetrazolo[1,5-a]pyrazine,
7-Benzyl-8-(4-chloro-phenyl)-5,6,7,8-tetrahydro-tetrazolo[1,5-a]pyrazine,
7-Benzyl-8-(2,5-difluoro-phenyl)-5,6,7,8-tetrahydro-tetrazolo[1,5-a]pyrazine,
7-Benzyl-8-(2,3-difluoro-phenyl)-5,6,7,8-tetrahydro-tetrazolo[1,5-a]pyrazine,
7-Cyclohexyl-8-(3-isopropyl-1-phenyl-1H-pyrazol-4-yl)-5,6,7,8-tetrahydro-tetrazolo[1,5-a]pyrazine,
7-(3-Bromo-benzyl)-8-(4-ethoxy-phenyl)-5,6,7,8-tetrahydro-tetrazolo[1,5-a]pyrazine,
8-3-Fluoro-phenyl-7-(3-methyl-benzyl)-5,6,7,8-tetrahydro-tetrazolo[1,5-a]pyrazine,
8-3-Fluoro-phenyl-7-(thiophen-2-ylmethyl)-5,6,7,8-tetrahydro-tetrazolo[1,5-a]pyrazine,
8-(4-Ethoxy-phenyl)-7-(3-methyl-benzyl)-5,6,7,8-tetrahydro-tetrazolo[1,5-a]pyrazine,
7-(3-Bromo-benzyl)-8-(2-fluoro-phenyl)-5,6,7,8-tetrahydro-tetrazolo[1,5-a]pyrazine,
7-(3-Bromo-benzyl)-8-(4-methoxy-phenyl)-5,6,7,8-tetrahydro-tetrazolo[1,5-a]pyrazine,
8-(4-Isopropoxy-phenyl)-7-thiophen-2-ylmethyl-5,6,7,8-tetrahydro-tetrazolo[1,5-a]pyrazine,
7-Benzyl-8-(4-methoxy-phenyl)-5,6,7,8-tetrahydro-tetrazolo[1,5-a]pyrazine,
7-(3-Bromo-benzyl)-8-phenyl-5,6,7,8-tetrahydro-tetrazolo[1,5-a]pyrazine,
8-(3,5-Difluoro-phenyl)-7-thiophen-2-ylmethyl-5,6,7,8-tetrahydro-tetrazolo[1,5-a]pyrazine,
8-(4-Fluoro-phenyl)-7-thiophen-2-ylmethyl-5,6,7,8-tetrahydro-tetrazolo[1,5-a]pyrazine,
{4-[7-(4-Fluoro-benzyl)-5,6,7,8-tetrahydro-tetrazolo[1,5-a]pyrazin-8-yl]-phenyl}-dimethyl-amine,
7-Benzyl-8-phenyl-5,6,7,8-tetrahydro-tetrazolo[1,5-a]pyrazine,
8-(2,5-Dimethoxy-phenyl)-7-(4-fluoro-benzyl)-5,6,7,8-tetrahydro-tetrazolo[1,5-a]pyrazine,
Dimethyl-{4-[7-(3-methyl-benzyl)-5,6,7,8-tetrahydro-tetrazolo[1,5-a]pyrazin-8-yl]-phenyl}-amine,
8-(4-Butoxy-phenyl)-7-(2-fluoro-benzyl)-5,6,7,8-tetrahydro-tetrazolo[1,5-a]pyrazine,
7-Benzo[1,3]dioxol-5-ylmethyl-8-(4-isopropoxy-phenyl)-5,6,7,8-tetrahydro-tetrazolo[1,5-a]pyrazine,
7-(4-Fluoro-benzyl)-8-(4-isopropoxy-phenyl)-5,6,7,8-tetrahydro-tetrazolo[1,5-a]pyrazine,
8-(2,3-Dihydro-benzo[1,4]dioxin-6-yl)-7-(4-fluoro-benzyl)-5,6,7,8-tetrahydro-tetrazolo[1,5-a]pyrazine,
8-(4-Ethoxy-phenyl)-7-(4-fluoro-benzyl)-5,6,7,8-tetrahydro-tetrazolo[1,5-a]pyrazine,
7-Benzyl-8-(2,5-dimethoxy-phenyl)-5,6,7,8-tetrahydro-tetrazolo[1,5-a]pyrazine,
8-(2,4-Difluoro-phenyl)-7-(3-methyl-benzyl)-5,6,7,8-tetrahydro-tetrazolo[1,5-a]pyrazine,
8-(2-Fluoro-phenyl)-7-thiophen-2-ylmethyl-5,6,7,8-tetrahydro-tetrazolo[1,5-a]pyrazine,
8-(4-Chloro-phenyl)-7-(2-fluoro-benzyl)-5,6,7,8-tetrahydro-tetrazolo[1,5-a]pyrazine,
8-Phenyl-7-thiophen-2-ylmethyl-5,6,7,8-tetrahydro-tetrazolo[1,5-a]pyrazine,
8-(2,5-Difluoro-phenyl)-7-thiophen-2-ylmethyl-5,6,7,8-tetrahydro-tetrazolo[1,5-a]pyrazine,
8-(2,5-Dimethoxy-phenyl)-7-(2-fluoro-benzyl)-5,6,7,8-tetrahydro-tetrazolo[1,5-a]pyrazine,
8-(4-Isopropoxy-phenyl)-7-(5-methyl-furan-2-ylmethyl)-5,6,7,8-tetra hydro-tetrazolo[1,5-a]pyrazine,
7-(3-Chloro-benzyl)-8-(3-isopropyl-1-phenyl-1H-pyrazol-4-yl)-5,6,7,8-tetrahydro-tetrazolo[1,5-a]pyrazine,
8-(3-Cyclopropyl-1-ethyl-1H-pyrazol-4-yl)-7-thiophen-2-ylmethyl-5,6,7,8-tetrahydro-tetrazolo[1,5-a]pyrazine,
8-(3-Isopropyl-1-methyl-1H-pyrazol-4-yl)-7-thiophen-2-ylmethyl-5,6,7,8-tetrahydro-tetrazolo[1,5-a]pyrazine,
7-(4-Fluoro-benzyl)-8-(4-methoxy-phenyl)-5,6,7,8-tetrahydro-tetrazolo[1,5-a]pyrazine,
7-(3-Methoxy-benzyl)-8-(4-methoxy-phenyl)-5,6,7,8-tetrahydro-tetrazolo[1,5-a]pyrazine,
7-(4-Chloro-benzyl)-8-(3-isopropyl-1-phenyl-1H-pyrazol-4-yl)-5,6,7,8-tetrahydro-tetrazolo[1,5-a]pyrazine,
{4-[7-(4-Isopropoxy-benzyl)-5,6,7,8-tetrahydro-tetrazolo[1,5-a]pyrazin-8-yl]-phenyl}-dimethyl-amine,
7-Benzyl-8-(3-isopropyl-1-phenyl-1H-pyrazol-4-yl)-5,6,7,8-tetrahydro-tetrazolo[1,5-a]pyrazine,
7-Benzyl-8-(4-ethyl-phenyl)-8-methyl-5,6,7,8-tetra hydro-tetrazolo[1,5-a]pyrazine,
8-(3-Isopropyl-1-phenyl-1H-pyrazol-4-yl)-7-(2H-pyrazol-3-ylmethyl)-5,6,7,8-tetrahydro-tetrazolo[1,5-a]pyrazine,
8-(3-Isopropyl-1-phenyl-1H-pyrazol-4-yl)-7-pyrazolo[1,5-a]pyridin-3-ylmethyl-5,6,7,8-tetrahydro-tetrazolo[1,5-a]pyrazine,
7-(1-Ethyl-1H-pyrazol-4-ylmethyl)-8-(3-isopropyl-1-phenyl-1H-pyrazol-4-yl)-5,6,7,8-tetrahydro-tetrazolo[1,5-a]pyrazine,
7-(1,5-Dimethyl-1H-pyrazol-4-ylmethyl)-8-(3-isopropyl-1-phenyl-1H-pyrazol-4-yl)-5,6,7,8-tetrahydro-tetrazolo[1,5-a]pyrazine,
8-(3-Isopropyl-1-phenyl-1H-pyrazol-4-yl)-7-(1,3,5-trimethyl-1H-pyrazol-4-ylmethyl)-5,6,7,8-tetrahydro-tetrazolo[1,5-a]pyrazine,
7-(2-Chloro-benzyl)-8-(3-isopropyl-1-phenyl-1H-pyrazol-4-yl)-5,6,7,8-tetrahydro-tetrazolo[1,5-a]pyrazine,
8-(3-Cyclopropyl-1-methyl-1H-pyrazol-4-yl)-7-thiophen-2-ylmethyl-5,6,7,8-tetrahydro-tetrazolo[1,5-a]pyrazine, 8-(1-Benzyl-3-tert-butyl-1H-pyrazo-4-yl)-7-thiophen-2-ylmethyl-5,6,7,8-tetrahydro-tetrazolo[1,5-a]pyrazine,
7-(1-Benzyl-1H-pyrazol-4-ylmethyl)-8-(3-isopropyl-1-phenyl-1H-pyrazol-4-yl)-5,6,7,8-tetrahydro-tetrazolo[1,5-a]pyrazine,
8-(1-Benzyl-3-isopropyl-1H-pyrazol-4-yl)-7-thiophen-2-ylmethyl-5,6,7,8-tetrahydro-tetrazolo[1,5-a]pyrazine,
7-(3-Bromo-benzyl)-8-(3-fluoro-phenyl)-5,6,7,8-tetrahydro-tetrazolo[1,5-a]pyrazine,
[4-(7-Benzyl-5,6,7,8-tetrahydro-tetrazolo[1,5-a]pyrazin-8-yl)-phenyl]-dimethyl-amine,
(R)-7-Benzyl-8-(4-ethyl-phenyl)-8-methyl-5,6,7,8-tetrahydro-tetrazolo[1,5-a]pyrazine,
(S)-7-Benzyl-8-(4-ethyl-phenyl)-8-methyl-5,6,7,8-tetrahydro-tetrazolo[1,5-a]pyrazine,
(R)-8-(3-Isopropyl-1-phenyl-1H-pyrazol-4-yl)-7-thiophen-2-ylmethyl-5,6,7,8-tetrahydro-tetrazolo[1,5-a]pyrazine,
(S)-8-(3-Isopropyl-1-phenyl-1H-pyrazol-4-yl)-7-thiophen-2-ylmethyl-5,6,7,8-tetrahydro-tetrazolo[1,5-a]pyrazine,
(R)-7-(3-Bromo-benzyl)-8-(4-fluoro-phenyl)-5,6,7,8-tetrahydro-tetrazolo[1,5-a]pyrazine,
(S)-7-(3-Bromo-benzyl)-8-(4-fluoro-phenyl)-5,6,7,8-tetrahydro-tetrazolo[1,5-a]pyrazine,
(R)-7-(3-Bromo-benzy-8-m-tolyl-5,6,7,8-tetrahydro-tetrazolo[1,5-a]pyrazine,
(S)-7-(3-Bromo-benzyl)-8-m-tolyl-5,6,7,8-tetrahydro-tetrazolo[1,5-a]pyrazine,
(S)-7-Benzyl-8-(4-ethyl-phenyl)-5,6,7,8-tetrahydro-tetrazolo[1,5-a]pyrazine,
(R)-7-Benzyl-8-(4-ethyl-phenyl)-5,6,7,8-tetrahydro-tetrazolo[1,5-a]pyrazine,
(R)-7-Benzyl-8-(4-butoxy-phenyl)-5,6,7,8-tetrahydro-tetrazolo[1,5-a]pyrazine,
(S)-7-Benzyl-8-(4-butoxy-phenyl)-5,6,7,8-tetrahydro-tetrazolo[1,5-a]pyrazine,
(R)-8-(4-Fluoro-phenyl)-7-(3-methyl-benzyl)-5,6,7,8-tetrahydro-tetrazolo[1,5-a]pyrazine,
(S)-8-(4-Fluoro-phenyl)-7-(3-methyl-benzyl)-5,6,7,8-tetrahydro-tetrazolo[1,5-a]pyrazine,
(S)-7-(4-Fluoro-benzyl)-8-(3-fluoro-phenyl)-5,6,7,8-tetrahydro-tetrazolo[1,5-a]pyrazine, and
(R)-7-(4-Fluoro-benzyl)-8-(3-fluoro-phenyl)-5,6,7,8-tetrahydro-tetrazolo[1,5-a]pyrazine,
or a physiologically acceptable salt, tautomer or stereoisomer thereof.

12. A set or kit comprising:
a) separate packs of an effective amount of the compound according to claim 1, or a physiologically acceptable salt, tautomer or stereoisomer thereof; and
b) separate packs of an effective amount of a further active ingredient, wherein the further active ingredient is different from the compound according to claim 1, or a physiologically acceptable salt, tautomer or stereoisomer thereof.

13. A medicament comprising at least one compound according to claim 1, or a physiologically acceptable salt, tautomer or stereoisomer thereof.

14. A pharmaceutical composition comprising at least one compound according to claim 1, or a physiologically acceptable salt, tautomer or stereoisomer thereof, as active ingredient, together with a pharmaceutically acceptable carrier.

15. The pharmaceutical composition according to claim 14, further comprising a second active ingredient, wherein the second active ingredient is different from the compound according to claim 1.

16. A method for modulating retinoid-related orphan receptor gamma activity in a subject, the method comprising administering to a subject in need thereof an effective amount of the compound according to claim 1, or a physiologically acceptable salt, tautomer or stereoisomer thereof.

17. The method according to claim 16, wherein the subject suffers from a medical condition selected from the group consisting of rheumatoid arthritis, collagen-induced arthritis, ankylosing spondylitis, systemic lupus erythematodus, multiple sclerosis, psoriasis, atopic eczema, inflammatory bowel disease, Crohn's disease, ulcerative colitis, asthma, amyotrophic lateral sclerosis, autoimmune hepatitis, adipositas, type 1 diabetes, type 2 diabetes and insulin resistance.

18. A process for manufacturing the compound according to claim 1, the process comprising:
(a) reacting a compound of formula, $$R^1-NH_2,$$

wherein $R^1$ is as defined in claim 1;
with a compound of formula, $$R^2-CHO,$$

wherein $R^2$ is as defined in claim 1;
to provide a compound of formula, $$R^1\diagdown_{N=}\diagup^{R^2};$$

wherein $R^1$ and $R^2$ are as defined in claim 1; and
(b) reacting the compound of formula, $$R^1\diagdown_{N=}\diagup^{R^2},$$

wherein $R^1$ and $R^2$ are as defined in claim 1;
with 2-isocyanoethyl 4-methylbenzenesulfonate and a compound which is an azide anion source for an azide anion of formula, $$^-N=N^+=N^-,$$

to provide a compound of formula (I)

(I)

wherein $R^1$ and $R^2$ are as defined in claim 1;
with the proviso that the manufacture of 7-benzyl-8-(4-methoxyphenyl)-5,6,7,8-tetrahydrotetrazolo[1,5-a]pyrazine is excluded.

* * * * *

UNITED STATES PATENT AND TRADEMARK OFFICE
CERTIFICATE OF CORRECTION

PATENT NO. : 9,688,684 B2  
APPLICATION NO. : 15/105436  
DATED : June 27, 2017  
INVENTOR(S) : Dirk Finsinger et al.

It is certified that error appears in the above-identified patent and that said Letters Patent is hereby corrected as shown below:

In the Claims

Column 89, Line 15, "denotes $Ar^e$ or" should read --"denotes $Ar^2$ or"--

Column 89, Line 48, "3-cyclopropyl-1 ethyl-1H-pyrazol-4-yl" should read --3-cyclopropyl-1-ethyl-1H-pyrazol-4-yl--

Column 92, Line 11, "tetrazolo[1,5 a]pyrazine" should read --tetrazolo[1,5-a]pyrazine--

Column 92, Line 20, "tetrazolo[1,5 a]pyrazine" should read --tetrazolo[1,5-a]pyrazine--

Signed and Sealed this  
Tenth Day of April, 2018

Andrei Iancu  
*Director of the United States Patent and Trademark Office*